(12) United States Patent
Siev et al.

(10) Patent No.: US 6,506,754 B1
(45) Date of Patent: Jan. 14, 2003

(54) NON-COVALENT THROMBIN INHIBITORS

(75) Inventors: Daniel Vanna Siev, San Diego, CA (US); Gian Luca Araldi, San Diego, CA (US); Jonathan Zhanqi Ho, Beijing (CN); John Eugene Reiner, San Diego, CA (US); Joseph Edward Semple, San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 09/549,453

(22) Filed: Apr. 14, 2000

(Under 37 CFR 1.47)

(51) Int. Cl.⁷ .......................... C07K 5/06; A61K 38/00; A61P 7/02
(52) U.S. Cl. .................. 514/252.02; 544/297; 544/405; 544/238; 514/275; 514/255.06
(58) Field of Search ................................. 544/297, 405, 544/238; 514/275, 255.06, 252.02

(56) References Cited

FOREIGN PATENT DOCUMENTS

| WO | WO 9701338 | 1/1997 | ......... A61K/31/445 |
|----|-----------|--------|----------------------|
| WO | WO 9746207 | 12/1997 | |
| WO | WO 9911267 | 3/1999 | ......... A61K/31/495 |
| WO | WO 9961442 | 12/1999 | ......... C07D/471/04 |
| WO | WO 9962904 | 12/1999 | ......... C07D/471/02 |
| WO | WO 0069834 | 11/2000 | ......... C07D/241/20 |

*Primary Examiner*—Richard L. Raymond
*Assistant Examiner*—Hong Liu
(74) *Attorney, Agent, or Firm*—Suzanne L. Biggs; Pillsbury Winthrop LLP

(57) ABSTRACT

The present invention provides compounds which have a pyrazinone or pyridinone ring at P3 and which feature a six member heterocyclic ring having two ring nitrogen atoms and the remainder of the ring atoms carbon atoms at P1. These compounds have biological activity as active and potent inhibitors of thrombin. Their pharmaceutically acceptable salts, pharmaceutical compositions thereof and methods of using these compounds and pharmaceutical compositions comprising these compounds as therapeutic agents for treatment of disease states in mammals which are characterized by abnormal thrombosis are also described.

43 Claims, 20 Drawing Sheets

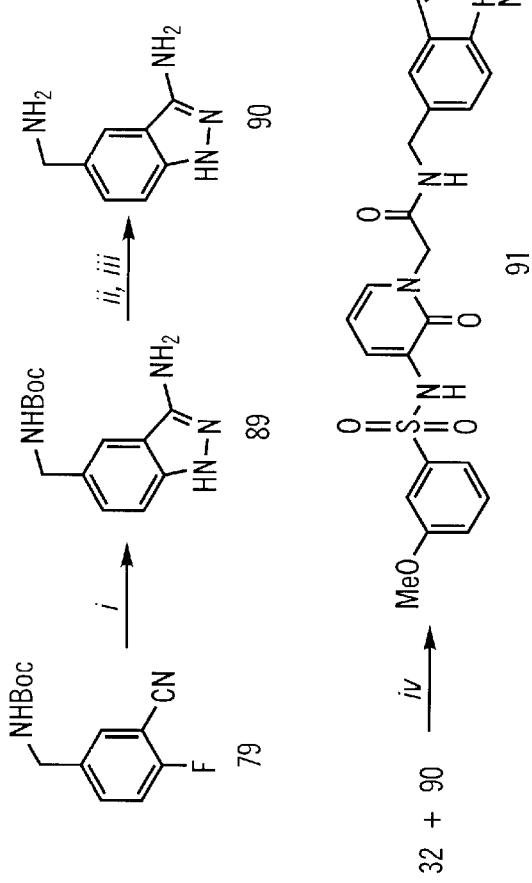
FIG. 12.
FIG. 14.
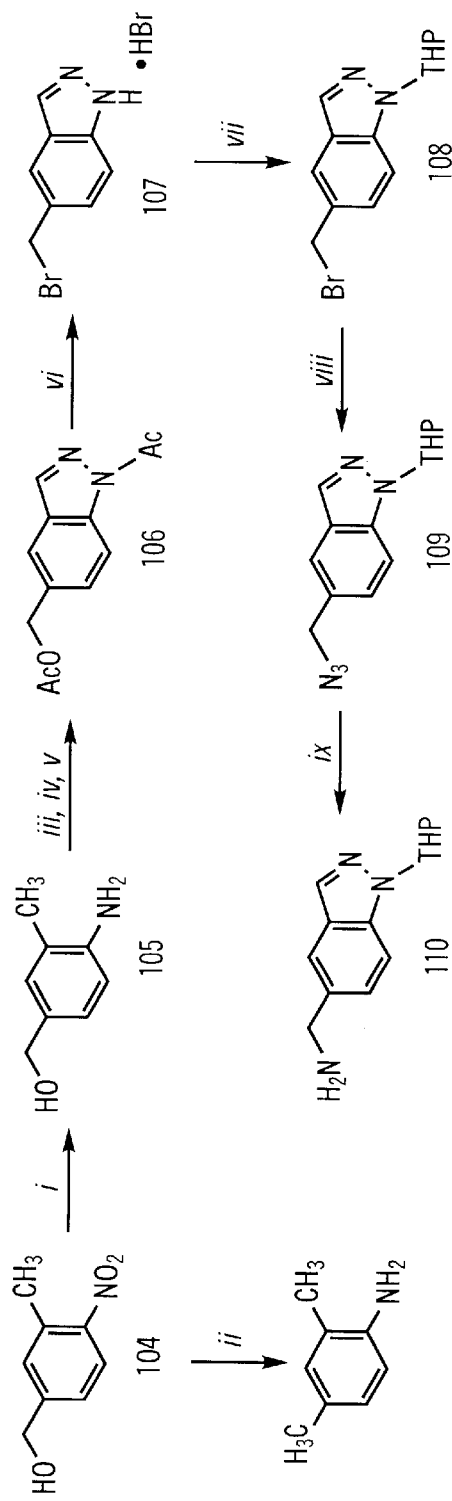

FIG. 24.

NON-COVALENT THROMBIN INHIBITORS

TECHNICAL FIELDS

In one aspect, the present invention relates to compounds which are potent inhibitors of thrombin. In another aspect, the present invention relates to novel peptide analogs, their pharmaceutically acceptable salts, and pharmaceutically acceptable compositions thereof, which are useful as potent inhibitors of blood coagulation in vitro and in vivo in mammals. In yet another aspect, the invention relates to methods of using these inhibitors as therapeutic agents for disease states in mammals characterized by abnormal thrombosis. In a further aspect, the present invention relates to methods of using these inhibitors as in vitro diagnostic agents.

BACKGROUND AND INTRODUCTION TO THE INVENTION

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) Blood 76: 1–16. and Lawson, J. H., Kalafatis, M., Stram, S., and Mann, K. G. (1994) J. Biol. Chem. 269: 23357–23366).

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va, and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic mechanisms", *Disorders of Hemostasis*, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et al., "Surface-Dependent Reactions of the Vitamin K-Dependent Enzyme Complexes," *Blood*, 76:1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", *J. Clin. Invest.*, 71:1383–1391 (1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., *Arch. Biochem. Biophys.*, 105:58 (1964). Beyond its direct role in the formation and stabilization of fibrin rich clots, the enzyme has been reported to have profound bioregulatory effects on a number of cellular components within the vasculature and blood. Shuman, M. A., *Ann. NY Acad. Sci.*, 405:349 (1986).

It is believed that thrombin is the most potent agonist of platelet activation, and it has been demonstrated to be the primary pathophysiologic-mediator of platelet-dependent arterial thrombus formation. Edit, J. F. et al., *J. Clin. Invest.*, 84:18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., *Platelets in Biology and Pathology*, pp. 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., *Blood*, 77:2641 (1991). This positive feedback process results in the local generation of large concentrations of thrombin within the vicinity of the thrombus which supports further thrombus growth and extension. Mann, K. G. et al., *Blood*, 76:1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., *Biochemistry*, 27:769, (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., *Science*, 235:1348 (1987). The activation of protein C by thrombin in the absence of thrombomodulin is poor.

Thrombin has also been shown to be a potent direct mitogen for a number of cell types, including cells of mesenchymal, origin such as vascular smooth muscle cells. Chen, L. B. and Buchanan, J. M., *Proc. Natl. Acad. Sci. USA*, 72:131 (1975). The direct interaction of thrombin with vascular smooth muscle also results in vasoconstriction. Walz, D. A. et al., *Proc. Soc. Expl. Biol. Med.*, 180:518 (1985). Thrombin acts as a direct secretagogue inducing the release of a number of bioactive substances from vascular endothelial cells including tissue plasminogen activator. Levin, E. G. et al., *Thromb. Haemost.*, 56:115 (1986). In addition to these direct effects on vascular cells, the enzyme can indirectly elaborate potent mitogenic activity on vascular smooth muscle cells by the release of several potent growth factors (e.g., platelet-derived growth factor and epidermal growth factor) from platelet a-granules following thrombin-induced activation. Ross, R., *N. Engl. J. Med.*, 314:408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., *Thrombosis in Cardiovascular Disorder*, p. 327, W. B. Saunders Co. (Fuster, V. and Verstraete, M. edit. 1991); Califf, R. M. and Willerson, J. T., id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., *J. Am. Coll. Cardiol.*, 67:3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., *J. Am. Coll. Cardiol.*, 17:2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aa chain of fibrinogen, which is the primary physiological substrate for thrombin, is reported to contain a glycine residue in this position while the cleavage site on the Bb chain contains a serine, as shown below:

```
                                              [SEQ. ID. NO. 1]
  P4   P3   P2   P1   P1'
  Gly-Gly-Val-Arg/Gly Fibrinogen Aa Chain

[SEQ. ID. NO. 2]
      Phe-Ser-Ala-Arg/Gly Fibrinogen Bb Chain
```

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., *Symposia Biologica Hungarica*, 25:277 (1984);

Bajusz, S. et al., *J. Med. Chem.* 33:1729 (1990); Bajusz, S. et al., Int. *J. Peptide Protein Res.* 12:217 (1970); Kettner, C. and Shaw, E., *Methods Enzymol.*, 80:826 (1987); Kettner, C. et al., EP 293,881 (published Dec. 7, 1988); Kettner, C., et al., *J. Biol. Chem.*, 265:18209 (1990). These molecules have been reported to be potent anticoagulants in the prevention of platelet-rich arterial thrombosis. Kelly, A. B. et al., *Thromb. Haemostas.*, 65:736 at abstract 257 (1991). Other peptidyl aldehydes have been proposed or reported as inhibitors of thrombin. See, e.g., Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing an uncharged amino acid in the P3 recognition subsite have been reported.

The compound, Argatroban (also called 2R,4R-4-methyl-1-[N-2-(3-methyl-1,2,3,4-tetrahydro-8-quino linesulfonyl)-L-argininyl]-2-piperdinecarboxylic acid), is also reported to bind directly to the active site of thrombin and has been thought to be the most potent and selective compound in the class of non-peptidyl inhibitors of this enzyme. Okamoto, S. et al., *Biochem. Biophys. Res. Commun.*, 101:440 (1981). Argatroban has been reported to be a potent antithrombotic agent in several experimental models of acute arterial thrombosis. Jang, I. K. et al., in both *Circulation*, 81:219 (1990) and *Circ. Res.*, 67:1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., *Thromb. Haemostas.*, 66:141 (1991). Hirudin is reported to be a 65 amino acid polypeptide originally isolated from leech salivary gland extracts. It is said to be one of the most potent inhibitors of thrombin known. Marki, W. E. and Wallis, R. B., *Thromb. Haemostas.*, 64:344 (1990). It has been reported to inhibit thrombin by binding to both its anion-binding exo-site and to its catalytic active site which are distinct and physically distant from each other. Rydel, T. J. et al., *Science*, 249:277 (1990). Hirudin has been reported to be a potent antithrombotic agent in vivo. Markwardt, F. et al., *Pharmazie*, 43:202 (1988); Kelly, A. B. et al., *Blood*, 77:(1991). In addition to its antithrombotic effects, hirudin has been reported to also effectively inhibit smooth muscle proliferation and the associated restenosis following mechanical damage to an atherosclerotic rabbit femoral artery. Sarembock, I. J. et al., *Circulation*, 84:232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., *J. Biol. Chem.*, 264:8692 (1989); Naski, M. C. et al., *J. Biol. Chem.*, 265:13484 (1990). The region of hirudin represented by hirugen has been reported, as according to by x-ray crystallographic analysis, to bind directly to the exo site of thrombin. Skrzypczak-Jankun, E. et al., *Thromb. Haemostas.*, 65:830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, U. W. et al., *J. Biol. Chem.*, 266:16977 (1991). Hirugen also is reported to block thrombin-mediated platelet aggregation. Jakubowski, J. A. and Maraganore, J. M., *Blood*, 75:399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., *Biochemistry*, 29:7095 (1990). The hirulogs have been reported to be an effective antithrombotic agents in preventing both fibrin-rich and platelet-rich thrombosis. Maraganone, J. M. et al., *Thromb. Haemostas.*, 65:651 at abstract 17 (1991).

Certain benzamidines have been reported to inhibit thrombin though non-selectively. 4-amidinophenylpyruvic acid (APPA) has been reported to be a thrombin inhibitor with low toxicity and favourable pharmacokinetics. However, this compound was reported to be non-selective, inhibiting trypsin, plasmin and kallikrein. Markwardt et al., *Thromb. Res.*, 1:243–52 (1972). Other benzamidine-derived structures which have been reported to inhibit thrombin include the cyclic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., *Thromb. Res.*, 17:425–31 (1980). Moreover, derivatives of 4-amidinophenylalanine whose α-amino group is linked to the arylsulfonyl residue via a ω-aminoalkylcarboxylic acid as spacer have also been assessed for their inhibitory effect. Among these $N^\alpha$-(2-naphthylsulphonylglycyl)-4-amidino-phenylalanine piperidide (a-NAPAP) has been reported to possess an affinity for thrombin ($K_i=6\times10^{-9}$ M). Banner et al., *J. Biol. Chem.*, 266:20085 (1991) and Sturzebecher et al., *Thromb. Res.*, 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et al., *Thromb. Diath. Haemorrh.*, 29:154–67 (1973); Geratz et al., *J. Med. Chem.*, 16:970–5 (1973); Geratz et al., *J. Med. Chem.*, 19:634–9 (1976); Walsmann et al., *Acta Biol. Med. Germ.*, 35:K1–8 (1976); and Hauptmann et al., *Acta Biol. Med. Germ.*, 35:635–44 (1976).

Certain amidino-bearing aromatic ring structures such as β-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., *Biochim. Biophys. Acta*, 661:342–5 (1981); and Hitomi et al., *Haemostasis*, 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et al., *Thromb. Haemostas.*, 50:53 (1983). Another compound, [ethyl p-(6-guanidinohexanoyloxy)

benzoate]methane sulfonate (FOY) was reported to be a non-selective competitive inhibitor of thrombin. Ohno et al., *Thromb. Res.*, 19:579–588 (1980).

Certain compounds having inhibitory activity toward serine proteases, including thrombin, factor Xa, and trypsin, are disclosed within the following commonly assigned United States patents or published PCT applications: U.S. Pat. Nos. 5,371,072; 5,492,895; 5,534,498; 5,597,804; 5,637,599; 5,646,165; 5,656,600; 5,656,645; WO 94/13693; WO 95/35311; WO 95/35313; WO 96/19493.

Substances which interfere in the process of blood coagulation (anticoagulants) have been demonstrated to be important therapeutic agents in the treatment and prevention of thrombotic disorders (Kessler, C. M. (1991) Chest 99: 97S–112S and Cairns, J. A., Hirsh, J., Lewis, H. D., Resnekov, L., and Theroux, P. (1992) Chest 102: 456S–481S). The currently approved clinical anticoagulants have been associated with a number of adverse effects owing to the relatively non-specific nature of their effect on the blood coagulation cascade (Levine, M. N., Hirsh, J., Landefeld, S., and Raskob, G. (1992) Chest 102: 352S–363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) J. Lab. Clin. Med. 122:364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

SUMMARY OF THE INVENTION

The present invention is directed to novel compounds which have a pyridinone or a pyrazinone group at P3 and which feature a six-membered heterocyclic ring having two ring nitrogen atoms and the remainder of the ring atoms carbon atoms at P1. These compounds have activity as inhibitors of thrombin.

Thus, according to one aspect, the present invention is directed to compounds of formula (I):

wherein
(a) X is selected from the group consisting of —S(O)$_2$—NH—, —N(R')—S(O)$_2$—NH—, —C(=O)—NH—, —OC(=O)—NH—, —N(R')C(=O)—NH—, and a direct link, wherein R' is selected from hydrogen, alkyl of 1 to about 4 carbon atoms, aryl of about 6 to about 14 carbon atoms and aralkyl of about 6 to about 16 carbon atoms;
(b) R$_1$ is selected from the group consisting of:
  (1) alkyl of 1 to about 12 carbon atoms which is optionally substituted with Y$_1$ and/or Y$_2$,
  (2) alkyl of 1 to about 3 carbon atoms substituted with cycloalkyl of about 3 to about 8 carbon atoms which is optionally mono-, di-, or tri-substituted on the ring with Y$_1$, Y$_2$ and/or Y$_3$,
  (3) cycloalkyl of 3 to about 15 carbon atoms, which is optionally mono-, di-, or tri-substituted on the ring with Y$_1$, Y$_2$ and/or Y$_3$,
  (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$ and/or Y$_3$,
  (5) heterocyclo of 4 to about 10 ring atoms with the ring atoms selected from carbon and heteroatoms, wherein the heteroatoms are selected from the group consisting of oxygen, nitrogen, and S(O)$_i$, including

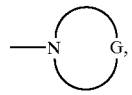

wherein

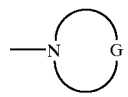

is a 5 to 7 member heterocycle of 3 to 6 ring carbon atoms, where G is —CH$_2$—, —O—, —S(=O)—, —S(O)$_2$— or —S—, which is optionally mono-, di-, or tri-substituted on the ring carbons with Y$_1$, Y$_2$ and/or Y$_3$,
  (6) alkenyl of about 2 to about 6 carbon atoms which is optionally substituted with cycloalkyl of about 5 to about 8 carbon atoms, which is optionally mono- di-, or tri-substituted on the ring carbons with Y$_1$, Y$_2$ and/or Y$_3$,
  (7) aryl of about 6 to about 14 carbon atoms which is optionally mono-, di- or tri-substituted with Y$_1$, Y$_2$, and/or Y$_3$,
  (8) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with Y$_1$, Y$_2$, and/or Y$_3$,
  (9) aralkyl of about 7 to about 15 carbon atoms which is optionally substituted on the alkyl chain with hydroxy or halogen and mono-, di-, or tri-substituted in the aryl ring with Y$_1$, Y$_2$, and/or Y$_3$,
  (10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with Y$_1$, Y$_2$, and/or Y$_3$,
  (11) aralkenyl of about 8 to about 16 carbon atoms which is optionally mono-, di-, or tri-substituted on the aryl ring with Y$_1$, Y$_2$, and/or Y$_3$,
  (12) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with Y$_1$, Y$_2$, and/or Y$_3$,

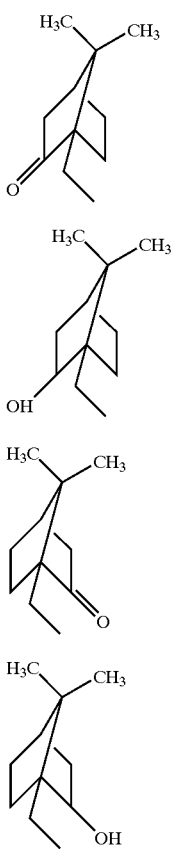

(13)

(14)

(15)

(16)

(17) fused carbocyclic alkyl of about 5 to about 15 carbon atoms,
(18) difluoromethyl or perfluoroalkyl of 1 to about 12 carbon atoms,
(19) perfluoroaryl of about 6 to about 14 carbon atoms,
(20) perfluoraralkyl of about 7 to about 15 carbon atoms, and
(21) hydrogen when X is a direct link; wherein
  (i) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, —$CF_3$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NZ_1Z_2$, —$C(O)OH$, —$C(O)OZ_1$, —$C(O)NH_2$, —$C(O)NZ_1Z_2$, —$P(O)_3H_2$, —$P(O)_3(Z_1)_2$, —$S(O)_3H$, —$S(O)_pZ_1$, —$Z_1$, —$OZ_1$, —OH, —$NH_2$, —$NHZ_1$, —$NZ_1Z_2$, N-morpholino, and —$S(O)_p(CF_2)_qCF_3$, wherein p is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms having about 3 to about 9 carbon atoms, or
  (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms having about 3 to about 9 carbon atoms;

(c) D is

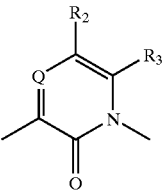

wherein
(1) $R_2$ is selected from hydrogen, halogen and alkyl of 1 to about 6 carbon atoms;
(2) $R_3$ is selected from hydrogen, alkyl of 1 to about 6 carbon atoms, cycloalkyl of 3 to about 7 carbon atoms, alkoxy of 1 to about 5 carbon atoms and trifluoromethyl;
(3) Q is —N— or —C($R_4$)—; and
(4) $R_4$ is hydrogen, alkyl of 1 to about 8 carbon atoms, hydroxy, alkoxy of 1 to about 8 carbon atoms, aralkyl of about 7 to about 15 carbon atoms, alkyl of 1 to about 5 carbon atoms substituted with cycloalkyl of 3 to about 8 carbon atoms, —$NHR_5$, —$S(O)_tR_5$, and $C(O)OR_5$;
(5) t is 0, 1 or 2;
(6) $R_5$ is hydrogen; alkyl of 1 to about 4 carbon atoms, aryl of about 6 to about 14 carbon atoms which is optionally mono-, di- or tri-substituted with $Y_1$, $Y_2$, and/or $Y_3$; heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or $Y_3$; aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$; heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$;

(d) J is selected from

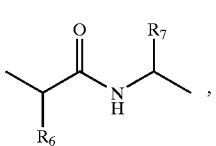

(1)

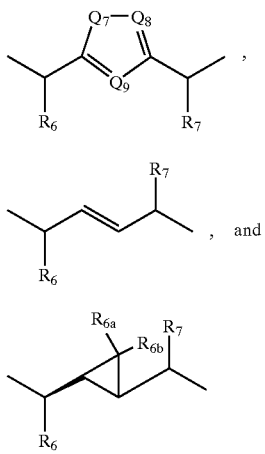

wherein $R_6$ is hydrogen or alkyl of 1 to about 3 carbon atoms; $R_{6a}$ and $R_{6b}$ are independently selected from hydrogen, fluoro, chloro and alkyl of 1 to about 3 carbon atoms; $R_7$ is hydrogen, alkyl of 1 to about 3 carbon atoms, —C(=O)$R_{7a}$, or —CH$_2$O$R_{7b}$; $R_{7a}$ is alkyl of 1 to about 6 carbon atoms, alkoxy of 1 to about 6 carbon atoms, amino, alkylamino of 1 to about 6 carbon atoms or dialkylamino of 2 to about 12 carbon atoms; $R_{7b}$ is hydrogen, acyl, or alkyl of 1 to about 6 carbon atoms; and $Q_7$, $Q_8$ and $Q_9$ are independently selected from C($R_{6a}$), N, S and O, provided that (i) $Q_7$, $Q_8$ and $Q_9$ are not all C($R_{6a}$) and (ii) only one of $Q_7$, $Q_8$ and $Q_9$ can be O or S;

(e) E is a six membered heterocyclic ring having two ring nitrogen atoms and the remainder of the ring atoms carbon atoms which is substituted with

on a ring carbon and is substituted with $R_{10}$ and $R_{11}$ on different ring carbons wherein (1) $R_8$ is selected from hydrogen, alkyl of about 1 to about 4 carbon atoms, cycloalkyl of 3 to about 7 carbon atoms, —(CF$_2$)$_k$CF$_3$, —O$R_{12}$ and —C(=O)$R_{12}$ wherein $R_{12}$ is alkyl of 1 to about 4 carbon atoms and k is 0, 1, 2 or 3;

(2) $R_9$ is selected from hydrogen and alkyl of 1 to about 4 carbon atoms;

(3) alternatively $R_8$ and $R_9$ are taken together to give a divalent radical of the formula —(CH$_2$)$_w$— wherein w is 3, 4 or 5; and (4) $R_{10}$ and $R_{11}$ are independently selected from hydrogen, alkyl of 1 to about 4 carbon atoms, alkyl of 1 to about 4 carbon atoms substituted with alkoxy of 1 to about 3 carbon atoms, alkoxy of 1 to about 8 carbon atoms, halogen, trifluoromethyl, —OC($R_{13}$)($R_{14}$)—C(=O)—$R_{15}$ wherein $R_{13}$ and $R_{14}$ are independently selected from hydrogen or alkyl of 1 to about 4 carbon atoms, $R_{15}$ is hydroxy, alkoxy of 1 to about 4 carbon atoms or —N($R_{16}$)($R_{17}$) wherein $R_{16}$ and $R_{17}$ are independently hydrogen or alkyl of 1 to about 4 carbon atoms;

and pharmaceutically acceptable salts thereof.

In one aspect, the present invention is directed to compounds which are potent inhibitors of thrombin. According to a preferred aspect, these compounds comprise novel serine protease inhibitors. The present invention is also directed to pharmaceutical compositions which comprise one of these compounds and a pharmaceutically acceptable carrier. These compounds and pharmaceutical compositions are potent inhibitors of blood coagulation in vitro and in vivo in mammals. These compounds and pharmaceutical compositions may be used as therapeutic agents for treating disease states in mammals which are characterized by abnormal thrombosis. A further aspect of the present invention is directed to the use of these compounds and pharmaceutical compositions for treatment of disease states in mammals characterized by abnormal thrombosis. An alternate aspect of the present invention is directed to methods of using these thrombin inhibitors as in vitro diagnostic agents.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound of the present invention or pharmaceutical composition comprising such a compound.

DEFINITIONS

In accordance with the present invention and as used herein, the following terms are defined to have following meanings, unless explicitly stated otherwise:

In referring to formula (I), P1, P2, P3 and P4 denote the portions of the molecule indicated below:

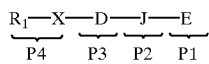

wherein $R_1$, X, D, J and E are as defined in connection with formula (I).

The term "acyl" refers to the group —C(=O)R' wherein R' is a hydrocarbyl group.

The term "alkenyl" refers to unsaturated aliphatic groups having at least one double bond.

The term "alkynyl" refers to unsaturated aliphatic groups having at least one triple bond.

The term "alkyl" refers to saturated aliphatic groups including straight-chain, branched-chain and cyclic groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aminoalkyl" refers to an alkyl group substituted with an amino (NH$_2$) group.

The term "aralkenyl" refers to an alkenyl group substituted with an aryl group. Preferably the alkenyl group has from 2 to about 6 carbon atoms.

The term "aralkyl" refers to an alkyl group substituted with an aryl group. Suitable aralkyl groups include benzyl, picolyl, and the like, all of which may be optionally substituted. Preferably the alkyl group has from 1 to about 5 carbon atoms.

The term "aryl" refers to an aromatic group which has at least one ring having a conjugated pi electron system and includes a carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural and unnatural amino acids in their D and L stereoisomers, if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid residue" refers to radicals having the structure: (1) —C(O)—R—NH—, wherein R typically is —CH(R')—, wherein R' is H or a carbon containing substituent; or (2)

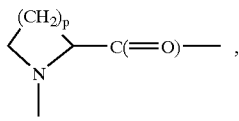

wherein p is 1, 2 or 3 representing the azetidinecarboxylic acid, proline or pipecolic acid residues, respectively.

The term "amino acid analog" refers to an amino acid wherein either the C-terminal carboxy group, the N-terminal amino group or side-chain functional group has been chemically modified to another functional group. For example, aspartic acid—(beta-methyl ester) is an amino acid analog of aspartic acid; N-ethylglycine is an amino acid analog of glycine; or alanine carboxamide is an amino acid analog of alanine.

"Arginine mimic side chain" or "side chain of an arginine mimic" refers to a group of atoms which spatially and electronically resemble or mimic the normal arginine side chain. These groups include the cyclic $R_5$ groups defined in connection with formula (I).

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Camphor derivative" refers to the groups:

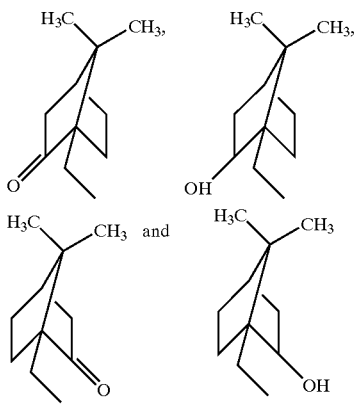

"Carbocyclic" refers to a group having one or more rings wherein the ring atoms are all carbon atoms and includes groups having aryl, cycloalkyl, and unsaturated cycloalkyl or a combination of such rings. Such groups include cyclohexyl, cycloheptenyl, tetrahydronaphthyl, phenyl, naphthyl, and the like.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, nitro, and cyano. Substituted naphthyl refers to 1- or 2-naphthyl substituted by lower alkyl, lower alkoxy, or halogen.

"Carboxylate mimic" or "carboxylic acid mimic" refers to a group which spatially and electronically mimics a carboxylic acid and provides a net negative charge, i.e., an anion, and also has a pKa value similar to that of a corresponding carboxylic acid, preferably having a pKa of about 4 to 5.

"Cycloalkenyl" or "unsaturated cycloalkyl" refers to a cyclic alkenyl group, that is, a cycloalkyl group modified by having at least one double band. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl.

"Cyclohexylmethyl" refers to a cyclohexyl group attached to $CH_2$.

"Fused carbocyclic" refers to a group having multiple rings which are fused, including multicyclic fused carbocyclic rings having both aromatic and non-aromatic rings. Suitable fused carbocyclic rings include fluorenyl, tetralin and the like.

"Fused carbocyclic alkyl" refers to an alkyl group substituted with a fused carbocyclic ring moiety, preferably a multicyclic fused carbocyclic ring having both aromatic and nonaromatic rings. Suitable fused carbocyclic alkyl groups include fluorenyl methyl and the like.

The term "halogen" refers to fluorine, chlorine, bromine and iodine.

A "heteroatom" as defined herein is an atom other than carbon or hydrogen, e.g., typically, oxygen, nitrogen or sulfur.

"Heterocyclic" refers to a group having 1 or more rings wherein the ring atoms are carbon atoms or heteroatoms, and includes rings that are reduced, saturated, unsaturated and aromatic and, if the group has more than one ring, includes a combination of such rings. Suitable heteroatoms include oxygen, nitrogen and $S(O)_i$ wherein i is 0, 1 or 2. Thus, heterocyclic groups include groups having (i) heterocyclo rings (ii) unsaturated heterocyclo rings, (iii) heteroaryl rings or (iv) a combination of such rings.

"Heteroaryl" refers to aromatic groups having a mixture of carbon atoms and heteroatoms. Preferred heteroaryl groups include those having 5 to 14 ring atoms and from 1 to 9 carbon atoms and the remainder of the ring atoms heteroatoms. Heteroaryl groups include those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and sulfur. Typical heteroaryl groups include furanyl, thienyl, pyridyl, pyrrolyl, pyrimidyl, pyrazinyl, imidazolyl, pyrazolyl, oxazolyl, thiazolyl and the like.

"Heteroaralkenyl" refers to an alkenyl group substituted with a heteroaryl group. Preferably the alkenyl group has from 2 to about 6 carbon atoms.

"Heteroaralkyl" refers to an alkyl group substituted with a heteroaryl group. Preferably the alkyl group has from 1 to about 6 carbon atoms.

"Heterocyclo" refers to a reduced heterocyclic ring system comprised of carbon, nitrogen, oxygen and/or sulfur atoms, and includes such heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Unsaturated heterocyclo" refers to a heterocyclo group which is modified by having at least one double bond, but which is not aromatic.

"Heterocycloalkyl" refers to an alkyl group substituted with a heterocyclo group. Preferably the alkyl group has from 1 to about 6 carbon atoms.

The term "hydrocarbyl" denotes an organic radical composed of carbon and hydrogen which may be aliphatic (including alkyl, alkenyl and alkynyl groups and groups which have a mixture of saturated and unsaturated bonds), alicyclic (such as cycloalkyl), aromatic (such as aryl) or combinations thereof, and may refer to straight-chained, branched-chain or to cyclic structures or to radicals having a combination thereof, as well as to radicals substituted with halogen atom(s) or heteroatoms, such as nitrogen, oxygen and sulfur and their functional groups (such as amino, alkoxy, aryloxy, lactone groups, and the like), which are commonly found in organic compounds and radicals.

The term "hydroxyalkyl" refers to an alkyl group substituted with a hydroxy group.

The term "lower" referred to herein in connection with organic radicals or compounds defines such with up to and including 6, preferably up to and including 4 and advantageously one or two carbon atoms. Such groups may be straight chain or branched chain.

"Perfluoroalkyl" refers to an alkyl group which has every hydrogen replaced with fluorine.

"Perfluoroary" refers to an aryl group which has every hydrogen replaced with fluorine.

"Perfluoroarylalkyl" or "Perfluoroaralky" refers an aralkyl group in which every hydrogen on the aralkyl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "quaternary ammonium salt" refers to compounds produced by reaction between a basic nitrogen in an R substituent and an alkylhalide, arylhalide, and aralkylhalide. Other reactants with good leaving groups may also be used, such as alkyl trifluoromethanesulfonates, alkyl methanesulfonates, and alkyl p-toluenesulfonates. A quaternary ammonium salt has a positively charged nitrogen in the R substituent. Pharmaceutically acceptable counterions include Cl—, Br⁻, I⁻, $CF_3C(O)O^-$ and $CH_3C(O)O^-$. The counterion of choice can be made using ion exchange resin columns. R groups with basic nitrogens include —$CH_2CH_2CH_2NHC(=NH)NH_2$,

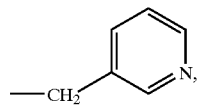

—$(CH_2)_pNH_2$, wherein p is an integer from 1 to 6. For example, the following R groups contain basic nitrogens: 3-(R)-quinuclidine, 3-(S)-quinuclidine, 3-yl-2-ethyl-4(3H)-quinazolinone, ethyl morpholine, ethyl piperidine, 2-(2-ethyl)pyridine, and 4-(methyl)-5-hydroxy-6-methyl-3-pyridine methanol.

"Trihydrocarbylsilyl" refers to the group

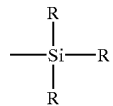

wherein each R is an independently selected hydrocarbyl group.

The term "terminal carbon" refers to the carbon atom of a straight chain alkyl which is furthest from the parent structure.

In addition, the following abbreviations stand for the following:

The symbol "=" when adjacent to a variable in text represents a double bond, e.g., (=X).

"$Ac_2O$" refers to acetic anhydride.

"AIBN" refers to 2,2'-azobisisobutyronitrile.

"9-BBN" refers to 9-borabicyclo[3.3.1]nonane.

"Bn" refers to benzyl.

"Boc" or "BOC" refers to t-butoxycarbonyl.

"$Boc_2O$" refers to Boc anhydride or di-tert-butyl dicarbonate.

"BOP" refers to benzotriazol-1-yl-oxy-tris-(dimethylamino)-phosphonium hexafluorophosphate.

"$BnSO_2$" or "$BzlSO_2$" refers to benzylsulfonyl.

"t-BuOK" refers to potassium tert-butoxide.

"Cbz" or "CBz" refers to benzyloxycarbonyl.

"CsOAc" refers to Cesium acetate.

"DCA" refers to dichloroacetic acid.

"DCC" refers to N,N'-dicyclohexylcarbodiimide.

"DCE" refers to 1,2-dichloroethane.

"DCM" refers to dichloromethane (also called methylene chloride).

"DEAD" refers to diethyl azodicarboxylate.
"DHP" refers to 3,4-dihydro-2H-pyran.
"DMF" refers to N,N-dimethylformamide.
"DMSO" refers to dimethyl sulfoxide.
"DMAP" refers to 4-dimethylamino-pyridine.
"DPPA" refers to diphenylphosphoryl azide.
"EDAC" or "EDC" refers to 1-ethyl-3-(3-dimethylamino-propyl) carbodiimide hydrochloride salt.
"Et$_3$N" refers to triethylamine.
"EtOAc" refers to ethyl acetate.
"EtOH" refers to ethanol.
"HATU" refers to O-(7-azabenzotriazol-1-yl)-1,1,3,3-tetramethyluronium hexafluorophosphate.
"HBTU" refers to 2-(1H-benzotriazol-1-yl)-1,1,3,3-tetramethyluronium hexafluorophosphate.
"HCl" refers to hydrochloric acid.
"HOAc" refers to acetic acid.
"HOAt" refers to 1-hydroxy-7-azabenzotriazole.
"HOBt" refers to 1-hydroxybenzotriazole monohydrate.
"HPLC" refers to high pressure liquid chromatography.
"i-BuOCOCl" refers to isobutyl chloroformate.
"KOAc" refers to potassium acetate.
"LiAlH$_4$" refers to lithium aluminum hydride.
"LiAlH$_2$(OEt)$_2$" refers to lithium diethoxy aluminum hydride.
"Me" refers to methyl.
"MeOH" refers to methanol.
"NaOH" refers to sodium hydroxide.
"NBS" refers to N-bromosuccinimide.
"NMM" refers to N-methylmorpholine.
"Ph$_3$P" or "PPh$_3$" refers to triphenylphosphine.
"2-PrPen" refers to 2-propylpentanoyl.
"pTSA catalyst" refers to para-toluenesulfonic acid catalyst.
"TBTU" refers to 2-(1H-benzotriazol-1-yl)-1,1,3,3-tetramethyluronium tetrafluoroborate.
"TEA" refers to triethylamine.
"TFA" refers to trifluoroacetic acid.
"THF" refers to tetrahydrofuran.
"TLC" refers to thin layer chromatography.

BRIEF DESCRIPTION OF THE DRAWINGS

FIG. 12 depicts a reaction scheme for the preparation of a compound having thrombin inhibitory activity. In this figure, "i" through "iv" are defined as follows: i) hydrazine, n-butanol, reflux 22 hours; ii) 2M HCl in dioxane, room temperature 3 hours; iii) OH$^-$ resin; and iv) HOAt, EDC, DMF, room temperature 15 hours. These procedures are more fully described in Examples 70 to 72.

FIG. 14 depicts a reaction scheme for the synthesis of an intermediate used in preparing a compound having thrombin inhibitory activity which has a 5-(aminomethyl)indazole at P1. In this figure, "i" through "ix" are defined as follows: i) 10% Pd/C, H$_2$ (10 psi), ethanol, room temperature 1.5 hours; ii) 10% Pd/C, H$_2$ (30 psi), ethanol, room temperature 8 hours; iii) KOAc, Ac$_2$O, CHCl$_3$, reflux 3 hours; iv) cool to room temperature, isoamylnitrite, 18-crown-6, reflux 28 hours; v) room temperature, Ac$_2$O, room temperature 12 hours; vi) aqueous 48% HBr, room temperature 16 hours; vii) DHP, THF, reflux 2 hours, room temperature 12 hours; viii) NaN$_3$, DMF, 90° C., 30 minutes and ix) LiAlH$_4$, THF, 0° C., one hour. These procedures are more fully described in Examples 79 to 84.

Figure 24:
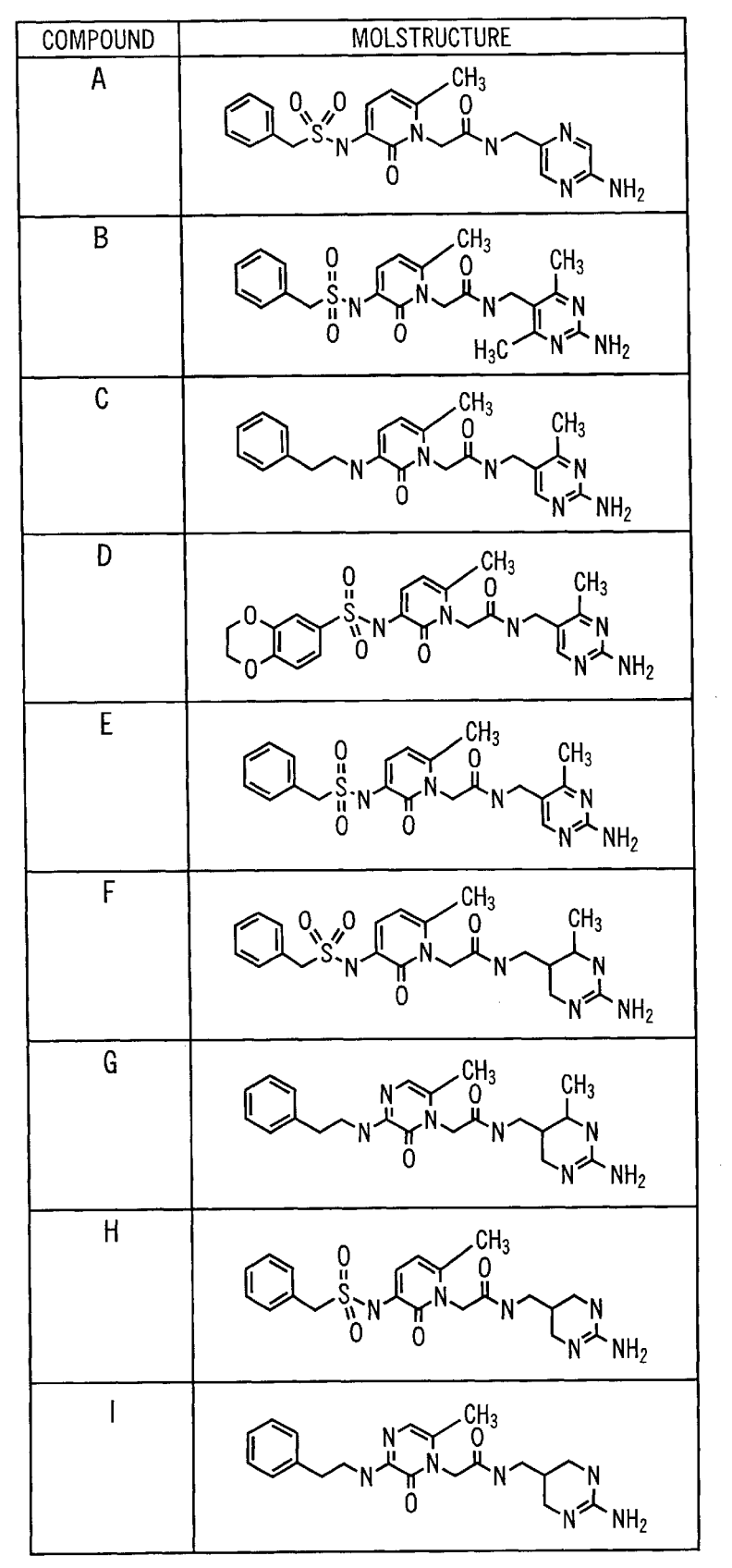

FIG. 24 depicts certain compounds of the present invention.

DETAILED DESCRIPTION OF THE INVENTION

1. Preferred Compounds

Figure 1:
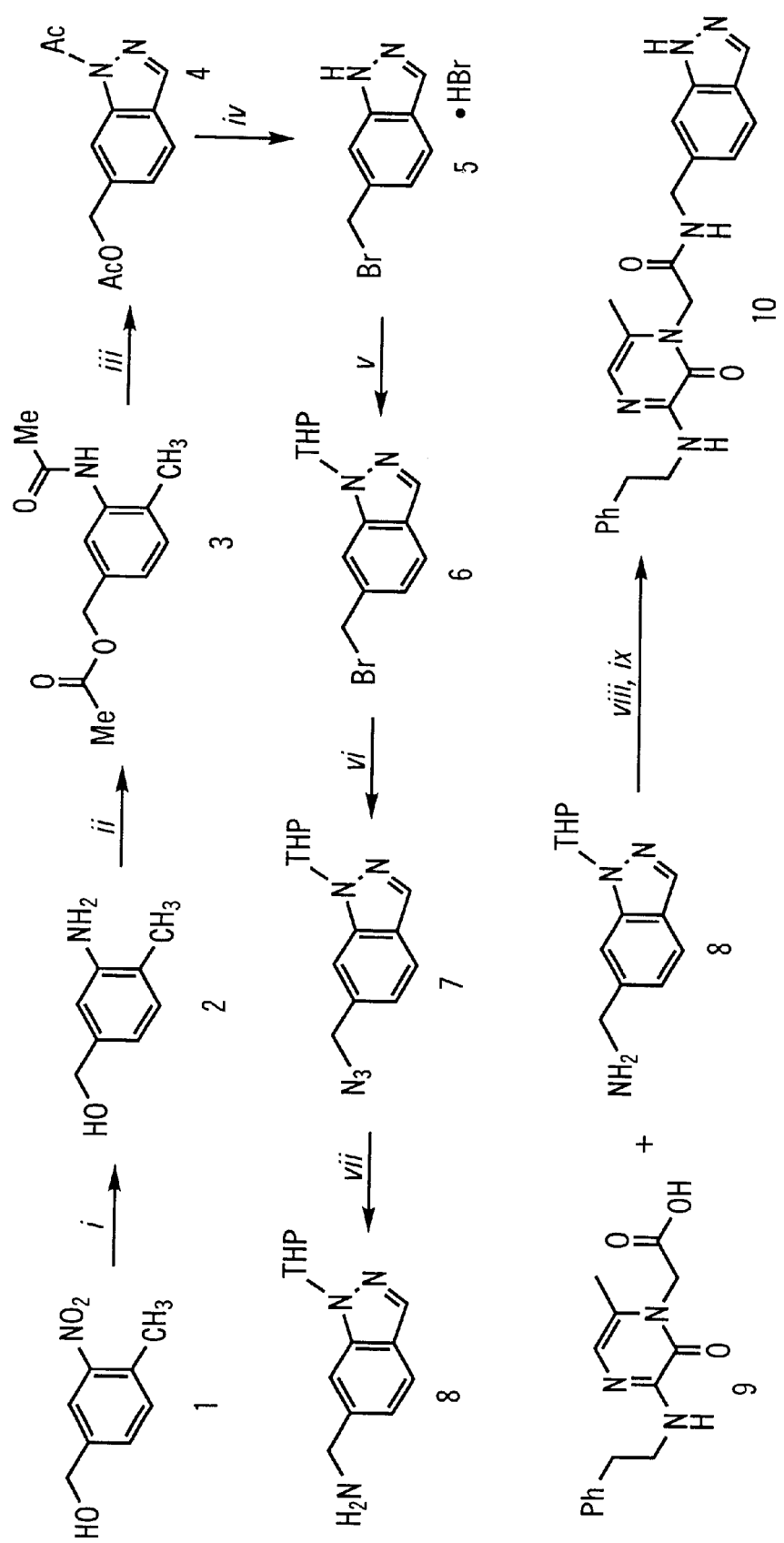
FIG. 1 depicts a reaction scheme for the synthesis of a compound having thrombin inhibitory activity. In this figure "i" through "ix" are defined as follows: i) H$_2$ balloon, 10% Pd/C, EtOAc, room temperature 48 hours, 51% yield; ii) Ac$_2$O/KOAc, CHCl$_3$, reflux 2 hours, flash chromatography, 92% yield; iii) isoamylnitrite, KOAc, catalytic amount 18-crown-6, Ac$_2$O, CHCl$_3$, reflux 28 hours, 95% yield; iv) aqueous 48% HBr, room temperature 46 hours, 84% yield; v) DHP, THF, reflux 2 hours, 72% yield; vi) NaN$_3$, DMF, 90° C. 0.5 hour, 83% yield; vii) LiAlH$_4$, THF, 0° C. 1 hour; viii) EDC, HOAt, NMM, DMF, room temperature 16 hours; and ix) HCl, DCM. These procedures are more fully described in Examples 1 to 8.

Thus, it is provided according to a first aspect of the present invention compounds of formula (I):

wherein
(a) X is selected from the group consisting of —S(O)$_2$—NH—, —N(R')—S(O)$_2$—NH—, —C(=O)—NH—, —OC(=O)—NH—, —N(R')C(=O)—NH—, and a direct link, wherein R' is selected from hydrogen, alkyl of 1 to about 4 carbon atoms, aryl of about 6 to about 14 carbon atoms and aralkyl of about 6 to about 16 carbon atoms;
(b) R$_1$ is selected from the group consisting of:

(1) alkyl of 1 to about 12 carbon atoms which is optionally substituted with Y$_1$ and/or Y$_2$,
(2) alkyl of 1 to about 3 carbon atoms substituted with cycloalkyl of about 3 to about 8 carbon atoms which is optionally mono-, di-, or tri-substituted on the ring with Y$_1$, Y$_2$ and/or Y$_3$,
(3) cycloalkyl of 3 to about 15 carbon atoms, which is optionally mono-, di-, or tri-substituted on the ring with Y$_1$, Y$_2$ and/or Y$_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$ and/or Y$_3$,
(5) heterocyclo of 4 to about 10 ring atoms with the ring atoms selected from carbon and heteroatoms, wherein the heteroatoms are selected from the group consisting of oxygen, nitrogen, and S(O)$_i$, including

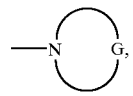

wherein

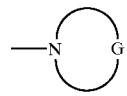

is a 5 to 7 member heterocycle of 3 to 6 ring carbon atoms, where G is —CH$_2$—, —O—, —S(=O)—, —S(O)$_2$— or —S—, which is optionally mono-, di-, or tri-substituted on the ring carbons with Y$_1$, Y$_2$ and/or Y$_3$,
(6) alkenyl of about 2 to about 6 carbon atoms which is optionally substituted with cycloalkyl of about 5 to about 8 carbon atoms, which is optionally mono-, di-, or tri-substituted on the ring carbons with Y$_1$, Y$_2$ and/or Y$_3$,
(7) aryl of about 6 to about 14 carbon atoms which is optionally mono-, di- or tri-substituted with Y$_1$, Y$_2$, and/or Y$_3$,
(8) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with Y$_1$, Y$_2$, and/or Y$_3$,
(9) aralkyl of about 7 to about 15 carbon atoms which is optionally substituted on the alkyl chain with hydroxy or halogen and mono-, di-, or tri-substituted in the aryl ring with Y$_1$, Y$_2$, and/or Y$_3$,
(10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with Y$_1$, Y$_2$, and/or Y$_3$,
(11) aralkenyl of about 8 to about 16 carbon atoms which is optionally mono-, di-, or tri-substituted on the aryl ring with Y$_1$, Y$_2$, and/or Y$_3$,
(12) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with $Y_1$, $Y_2$, and/or $Y_3$, (13)

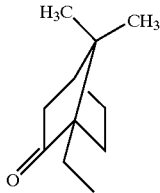

(14)

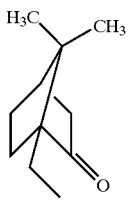

(15)

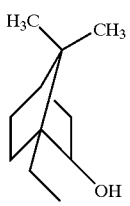

(16)

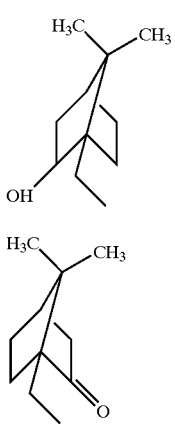

(17) fused carbocyclic alkyl of about 5 to about 15 carbon atoms,
(18) difluoromethyl or perfluoroalkyl of 1 to about 12 carbon atoms,
(19) perfluoroaryl of about 6 to about 14 carbon atoms,
(20) perfluoraralkyl of about 7 to about 15 carbon atoms, and
(21) hydrogen when X is a direct link;
  wherein
    (i) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, —$CF_3$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NZ_1Z_2$, —$C(O)OH$, —$C(O)OZ_1$, —$C(O)NH_2$, —$C(O)NZ_1Z_2$, —$P(C)_3H_2$, —$P(O)_3(Z_1)_2$, —$S(O)_3H$, —$S(O)_pZ_1$, —$Z_1$, —$OZ_1$, —$OH$, —$NH_2$, —$NHZ_1$, —$NZ_1Z_2$, N-morpholino, and —$S(O)_p(CF_2)_qCF_3$, wherein p is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms having about 3 to about 9 carbon atoms, or (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms having about 3 to about 9 carbon atoms;

(c) D is

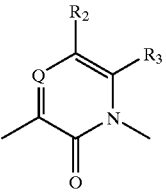

wherein
(1) $R_2$ is selected from hydrogen, halogen and alkyl of 1 to about 6 carbon atoms;
(2) $R_3$ is selected from hydrogen, alkyl of 1 to about 6 carbon atoms, cycloalkyl of 3 to about 7 carbon atoms, alkoxy of 1 to about 5 carbon atoms and trifluoromethyl;
(3) Q is —N— or —$C(R_4)$—; and
(4) $R_4$ is hydrogen, alkyl of 1 to about 8 carbon atoms, hydroxy, alkoxy of 1 to about 8 carbon atoms, aralkyl of about 7 to about 15 carbon atoms, alkyl of 1 to about 5 carbon atoms substituted with cycloalkyl of 3 to about 8 carbon atoms, —$NHR_5$, —$S(O)_tR_5$, and $C(O)OR_5$;
(5) t is 0, 1 or 2;
(6) $R_5$ is hydrogen; alkyl of 1 to about 4 carbon atoms, aryl of about 6 to about 14 carbon atoms which is optionally mono-, di- or tri-substituted with $Y_1$, $Y_2$, and/or $Y_3$; heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or $Y_3$; aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$; heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$;

(d) J is selected from

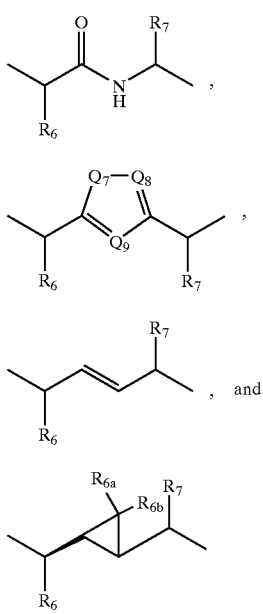

wherein $R_6$ is hydrogen or alkyl of 1 to about 3 carbon atoms; $R_{6a}$ and $R_{6b}$ are independently selected from hydrogen, fluoro, chloro and alkyl of 1 to about 3 carbon atoms; $R_7$ is hydrogen, alkyl of 1 to about 3 carbon atoms, —C(=O)$R_{7a}$, or —CH$_2$CR$_{7b}$; $R_{7a}$ is alkyl of 1 to about 6 carbon atoms, alkoxy of 1 to about 6 carbon atoms, amino, alkylamino of 1 to about 6 carbon atoms or dialkylamino of 2 to about 12 carbon atoms; $R_{7b}$ is hydrogen, acyl, or alkyl of 1 to about 6 carbon atoms; and $Q_7$, $Q_8$ and $Q_9$ are independently selected from C($R_{6a}$), N, S and O, provided that (i) $Q_7$, $Q_8$ and $Q_9$ are not all C($R_{6a}$) and (ii) only one of $Q_7$, $Q_8$ and $Q_9$ can be O or S;

(e) E is a six membered heterocyclic ring having two ring nitrogen atoms and the remainder of the ring atoms carbon atoms which is substituted with

on a ring carbon and is substituted with $R_{10}$ and $R_{11}$ on different ring carbons wherein (1) $R_8$ is selected from hydrogen, alkyl of about 1 to about 4 carbon atoms, cycloalkyl of 3 to about 7 carbon atoms, —(CF$_2$)$_k$CF$_3$, —OR$_{12}$ and —C(=O)R$_{12}$ wherein $R_{12}$ is alkyl of 1 to about 4 carbon atoms and k is 0, 1, 2 or 3;

(2) $R_9$ is selected from hydrogen and alkyl of 1 to about 4 carbon atoms;

(3) alternatively $R_8$ and $R_9$ are taken together to give a divalent radical of the formula —(CH$_2$)$_w$— wherein w is 3, 4 or 5; and (4) $R_{10}$ and $R_{11}$ are independently selected from hydrogen, alkyl of 1 to about 4 carbon atoms, alkyl of 1 to about 4 carbon atoms substituted with alkoxy of 1 to about 3 carbon atoms, alkoxy of 1 to about 8 carbon atoms, halogen, trifluoromethyl, —OC(R$_{13}$)(R$_{14}$)—C(=O)—R$_{15}$ wherein $R_{13}$ and $R_{14}$ are independently selected from hydrogen or alkyl of 1 to about 4 carbon atoms, $R_{15}$ is hydroxy, alkoxy of 1 to about 4 carbon atoms or —N(R$_{16}$)(R$_{17}$) wherein $R_{16}$ and $R_{17}$ are independently hydrogen or alkyl of 1 to about 4 carbon atoms;

and pharmaceutically acceptable salts thereof.

Preferred X groups include —S(O)$_2$—NH—, and a direct link.

Especially preferred, according to one aspect, for X is —S(O)$_2$—NH—. According to an alternate aspect, especially preferred for X is a direct link.

Preferred $R_1$ groups include alkyl, substituted aralkyl, aryl, substituted aryl, alkyl substituted with $Y_1$ and/or $Y_2$ and alkyl substituted with optionally substituted cycloalkyl. According to one aspect of the present invention, particularly preferred $R_1$ substituents include substituted or unsubstituted phenyl and substituted or unsubstituted benzyl. According to one preferred aspect, $R_1$ is phenyl, 2,3-dihydrobenzo-[b]furanyl, or benzyl. According to an alternate preferred aspect, $R_1$ is alkyl substituted with $Y_1$ and/or $Y_2$ wherein $Y_1$ and $Y_2$ are independently phenyl or substituted phenyl or alkyl substituted with cycloalkyl which is optionally substituted on the ring with $Y_1$ wherein $Y_1$ is phenyl or substituted phenyl.

Preferred D groups include those where Q is —N— or —C($R_4$)— where $R_4$ is hydrogen. More preferably Q is —N—. Particularly preferred are D groups where $R_2$ is hydrogen, especially preferred D groups include those wherein $R_3$ is methyl.

Suitable E groups include:

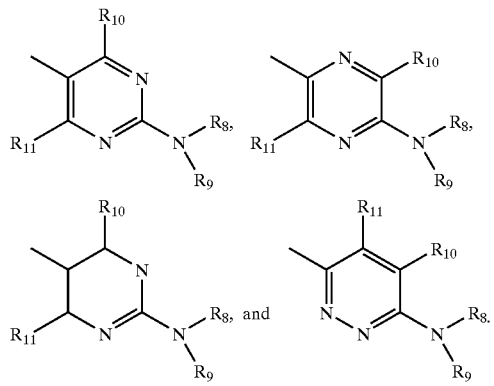

Particularly preferred E groups include the following E groups:

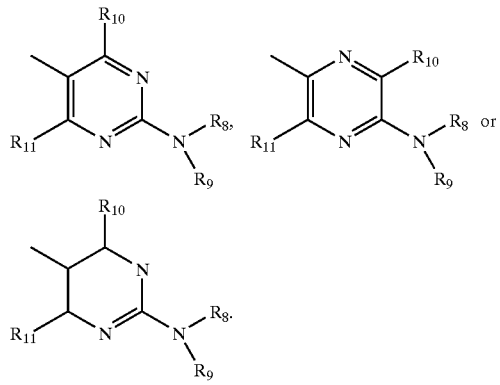

Especially preferred E groups include

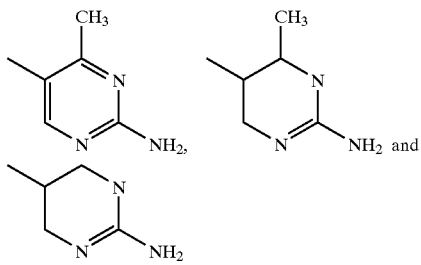

Preferred compounds according to one aspect of the present invention include those wherein $R_1$ is benzyl, substituted benzyl, phenyl, substituted phenyl; alkyl substituted with $Y_1$ and/or $Y_2$ wherein, preferably, $Y_1$ and $Y_2$ are independently phenyl or substituted phenyl, or alkyl substituted with cycloalkyl which is optionally substituted with $Y_1$ wherein $Y_1$ is preferably phenyl or substituted phenyl. Especially preferred substituted phenyl groups include 2,3-dihydrobenzofuran-5-yl. Preferably, X is —S(O)$_2$— or a direct link. When X is —S(O)$_2$—, $R_1$ is preferably benzyl, substituted benzyl, phenyl or substituted phenyl, more particularly 2,3-dihydrobenzofuran-5-yl. When X is a direct link, $R_1$ is preferably alkyl mono- or di-substituted with phenyl or substituted phenyl or alkyl substituted with cycloalkyl which is substituted on the ring with phenyl or substituted phenyl. According to this aspect, preferred E groups include:

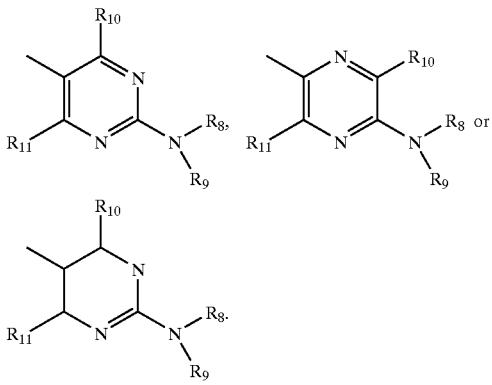

Especially preferred E groups include

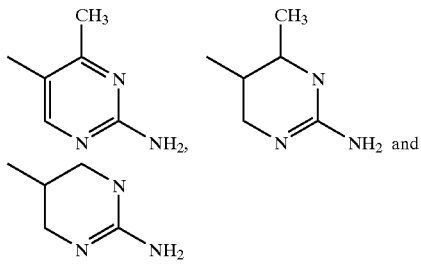

Preferred compounds according to this aspect include those having D groups where Q is —N— or —C(H)—, more preferably Q is —N—. Preferred $R_2$ groups include hydrogen.

Preferred $R_3$ groups include hydrogen and methyl, especially preferred is methyl.

According to one aspect of the present invention, preferred compounds include those having D groups where Q is —N— or —C(H)—, more preferably Q is —N—. According to this aspect, E is preferably selected from

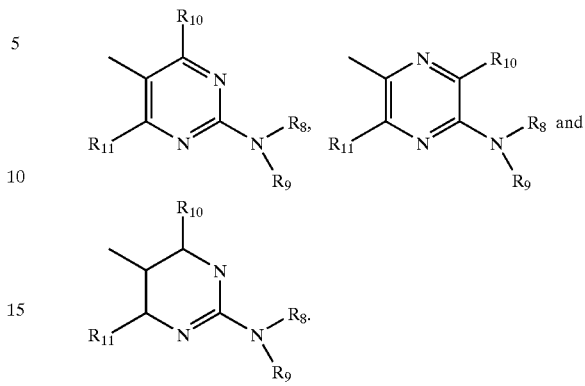

Especially preferred compounds according to this aspect include those wherein $R_2$ is hydrogen, $R_3$ is methyl, and J is selected from

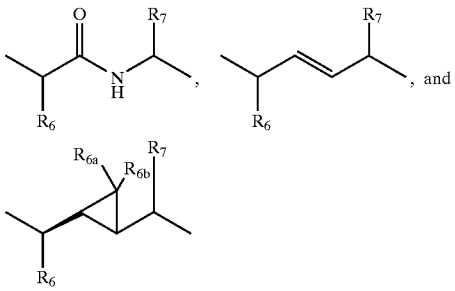

where more preferably $R_6$ and $R_7$ are hydrogen. Especially preferred E groups according to this aspect include

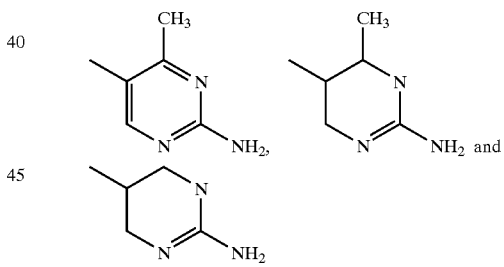

More preferably J is

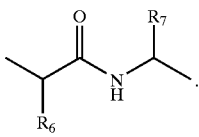

Also preferred are compounds having D groups where Q is —N— or —C(H)—, more preferably Q is —N—.

Preferred $R_6$ groups include hydrogen, and alkyl of 1 to 3 carbon atoms. Especially preferred are compounds wherein $R_6$ is hydrogen.

Preferred compounds of the present invention include those depicted in FIGS. 17 to 20 and 24.

For any given variable having a value of 0, the bond attached to the variable is not present, for example, with the group —(R)$_n$, if n is 0, then the single bond that would attach to R is also not present.

The compounds of present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

In the compounds of formula I, combinations of substituents and/or variables are permissible only if such combinations result in stable compounds.

Description of compounds of the present invention are limited by principles of chemical bonding known to those skilled in the art.

2. General Information Regarding Synthesis

Certain compounds included in variables $R_1$, X, D and J may be purchased from commercially available sources such as Sigma, Fluka, Aldrich, Nova and Calbiochem or synthesized by one skilled in the art. See, e.g., Owens, T. D.; Semple, J. E. *Bioorg. Med. Chem. Lett.* 1998, 8, 3683. Semple, J. E.; Rowley, D. C.; Owens, T. D.; Minami, N. K.; Uong, T. H.; Brunck, T. K. ibid. 1998, 8, 3525. Semple, J. E. *Tetrahedron Lett.* 1998, 39, 6645. Semple, J. E. *Bioorg. Med. Chem. Lett.* 1998, 8, 2501. Reiner, J. R.; Lim-Wilby, M. S.; Brunck, T. K.; Uong, T. H.; Goldman, E. A.; Abelman, M. A., Nutt, R. F.; Semple, J. E.; Tamura, S. Y. *Bioorg. Med. Chem. Lett.* 1999, 9, 895. Abelman, M. M.; Miller, T. A.; Nutt, R. F. U.S. Pat. No. 5,696,231, 1997. Marlowe, C. K.; Scarborough, R. M.; Laibelman, A. M.; Sinha, U.; Zhu. B.-Y. U.S. Pat. No. 5,721,214, 1998.

To synthesize intermediates for E, see, e.g., Palermo, M. G. *Tetrahedron Lett.* 37 (17), 1996, 2885–2886; Goodman, M. et. al. *J. Org. Chem.* 1998, 3804; Charette, A. B; Prescott, S.; Brochu, C. *J. Org. Chem.* 1995, 60, 1081–1083; Barrett, A. G. M.; Doubleday, W. W.; Kasdorf, K.; and G. J. Tustin, G. J. *J. Org. Chem.* 1996, 61, 3280–3288; Sun, J.-H.; Teleha, C. A.; Yan, J.-S.; Rodgers, J. D.; Nugiel, D. A. *J. Org. Chem.* 1997, 62, 5627–5629.

$R_1X$ may be purchased from commercially available sources such as Sigma, Fluka, Aldrich, Nova and Calbiochem or synthesized by one skilled in the art. See, e.g., Sanderson, P. E. J., et al., *J. Med. Chem.* 1998, 41, 4466–4474; Miller, W. D.; Tao, E. V. P. USP (1995) U.S. Pat. No. 5,387,681.

Preferred means of chemically coupling (as for example, amide bond function) include formation of a peptide bond by using conventional coupling reagents known in the art. See Bodanszky, N., *Peptide Chemistry*, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling of the include DCC with HOBt, EDC with HOBt, HBTU or TBTU. In two-step coupling, an activated ester or anhydride of the C-terminal carboxy group of one coupling partner is formed prior to its coupling to the other coupling partner.

For preparation of certain compounds having hydrogenation sensitive substituent groups, it is preferred to avoid the use of hydrogen gas with palladium on carbon for hydrogenation steps. Another preferred method for preparing compounds of the present invention containing hydrogenation sensitive groups such as alkenyl or aryl moieties substituted with halogen, cyano, nitro, or —S—$Z_1$, is to use boron tris(trifluoroacetate), B(OCOCF$_3$)$_3$, to cleave protecting groups such as the N$^g$-nitro of an arginine side chain.

The reagent is prepared by the reaction of BBr$_3$ and CF$_3$COOH in dichloromethane at 0° C. The reagent is also commercially available. Generally, the N$^g$-nitro compound is treated with boron tris(trifluoroacetate) in trifluoroacetic acid at 0° C. See, e.g., Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The N$^g$ nitro compound is treated with titanium trichloride in aqueous methanol containing an ammonium acetate buffer followed by exposure of the reaction mixture to air or dimethyl sulfoxide. Freidinger, R. M., Hirschmann, R., and Veber, D. F., *J. Org. Chem.*, 43, 4800 (1978).

3. Selection of Preferred Compounds

The compounds of the present invention are screened for their ability to inhibit some or all of thrombin, factor Xa, plasmin, recombinant tissue plasminogen activator (rt-PA), activated protein C(aPC), chymotrypsin, and trypsin as set forth below. Certain of the preferred compounds are distinguished by their ability to inhibit thrombin, while not substantially inhibiting some or all of plasmin, tissue plasminogen activator (t-PA), activated protein C(aPC), chymotrypsin, and trypsin. With respect to thrombin and the other enzymes and as used herein, the term "not substantially inhibiting" means that the $IC_{50}$ (or $K_i$) for plasmin, t-PA, aPC, chymotrypsin, and trypsin for a given compound is greater than or equal to its $IC_{50}$ (or $K_i$, respectively) for thrombin. Preferably the ratio of $IC_{50}$'s for plasmin, and the other enzymes, to $IC_{50}$ for thrombin will be at least about 25 or greater, more preferably about 100 or greater. It is believed that the ability to selectively inhibit thrombin will result in therapeutic benefits to patients.

With respect to compounds within the present invention that inhibit members within the trypsin/chymotrypsin family, including trypsin, chymotrypsin, elastase, and serine proteases involved in the coagulation cascade, "not specifically inhibiting" means the $IC_{50}$ or $K_i$ for the target enzyme is less than or equal to the $IC_{50}$ or $K_i$ for non-target enzymes contacted with the inhibitor.

For screening compounds using these assays, the compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophometrically. The $IC_{50}$ of a compound of the present invention is determined from the rate of substrate turnover caused by the specific enzyme being measured. $IC_{50}$ is the concentration of test compound which gives 50% inhibition of the rate of substrate turnover. Likewise, the $K_i$ of a compound of the present invention is determined from the rate of substrate turnover caused by the specific enzyme being measured at various enzyme concentrations. Example A provides exemplars of in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, t-PA, aPC, chymotrypsin, and trypsin which is about 20 to about 100,000 times greater than its $IC_{50}$ for thrombin. More especially preferred compounds have an $IC_{50}$ for plasmin, t-PA, aPC, chymotrypsin, and trypsin which is about 100 to about 1,000,000 times greater than its $IC_{50}$ for thrombin. In the event that a compound of the present invention has an $IC_{50}$ with respect to plasmin, t-PA, aPC, chymotrypsin, or trypsin which is greater than the highest concentration of compound tested, the highest concentration of compound tested is considered to be the reported $IC_{50}$.

The compounds of the present invention are dissolved in buffer to give solutions containing concentrations such that assay concentrations range from 0 to 100 micromolar. In the assays for factor Xa, thrombin, plasmin, t-PA, aPC, chymotrypsin, and trypsin, a chromogenic synthetic substrate is added to a solution containing test compound and the enzyme of interest, and the residual catalytic activity of that enzyme is determined spectrophotometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. Example A provides an example of the in vitro assays used to select the preferred compounds of the present invention.

Example A provides a method for identifying and selecting compounds of the present invention that inhibit thrombin, plasmin, t-PA, aPC, chymotrypsin and trypsin to a greater extent than they inhibit factor Xa and, thus, have utility as inhibitors of those proteases.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg body weight.

Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility and Methods

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent, inhibit and/or attenuate thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook,* 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of thrombin, and as such, can be incorporated into blood collection tubes to prevent clotting of the mammalian blood drawn into them.

The compounds of the present invention are used alone, in combination with other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing, inhibiting and/or attenuating thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets capsules or elixirs taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

Certain compounds of the present invention have utility as inhibitors of proteases within the trypsin/chymotrypsin class of enzymes. Members of that class include, but are not limited to, elastase, chymotrypsin, and the serine proteases trypsin, thrombin, factor Xa, and factor VIIa. With respect to the inhibitors within the present invention directed at serine proteases acting within the coagulation cascade, e.g., inhibitors of thrombin, factor Xa and factor Vlla, such have in vitro and in vivo utilities as provided hereinabove for thrombin inhibitors.

Elastase has been implicated in a variety of conditions, including pulmonary hypertension (Rabinovitch, M., *Acta Paediatr. Jpn* 37:657–666 (1995)), idiopathic pulmonary fibrosis, rheumatoid arthritis, adult respiratory distress syndrome, cystic fibrosis, and other inflammatory diseases and conditions (Doring, G., *Am. J. Respir. Crit. Care Med.* 150:S114–S117 (1994)). Inhibition of elastase was shown to prevent or retard progression of pulmonary hypertension (Rabinovitch). Thus, inhibitors of the present invention directed toward elastase are useful as pharmaceutical compositions for the inhibition of elastase in conditions where elastase activity is associated with a pathological condition.

Elevated levels of chymotrypsin and trypsin are associated with the pathological effects resulting from pancreatitis (see U.S. Pat. No. 5,534,498). Animal studies of chemically-induced pancreatitis suggest that the disorder is rooted in the inability of pancreatic acinar cells to excrete digestive proenzymes, resulting in activation of trypsinogen to trypsin by lysosomal hydrolases within the cell. The amount of trypsin produced exceeds protective levels of protease inhibitor normally available.

The elevated levels of trypsin then cause activation of the other digestive enzymes co-localized with trypsin in the lysosome, such as chymotrypsin. The net effect of the enzyme activation is pancreatitis, which is characterized by damage to the pancreas and surrounding tissues from auto-digestion of the cells by the various digestive enzymes. These activated digestive enzymes also cause edema, interstitial hemorrhage, vascular damage, coagulation necrosis, fat necrosis and parenchymal cell necrosis.

Inhibitors of the present invention directed toward either trypsin or chymotrypsin, or other members of the trypsin/chymotrypsin family that contribute to the deleterious effects of pancreatitis, are useful for the prevention and treatment of pancreatitis in mammals.

In addition to the in vivo utilities, inhibitors of the present invention also find utility in vitro. Inhibitors of enzymes within the coagulation cascade are useful inhibitors of blood coagulation in vitro, as described hereinabove. Inhibitors of other enzymes within the trypsin/chymotrypsin family, including trypsin, chymotrypsin, and elastase, are useful reagents in in vitro assays designed to measure the activity of such enzymes.

For instance, to determine or confirm the presence of active trypsin, chymotrypsin, or elastase in a sample, the activity of the enzyme in the sample is determined in the presence and absence of the specific inhibitor (which may be labeled using a radioactive or other detectable label). Lower activity measured in the presence of inhibitor as compared to in the absence of inhibitor demonstrates inhibition of the enzyme and, thus, its presence in the sample.

Similarly, the level of activity of an enzyme present in a sample is determined by adding inhibitor to the sample in a range of titrating doses, and calculating activity of the enzyme at each escalating dose of inhibitor. The concentration of inhibitor that completely inhibits the enzyme in the assay, along with knowledge of the assay parameters and characteristic of enzyme inhibition, allows one to calculate the activity of the enzyme in the sample.

The level of chymotrypsin measured in stool samples in vitro is used as an indicator of pancreatitis (Riedel, L. et al., Gut 32:321–324 (1991); Chari, S., Trop. Gastroenterol., 11:144–147 (1990)). Chymotrypsin inhibitors of the present invention are useful in such assays to evaluate the level of active chymotrypsin in such a sample, according to protocols such as those outlined hereinabove.

An additional use of the inhibitors of the present invention is their use to quench enzymatic reactions effected by the target enzyme. Thus, to control or prevent digestion of a sample with trypsin or chymotrypsin, an inhibitor of trypsin or chymotrypsin, respectively, is added in inhibit the target enzyme and, thus, control or prevent digestion by that enzyme.

Certain compounds of the present invention can also be useful inhibitors of elastase, and are therefore useful pharmaceutical agents for the control of inflammation.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

A. Preparation of Compound 10 (FIG. 1) Examples 1 to 8

Example 1

Preparation of 3-(Hydroxymethyl)-6-methylaniline (2)

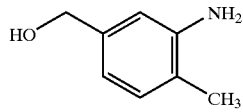

A solution of 3-nitro-4-methylbenzyl alcohol (20 g, 120.0 mmol) (1) in ethyl acetate (500 mL) was stirred at room temperature, while 10% Pd/C (1.0 g) was added in one portion. The resulting suspension was hydrogenated (10 psi) at room temperature under a hydrogen-filled balloon for 48 hours. The catalyst was removed by filtration, and solvent was evaporated under vacuum to give a 1:1 mixture (16.1 g) of the title compound (51%) and a by-product, 2,5-dimethylaniline. This mixture was used in the procedure of Example 2 without further separation. The by-product is removed during the flash column chromatography step of Example 2. For the title compound: MS (electrospray) 138 (M+1); $^1$H NMR (CD$_3$OD) δ 2.14 (s, 3H), 4.54 (s, 2H), 7.12 (d, 1H, J=7.6 Hz), 7.19 (d, 1H, J=7.6 Hz), 7.30 (s, 1H).

Use of a high pressure (30 Psi) of hydrogen or use of alcohol as a solvent in the hydrogenation step led almost exclusively to 2,5-dimethylaniline as a hydrogenation product, in high yield (99%). MS (electrospray) 122 (M+1); $^1$H NMR (CD$_3$OD) δ 2.13 (s, 3H), 2.46 (s, 3H), 6.62 (d, 1H, J=7.6 Hz), 6.72 (d, 1H, J=7.6 Hz), 6.94 (s, 1H).

Example 2

Preparation of 3-(acetoxymethyl)-6-methyl-N-(acetyl)aniline (3)

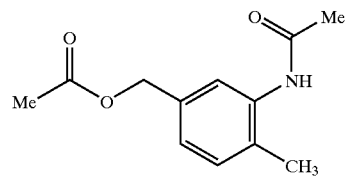

To a solution of an approximately 1:1 mixture of 3-(hydroxymethyl)-6-methylaniline, (8.05 g, 58.8 mmol) (2) and 2,5-dimethylaniline in chloroform (290 mL), was added acetic anhydride (20 mL, 206 mmol) and potassium acetate (20 g, 202 mmol). The resulting mixture was heated at reflux for 2 hours. The mixture was then concentrated and purified by a flash column chromatography (1:1 of hexane-ethyl acetate) to give the title compound (12.02 g, 92%). TLC R$_f$: 0.52 (ethyl acetate); MS (electrospray) 222 (M+1); $^1$H NMR (CDCl$_3$) δ 2.09 (s, 3H), 2.21 (s, 3H), 2.25 (s, 3H), 5.06 (s, 2H), 7.00 (br s, 1H, NH), 7.08 (d, 1H, J=7.6 Hz), 7.18 (d, 1H, J=7.6 Hz), 7.81 (s, 1H).

Example 3

Preparation of 1-Acetyl-6-(acetoxymethyl)indazole (4)

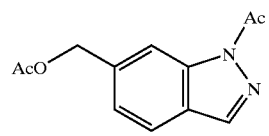

To a suspension of 3-(acetoxymethyl)-6-methyl-N-(acetyl)aniline (10.0 g, 45 mmol) (3) and potassium acetate (8.6 g, 88 mmol) in chloroform (300 mL), was added acetic anhydride (8.3 mL, 88 mmol), isoamylnitrite (35 mL, 300 mmol) and 18-crown-6 (1.5 g, 0.6 mmol) at room temperature. The reaction mixture was heated at reflux for 28 hours. The reaction mixture was diluted with methylene chloride (600 mL) and washed with saturated NaHCO$_3$ aqueous solution (300 mL), water (300 mL) and brine (50 mL). After drying (Na$_2$SO$_4$), the organic solvent was removed under vacuum to give a yellow oil which was purified by a flash chromatography on silica gel (85:15 hexane-ethyl acetate) to yield the title compound (4) (10.01 g, 95%). TLC R$_f$ 0.47 (70:30 of hexane-ethyl acetate); MS (electrospray) 233 (M+1); $^1$H NMR (CDCl$_3$) δ2.10 (s, 3H), 2.78 (s, 3H), 5.27 (s, 2H), 7.36 (d, 1H, J=8.0 Hz), 7.73 (d, 1H, J=8.0 Hz), 8.12 (s, 1H), 8.47 (s, 1H).

Example 4

Preparation of 6-(Bromomethyl)-1H-indazole Hydrogen Bromide (5)

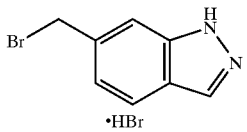

A suspension of 1-acetyl-6-(acetoxymethyl)indazole (9.5 g, 41 mmol) (4) in aqueous hydrobromic acid (48% aqueous solution, 20 mL, 177 mmol) was stirred at room temperature for 46 hours. The solid was collected on a Buchner funnel and dried under vacuum for 12 hours. The filtrate was stirred at room temperature for additional 24 hours and more solid was collected. After drying under vacuum, title compound was obtained as a yellow solid (10.0 g, 84%) which was used as such without further purification. MS (electrospray) 211 (M+1 for $^{79}$Br), 213 (M+1 for $^{81}$Br); $^1$H N MR (CDCl$_3$) δ 4.85 (s, 2H), 7.65 (d, 1H, J=8.4 Hz), 7.78 (d, 1H, J=8.4 Hz), 8.05 (s, 1H), 8.10 (s, 1H).

Example 5

Preparation of 6-(bromomethyl)-1-(2-tetrahydropyranyl)indazole (6)

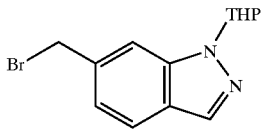

A yellow suspension of 6-(bromomethyl)-1H-indazole hydrogen bromide (9.0 g, 43 mmol) (5) and 3,4-dihydro-2H-pyran (7.2 g, 86 mmol) in THF (200 mL) was heated at reflux for 2 hours. The reaction mixture was additionally stirred at room temperature for 12 hours under nitrogen. The reaction solution was diluted with methylene chloride (500 mL), washed with saturated NaHCO$_3$, water and brine. After drying (MgSO$_4$), the solvent was removed under vacuum to give a yellow oil. Flash chromatography yielded the title compound (6.6 g, 72%). TLC R$_f$ 0.52 (80:20 of hexane-ethyl acetate); MS (electrospray) 295, 297 (M+1); $^1$H N MR (CDCl$_3$) δ 1.57–1.84 (m, 3H), 2.16 (m, 2H), 2.55 (m, 1H), 3.75 (m, 1H), 4.01 (m, 1H), 4.65 (s, 2H), 5.71 (d, 1H, J=9.2 Hz), 7.44 (d, 1H, J=8.8 Hz), 7.59 (d, 1H, J=8.8 Hz), 7.73 (s, 1H), 8.00 (s, 1H).

Example 6

Preparation of 6-(Azidomethyl)-1-(2-tetrahydropyranyl)indazole (7)

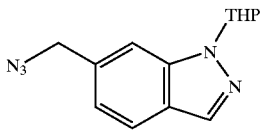

To a solution of 6-(bromomethyl)-1-(2-tetrahydropyranyl)indazole (4.0 g, 14 mmol) (6) in DMF (30 mL) was added sodium azide (6 g, 92 mmol) in one portion. The suspension was heated at 90° C. for 30 minutes and a yellow solution was formed. After cooling to room temperature, the reaction mixture was poured into water (100 mL) and extracted with ether (2×150 mL). Combined organic layers were washed with brine then dried (MgSO$_4$). Evaporation of solvent gave an yellow oil which was purified by column chromatography to yield title compound (2.91 g, 83%). TLC R$_f$ 0.31 (70:30 of hexane-ethyl acetate); MS (electrospray) 258 (M+1); $^1$H NMR (CDCl$_3$) δ 1.75 (m, 3H), 2.10 (m, 2H), 2.55 (m, 1H), 3.72 (m, 1H), 4.01 (m, 1H), 4.48 (s, 2H), 5.73 (dd, 1H, J=8.2, 2.8 Hz), 7.12 (dd, 1H, J=8.2, 0.8 Hz), 7.55 (s, 1H), 7.71 (d, 1H, J=8.2 Hz), 8.02 (s, 1H).

Example 7

Preparation of 6-(Aminomethyl)-1-(2-tetrahydropyranyl)indazole (8)

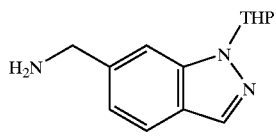

A solution of LiAlH$_4$ (9 mL, 9 mmol, 1.0 M) in THF was added dropwise to a yellow solution of 6-(azidomethyl)-1-(2-tetrahydropyranyl)indazole (2.4 g, 9 mmol) (8) in THF (30 mL) at 0° C. After stirring at 0° C. for 1 hour, NaOH (1.0 m, 1.5 mL) was added. The reaction mixture was allowed to warm to room temperature. Ethyl acetate (100 mL) was added, and the suspension was filtered through (Celite). The filter cake was washed with an addition portion of ethyl acetate (40 mL). Combined organic layers were evaporated under vacuum to five essentially pure amine (2.1 g, 97%). MS (electrospray) 232.5 (M+1); $^1$H NMR (CDCl$_3$) δ 1.67 (m, 3H), 2.01 (m, 2H), 2.48 (m, 1H), 3.85 (m, 1H), 3.94 (m, 1H), 5.75 (d, 1H, J=9.4 Hz), 7.14 (d, 1H, J=8.4 Hz), 7.62 (s, 1H), 7.62 (d, 1H, J=8.4 Hz), 7.93 (s, 1H)

Example 8

Preparation of 3-(2-Phenethylamino)-6-methyl-1-(6-methylcarboxamidomethyl-indazolyl)pyrazinone Trifluoroacetate Salt (10)

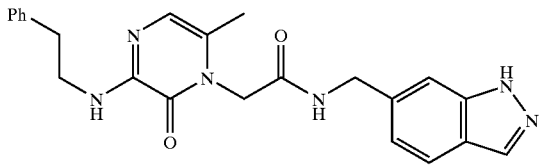

A solution of 6-(Aminomethyl)-1-(2-tetrahydropyranyl) indazole (8, 155 mg, 0.67 mmol), 3-(2-phenethylamino)-6-methyl-1-carboxymethylpyrazinone (9) (192 mg, 0.67 mmol), EDC (191 mg, 1.0 mmol), HOAt (136 mg, 1.0 mmol), and DIEA (0.6 mL, 3.4 mmol) in DMF was stirred at room temperature for 16 hours. The solvent was removed under vacuum to give a yellow residue which was purified by a flash chromatography (4% methanol in methylene chloride) to yield a THP protected intermediate (254 mg, 75%). This intermediate was further treated with hydrogen chloride in dioxane (Aldrich, 4M, 2 mL) at 60° C. for 1 hour. The reaction mixture was purified on a reversed phase preparatory HPLC eluting with acetonitrile-0.1% of TFA in water. Those fractions of >95% purity were combined and concentrated. Lyophilization gave the title compound (0.1 g, 47%) as a white solid. MS (electrospray): 417 (M+1).

Figure 2:
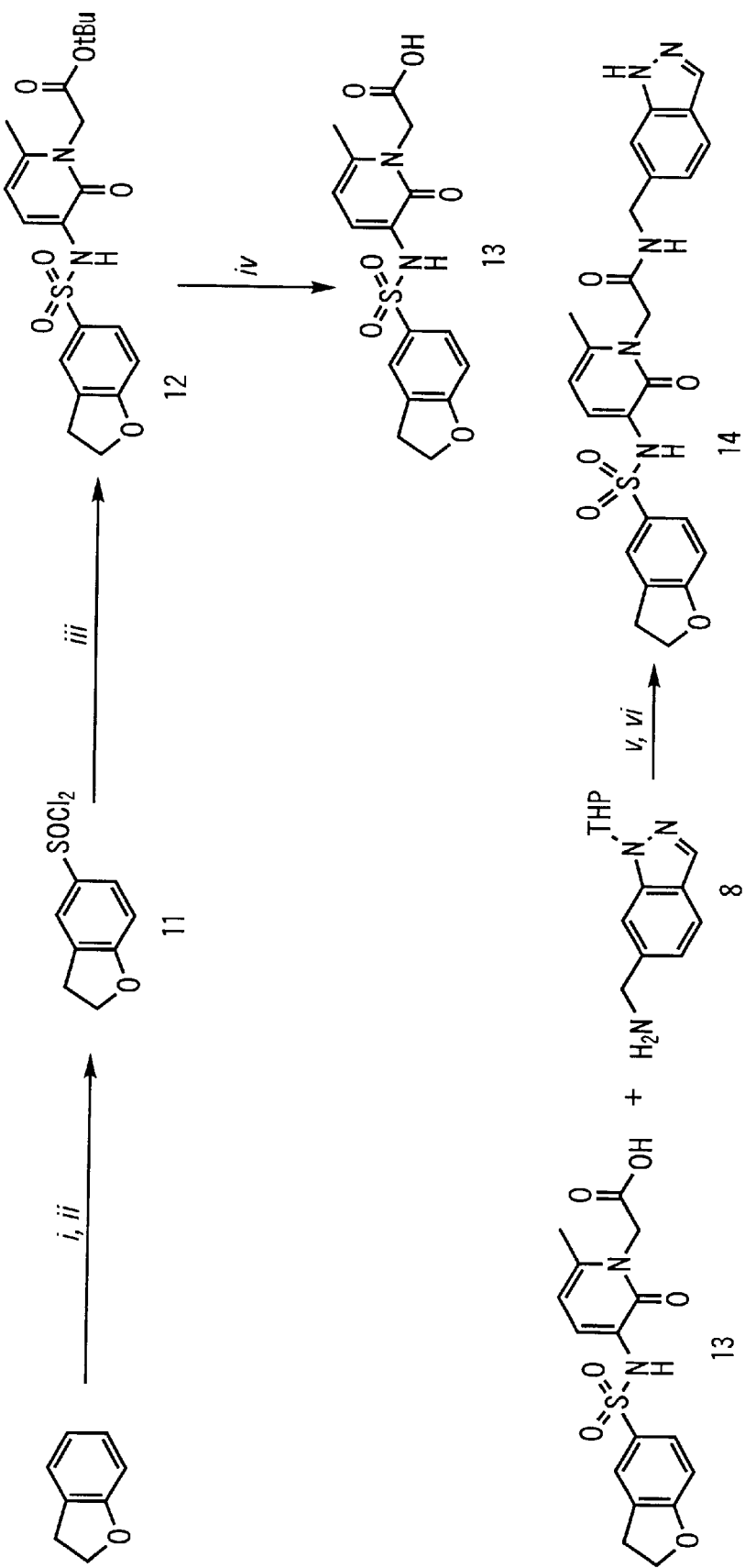
FIG. 2 depicts a reaction scheme for the synthesis of a compound having thrombin inhibitory activity. In this figure "i" through "vi" are defined as follows: i) SO$_3$-DMF, DCE, reflux 1 hour; ii) SOCl$_2$, reflux 1 to 3 hours, 94% yield; iii) 3-amino-6-methyl-1-tert-butyl-methylenecarboxy-2-pyridinone, TEA, acetonitrile, room temperature 16 hours, 64% yield; iv) 4M HCl, dioxane, 0° C., 8 hours, quantitative yield; v) EDC, HOAt, DIEA, DMF, room temperature 16 hours; vi) 4M HCl in dioxane, 60° C. 1 hour, 6% yield. These procedures are more fully described in Examples 9 to 12.

B. Preparation of Compound 14 (FIG. 2) Examples 9 to 12

Example 9

Preparation of 5-chlorosulfonyl-2,3-dihydrobenzo[b]furan (11)

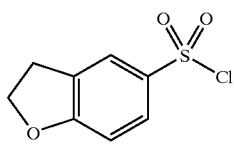

2,3-Dihydrobenzo[b]furan (Aldrich, 5.6 mL, 50 mmol) was added to a suspension of sulfur trioxide-dimethylformamide complex (Aldrich, 9.2 g, 60 mmol) in 1,2-dichloroethane (Aldrich, 20 mL). After being heated at 80° C. for 1 hour, the reaction mixture was cooled to room temperature, and thionyl chloride (Aldrich, 4.5 mL, 57 mmol) was introduced. The reaction mixture was then heated at 70° C. for 3 hours. After cooling to room temperature, the reaction mixture was poured into ice water (100 mL) and extracted with ether (3×30 mL). Combined organic layers were washed with brine, then dried (MgSO$_4$). Removal of solvent under vacuum yielded a light yellow solid (10.2 g, 94%). TLC R$_f$ 0.45 (9:1 of hexane-ethyl acetate); MS (electrospray) 219 (M+1); $^1$H NMR (CDCl$_3$) δ 3.35 (t, 2H, J=7.2 Hz), 4.78 (t, 2H, J=7.2 Hz), 6.92 (d, 1H, J=3.1 Hz), 7.82 (s, 1H), 7.83 (d, 1H, J=3.1 Hz).

Example 10

Preparation of (12)

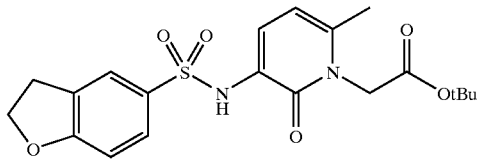

A solution of 5-chlorosulfonyl-2,3-dihydrobenzo[b]furan (11, 1.8 g, 8.3 mmol), 3-amino-6-methyl-1-tert-butylmethylenecarboxy-2-pyridinone (synthesized based on a literature procedure: Sanderson, P. E. J., et al., *J. Med. Chem.* 1998, 41, 4466–4474; 1.5 g, 6.4 mmol ), and triethylamine (Aldrich, 4.5 mL, 32 mmol) in acetonitrile (20 mL) was stirred at room temperature for 16 hours. The solvent was removed under vacuum and the residue was purified by flash chromatography (40:60 of hexane-ethyl acetate) to give the title compound as a white solid (1.7 g, 64%). MS (electrospray) 421 (M+1).

Example 11

Preparation of (13)

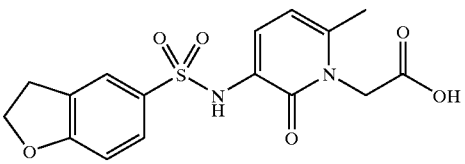

A solution of hydrogen chloride in dioxane (Aldrich, 4.0M, 10 mL) was added to a solution of compound 12 (750 mg, 1.8 mmol) in dioxane (10 mL), and the mixture was stirred at room temperature for 4 hours. The solvent was removed under vacuum to give the title compound (590 mg, 100%), which was used in the next step without further purification. MS(electrospray) 365 (M+1).

Example 12

Preparation of (14)

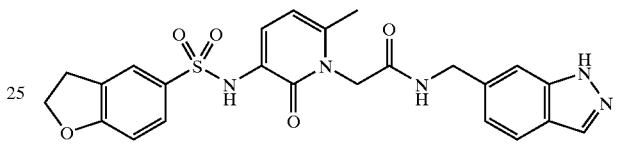

A solution of 6-(Aminomethyl)-1-(2-tetrahydropyranyl) indazole (8, 116 mg, 0.5 mmol), compound 13 (200 mg, 0.55 mmol), EDC (143 mg, 0.75 mmol), HOAt (100 mg, 0.75 mmol) and DIEA (0.5 mL, 2.5 mmol) in DMF was stirred at room temperature for 16 hours. The solvent was removed under vacuum to give a yellow residue which was purified by a flash chromatography (4% methanol in methylene chloride) to yield a THP protected intermediate (170 mg, 59%). This intermediate was further treated with hydrogen chloride in dioxane (Aldrich, 4M, 2 mL) at 60° C. for 1 hour. The reaction mixture was purified on a reversed phase preparatory HPLC eluting with acetonitrile-0.1% of TFA in water. Lyophilization under high vacuum afforded a white solid (9 mg, 6%). HPLC retention, 15.5 minutes; C18 column 5–75% acetonitrile in water over 25 minutes, 1.0 mL/min. MS (electrospray) 494 (M+1); $^1$H NMR (DMSO-d$_6$): δ 2.20 (s, 3H), 3.15 (t, 2H, J=7.2 Hz), 4.40 (s, 2H),4.58 (t, 2H, J=7.2 Hz), 4.68 (s, 2H), 6.10 (m, 1H), 6.81 (d, 1H, J=7.3 Hz), 7.00 (d, 1H, J=7.3 Hz), 7.22 (m, 1H), 7.42 (s, 1H), 7.60 (d, 1H, J=7.3 Hz), 7.63 (m, 2 H), 8.02 (s, 1H), 8.78 (m, 1H), 9.00 (m, 1H).

Figure 3:
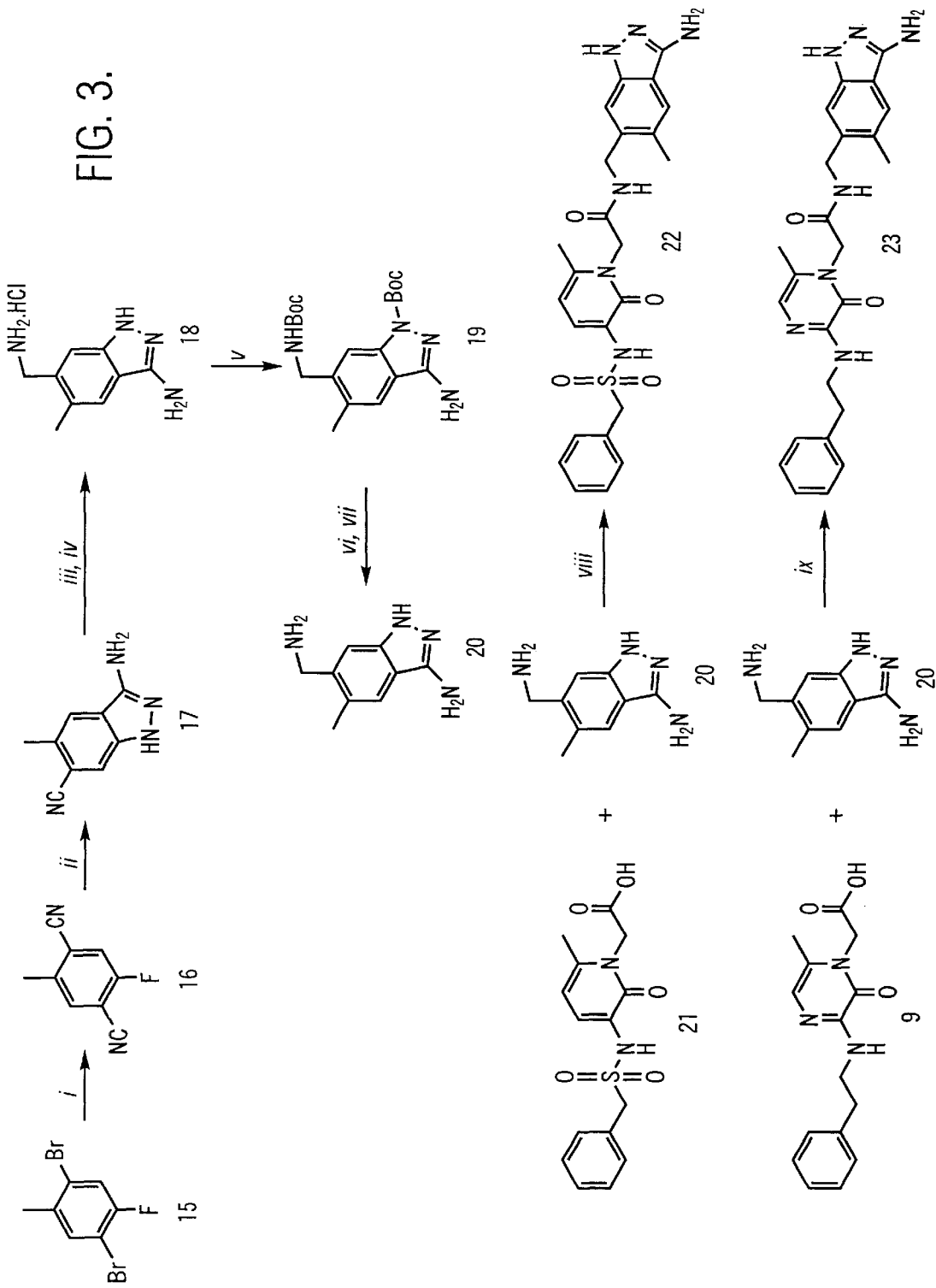
FIG. 3 depicts reaction schemes for the synthesis of certain compounds having thrombin inhibitory activity. In this figure "i" through "ix" are defined as follows: 1) CuCN, DMF, reflux 6 hours, 76% yield; ii) NH$_2$NH$_2$, ethanol, reflux under N$_2$ 17 hours, 91% yield; iii) B$_2$H$_6$/THF, 0° C. to room temperature 15 hours; iv) 6N HCl, water and methanol, room temperature 6 hours neutralize with NaOH; v) Boc$_2$O in THF, methanol, room temperature 15 hours, 60% yield; vi) 2N HCl, methanol, dioxane, room temperature 4 hours; vii) OH$^-$ resin; viii) HOAt, EDC, DMF, room temperature 15 hours; and ix) HOAt, EDC, DMF, room temperature 15 hours. These procedures are more fully described in Examples 13 to 18.

C. Preparation of Compound 22 and 23 (FIG. 3) Examples 13 to 18

Example 13

Preparation of (16)

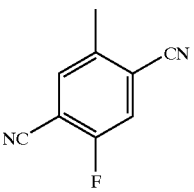

To a solution of 2,5-dibromo-4-fluorotoluene (Aldrich, 50.00 g, 186.6 mmol) in DMF (100 mL) was added CuCN (Aldrich, 33.40 g, 373.2 mmol) and the mixture was refluxed under nitrogen for 6 hours. After cooling to room temperature, the mixture was partitioned between 10% KCN water solution and ether. The water layer was extracted with ether, and the combined extracts were washed by brine twice and dried over $Na_2SO_4$. After filtration and evaporation, the crude product was purified on a silica gel column eluting with hexane-EtOAc (from 95:5 to 90:10) to provide the title compound as a yellow-green solid (22.66 g, 76% yield). TLC $R_f$ 0.63 (hexane:EtOAc 4:1); m.p. 141–143° C.; $^1H$ NMR (400 MHz, $CDCl_3$): δ 7.60 (d, 1H, J 6.1 Hz), 7.47 (d, 1H, J 8.2 Hz), 2.58 (s, 3H).

Example 14

Preparation of (17)

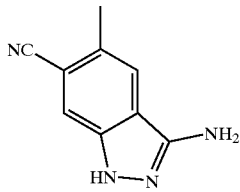

A mixture of 2,5-dicyano-4-fluorotoluene (compound 16, 10.95 g, 68.4 mmol) and anhydrous hydrazine (4.5 mL, 143.6 mmol) in anhydrous ethanol (342 mL) was refluxed under nitrogen for 17 hours. After cooling down to the room temperature, a yellow crystalline solid product precipitated out. The solid was filtered, washed by ethanol, and dried under high vacuum to provide yellow crystalline product (4.26 g). The filtrate was evaporated and purified on a silica gel column eluting with dichloromethane and 5% methanol in dichloromethane to provide additional product (6.47 g). Total 10.73 g of yellow crystalline solid product (17) was obtained (91% yield). TLC $R_f$ 0.36 (5% MeOH in $CH_2Cl_2$); $^1H$ NMR (400 MHz, $CDCl_3$): δ 9.05 (bs, 1H), 7.64 (s, 1H), 7.48 (s, 1H), 4.12 (bs, 2H), 2.61 (s, 3H)

Example 15

Preparation of (18) and (19)

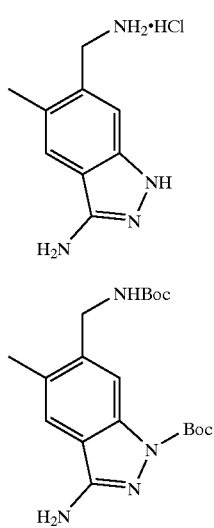

To a solution of 1M borane in THF (40 mL, 40 mmol), was added a solution of compound 17 (0.80 g, 4.65 mmol) in anhydrous THF (15 mL) at 0° C. under nitrogen. The reaction mixture was stirred from 0° C. to room temperature under nitrogen for 15 hours. To the reaction solution were added 6N HCl (30 mL) slowly, followed by water (30 mL) and methanol (200 mL). The mixture was stirred at room temperature for 6 hours. Most of THF and methanol were evaporated to give the intermediate 18, which was neutralized to pH ~13 by NaOH, and then adjusted to pH ~11 by $NaHCO_3$.

A solution of $(Boc)_2O$ in THF (15 mL, 15 mmol), was added to the above solution of 18 in THF and methanol, and the reaction mixture was stirred at room temperature for 15 hours. The product was extracted with dichloromethane, and the combined extracts were washed by brine and dried over $Na_2SO_4$. After filtration and evaporation, the product was purified on a silica gel column eluting with 1% and 2% methanol in dichloromethane to provide an off-white product (compound 19, 1.05 g, 60% yield). TLC $R_f$ 0.88 (5% MeOH in $CH_2Cl_2$); $^1H$ NMR (400 MHz, $CDCl_3$): δ 7.27 (s, 1H), 7.08 (s, 1H), 5.90 (bs, 2H), 4.76 (bs, 1H), 4.29 (bd, 2H, J 5.8 Hz), 2.25 (s, 3H), 1.62 (s, 9H), 1.46 (s, 9H).

Example 16

Preparation of (20)

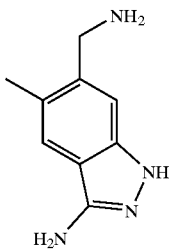

Compound 19 (795 mg, 2.11 mmol) was dissolved in 2 M HCl methanol/dioxane (1:1) solution (20 mL). The reaction solution was stirred at room temperature for 4 hours. After evaporation of solvent, the residue was suspended in methanol (30 mL), and to the mixture was added hydroxide form basic resin (AG 1-X8 Resin from Bio-Rad Laboratories) to make a clear solution and adjust the pH ~11. The resin was filtered and washed with methanol thoroughly. The methanol solution was evaporated and the residue was dried under high vacuum to provide the free amine compound 20 as a white solid (395 mg, 100% yield). $^1H$ NMR (400 MHz, $CD_3OD$): δ 7.44 (s, 1H), 7.26 (s, 1H), 3.90 (s, 2H), 2.37 (s, 3H), 1.62 (s, 9H).

Example 17

Preparation of (22)

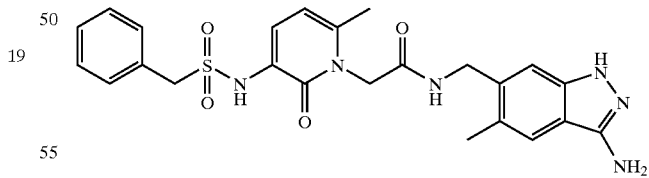

To a solution of 3-benzylsulfonylamino-6-methyl-1-methylenecarboxy-2-pyridinone (21, 430.6 mg, 1.28 mmol, synthesized based on a literature procedure: Sanderson, P. E. J., et al., *J. Med. Chem.* 1998, 41, 4466–4474) in DMF (6 mL), were added HOAt (190.5 mg, 1.40 mmol), EDC (268.4 mg, 1.40 mmol) and compound 20 (225 mg, 1.28 mmol). The mixture was stirred under nitrogen at room temperature for 15 hours, and then poured into water (80 mL). The product was extracted with EtOAc, and the combined extracts were washed by $NaHCO_3$ and dried over $Na_2SO_4$.

43

After filtration and evaporation, the residue was purified on a reversed phase preparatory HPLC eluting with an acetonitrile-0.1% TFA in water system. The pure fractions were concentrated and lyophilized to provide a white solid product (compound 22, 6.6 mg, 90% purity). MS: m/e 495.2 (M+H)+; 1H NMR (400 MHz, CD3OD): δ 7.65 (s, 1H), 7.46 (s, 1H), 7.33 (d, 1H, J 7.6 Hz), 7.22–7.11 (m, 5H), 6.17 (d, 1H, 7.6 Hz), 4.89 (s, 2H), 4.50 (s, 2H), 4.38 (s 2H), 2.40 (s, 3H), 2.36 (s, 3H).

Example 18

Preparation of (23)

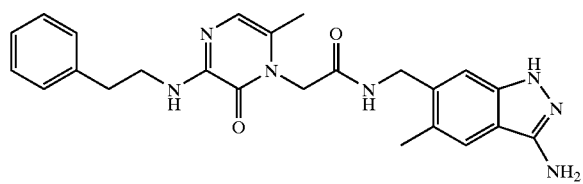

To a solution of 3-(2-phenethylamino)-6-methyl-1-methylenecarboxy-2-pyridinone (273.0 mg, 0.95 mmol) in DMF (5 mL) were added HOAt (142.2 mg, 1.04 mmol), EDC (268.4 mg, 1.04 mmol) and compound 20 (168 mg, 0.95 mmol). The mixture was stirred under nitrogen at room temperature for 15 hours, and then poured into water (80 mL). The product was extracted with EtOAc, and the combined extracts were washed by NaHCO3 and dried over Na2SO4. After filtration and evaporation, the residue was purified on a reversed phase preparatory HPLC eluting with acetonitrile-0.1% TFA in water system. The pure fractions were concentrated and lyophilized to provide a white solid product (Compound 23, 10.0 mg, 90% purity). MS: m/e 223.6 (M+2H)2+/2, 446.2 (M+H)+; 1H NMR (400 MHz, CD3OD) δ 7.68 (s, 1H), 7.36 (s, 1H), 7.28–7.17 (m, 5H), 6.56 (s, 1H), 4.81 (s, 2H), 4.52 (s, 2H), 3.64 (dd, 2H, J 7.0 Hz, J 7.6 Hz), 2.96 (dd, 2H, J 7.0 Hz, J 7.6 Hz), 2.41 (s, 3H), 2.19 (s, 3H).

Figure 4:
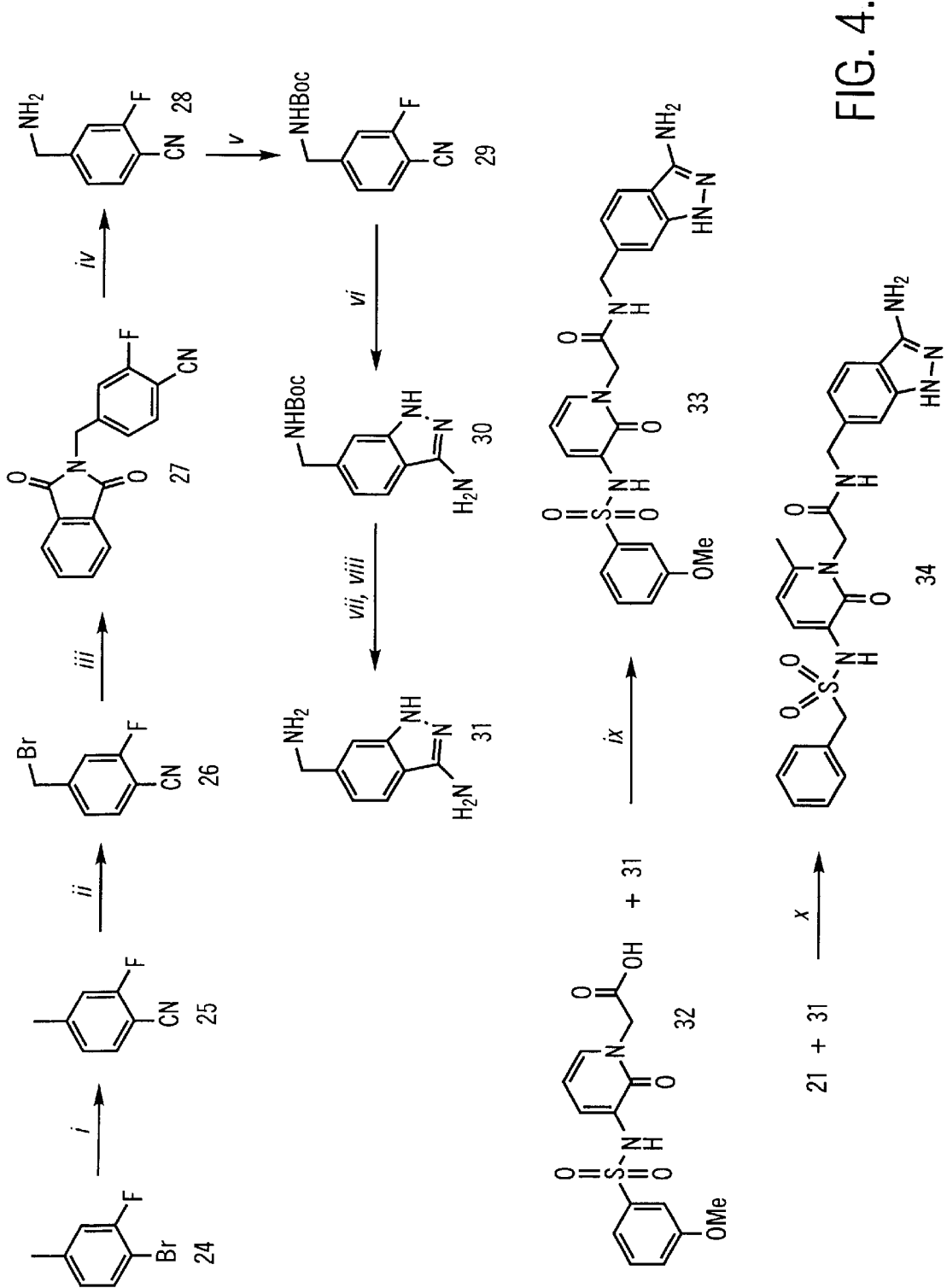
FIG. 4 depicts reaction schemes for the synthesis of certain compounds having thrombin inhibitory activity. In this figure, "i" through "x" are defined as follows: i) CuCN, DMF, reflux 5 hours; ii) NBS, AIBN, CCl$_4$, reflux 4.5 hours; iii) phthalimide, Cs$_2$CO$_3$, DMF, room temperature 0.5 hour; iv) hydrazine, n-butanol, reflux 5 minutes; v) Boc$_2$O, DCM, room temperature 1 hour; vi) hydrazine, n-butanol, reflux 22 hours; vii) 2M HCl in dioxane, room temperature 0.5 hour; viii) OH$^-$ resin; ix) HOAt, EDC, DMF, room temperature 15 hours; and x) HOAt, EDC, DMF, room temperature 15 hours. These procedures are more fully described in Examples 19 to 26.

D. Preparation of Compounds 33 and 34 (FIG. 4) Examples 19 to 26

Example 19

Preparation of (25)

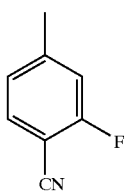

To a solution of 4-bromo-3-fluorotoluene (Aldrich, 50.00 g, 264.5 mmol) in DMF (100 mL) was added CuCN (Aldrich, 23.69 g, 264.5 mmol). The mixture was refluxed under nitrogen for 5 hours. After cooling to the room temperature, CuBr precipitated out. The mixture was diluted with ether (500 mL), filtered, and CuBr solid was washed by ether. The combined ether solution was washed with brine three times and dried over MgSO4. After filtration, evaporation and high vacuum dry, an off-white solid product was obtained (32.50 g, 94% yield). TLC Rf 0.54 (hexane:EtOAc 5:1), 1H-NMR (400 MHz, CDCl3): δ 7.48 (dd, 1H, J 8.2 Hz, J 6.1 Hz), 7.05 (d, 1H, J 8.2 Hz), 7.01 (d, 1H, J 10.1 Hz), 2.42 (s, 3H).

Example 20

Preparation of (26)

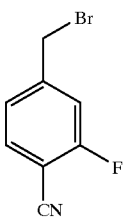

To a solution of 4-cyano-3-fluorotoluene (Compound 25, 28.51 g, 211.0 mmol) in carbon tetrachloride (Aldrich, 844 mL) were added NBS (Aldrich, 41.31 g, 162.8 mmol) and AIBN (Aldrich, 2.43 g, 14.8 mmol). The mixture was degassed with nitrogen for three times, and then was refluxed at 85° C. for 4.5 hours. After standing at room temperature overnight, the mixture was filtered. The solid by-product was washed with CCl4. The filtrate was evaporated and purified on a silica gel column, eluting with hexane-EtOAc (from 20:1 to 5:1). The title product (24.54 g, 54% yield) was obtained as a colorless liquid which solidified after standing at room temperature. TLC Rf 0.44 (hexane:EtOAc 10:1), 1H-NMR (400 MHz, CDCl3): δ 7.61 (dd, 1H, J 7.9 Hz, J 6.7 Hz), 7.28 (d, 1H, J 6.7 Hz), 7.27 (d, 1H, J 7.0 Hz), 4.44 (s, 2H).

Example 21

Preparation of (27)

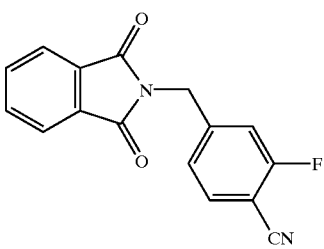

To a solution of α-bromo-4-cyano-3-fluorotoluene (compound 26, 7.67 g, 35.83 mmol) in DMF (250 mL) were added phthalimide (Aldrich, 8.74 g, 59.44 mmol) and Cs2CO3 (Aldrich, 35.21 g, 108.1 mmol). The reaction mixture was stirred at room temperature under nitrogen for half an hour, and then poured into water (1 L). The product precipitated out of the water solution. After filtration, washing by water (500 mL) and methanol (100 mL), and high vacuum dry, the product was obtained as a white crystalline solid (9.15 g, 91% yield). 1H-NMR (400 MHz, CDCl3) δ 7.88 (dd, 2H, J 3.05 Hz, J 5.2 Hz), 7.76 (dd, 2H, J 3.05 Hz, J 5.5 Hz), 7.58 (dd, 2H, J 7.9 Hz, J 6.4 Hz), 7.31 (d, 2H, J 7.9 Hz), 7.27 (d, 2H, J 12.5 Hz), 4.87 (s, 2H).

Example 22

Preparation of (29)

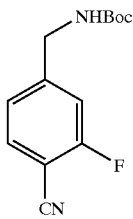

To a solution of compound 27 (8.50 g, 30.33 mmol) in n-butanol (Aldrich, 150 mL) was added anhydrous hydrazine (Aldrich, 2.95 mL, 94.02 mmol). The mixture was refluxed under nitrogen for 5 minutes. A voluminous precipitate formed which was removed by filtering out after cooling the mixture to the room temperature. n-Butanol was removed by evaporation. The residue (compound 28) was dissolved in dichloromethane; (Boc)$_2$O (7.28 g, 33.36 mmol) was added and the resulting mixture was stirred at room temperature for 1 hour. After evaporation of solvent, the residue was purified on a silica gel column eluting with hexane-EtOAc (from 5:1 to 3:1) to provide compound 29 as a white crystalline solid (7.52 g, 99% yield). TLC R$_f$ 0.37 (hexane:EtOAc 3:1), $^1$H-NMR (400 MHz, CDCl$_3$): δ 7.57 (dd, 1H, J 7.6 Hz, J 6.7 Hz), 7.16 (d, J 7.6 Hz, 1H), 7.14 (d, 1H, J 9.8 Hz), 5.01 (bs, 1H), 4.36 (bd, 2H, J 5.8 Hz), 1.46 (s, 9H).

Example 23

Preparation of (30)

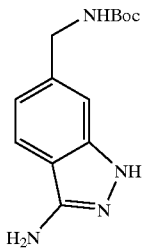

To a solution of compound 29 (7.52 g, 30.3 mmol) in n-butanol (150 mL) was added hydrazine (Aldrich, 2.86 mL, 91.0 mmol). The reaction mixture was refluxed under nitrogen for 22 hours. After evaporation of the solvent, the residue was purified on a silica gel column eluting with 5% methanol in dichloromethane to provide product compound 30 (5.13 g, 64% yield) as a light yellow crystalline solid. TLC R$_f$ 0.33 (5% MeOH in CH$_2$Cl$_2$), $^1$H-NMR (400 MHz, CDCl$_3$) δ 8.85 (bs, 1H), 7.51 (d, 1H, J 8.2 Hz), 7.22 (s, 1H), 7.10 (d, 1H, J 8.2 Hz), 4.91 (bs, 1H), 4.41 (bd, 2H, J 5.5 Hz), 4.08 (bs, 2H), 1.47 (s, 9H).

Example 24

Preparation of (31)

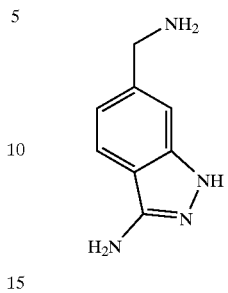

Compound 30 (5.13 g, 19.6 mmol) was dissolved in a 2M HCl dioxane solution (60 mL). The reaction mixture was stirred at room temperature for half an hour. After evaporation of solvent, a light yellow solid was obtained which was suspended in methanol (300 mL). To the mixture was added hydroxide form basic resin (AG 1-X8 Resin from Bio-Rad Laboratories) to adjust the pH to ~10. After filtration, the resin was washed by methanol thoroughly. The methanol solution was evaporated and the residue was dried under high vacuum to provide compound 31 as a light yellow solid (3.17 g, 100% yield). $^1$H NMR (400 MHz, D$_2$O) δ 7.58 (d, 1H, J 8.2 Hz), 7.25 (s, 1H), 6.99 (d, 1H, J 8.2 Hz), 3.85 (s, 2H).

Example 25

Preparation of (33)

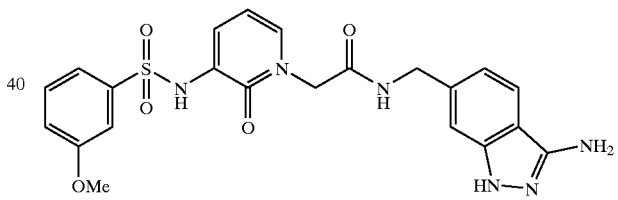

To a solution of acid 32 (676.7 mg, 2.00 mmol) (see, e.g., U.S. Pat. No. 5,658,930 for a description of preparation of this compound) in DMF (8 mL), were added HOAt (326.7 mg, 2.40 mmol), EDC (474.5 mg, 2.40 mmol) and compound 31 (454.2 mg, 2.80 mmol). The mixture was stirred under nitrogen at room temperature for 15 hours, and then poured into water (125 mL). The resulting mixture was extracted with EtOAc, and the combined extracts were washed with saturated aqueous NaHCO$_3$ and dried over Na$_2$SO$_4$. After filtration and evaporation, the crude product was purified by reversed phase preparatory HPLC, eluting with an acetonitrile-0.1% TFA in water system. The pure fractions were concentrated and lyophilized to provide the title compound as a white solid (488 mg, 99% purity, 51% yield). MS: m/e 483.2 (M+H)$^+$, 965.0 (2M+H)$^+$; $^1$H-NMR (400 MHz, CD$_3$OD): δ 7.79 (d, 1H, J 8.5 Hz), 7.54 (d, 1H, J 5.8 Hz), 7.53–7.29 (m, 5H), 7.26 (d, 1H, J 6.7 Hz), 7.12 (d, 1H, J 8.5 Hz), 7.05 (dt, 1H, J 7.9 Hz, J 1.5 Hz), 6.26 (dd, 1H, J 6.7 Hz, J 7.6 Hz), 4.62 (s, 2H), 4.48 (s, 2H), 3.73 (s, 3H).

Example 26

Preparation of (34)

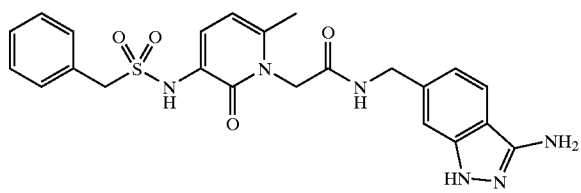

To the solution of acid 31 (200 mg, 0.60 mmol) in DMF (3 mL), were added HOAt (Aldrich, 97 mg, 0.71 mmol), EDC (Aldrich, 137 mg, 0.71 mmol) and compound 21 (96.4 mg, 0.60 mmol). The mixture was stirred under nitrogen at room temperature for 15 hours, poured into a 1:1 solution of water and acetonitrile, and purified on a reversed phase preparatory HPLC eluting with an acetonitrile-01.% TFA/water system. The pure fractions were concentrated and lyophilized to provide the final product compound 34 as a white solid (70.0 mg, 99% purity, 35% yield). MS: m/e 481.0 (M+1); $^1$H-NMR (400 MHz, CD$_3$OD): δ 8.85 (m, 1H), 7.82 (d, 1H, J=7.5 Hz), 7.34 (m, 7H), 6.18 (d, 2H J=7.5 Hz), 4.80 (s, 2H), 4.56 (d, 1H, J=5.7 Hz), 4.40 (s, 1H), 2.32 (s, 3H).

Figure 5:
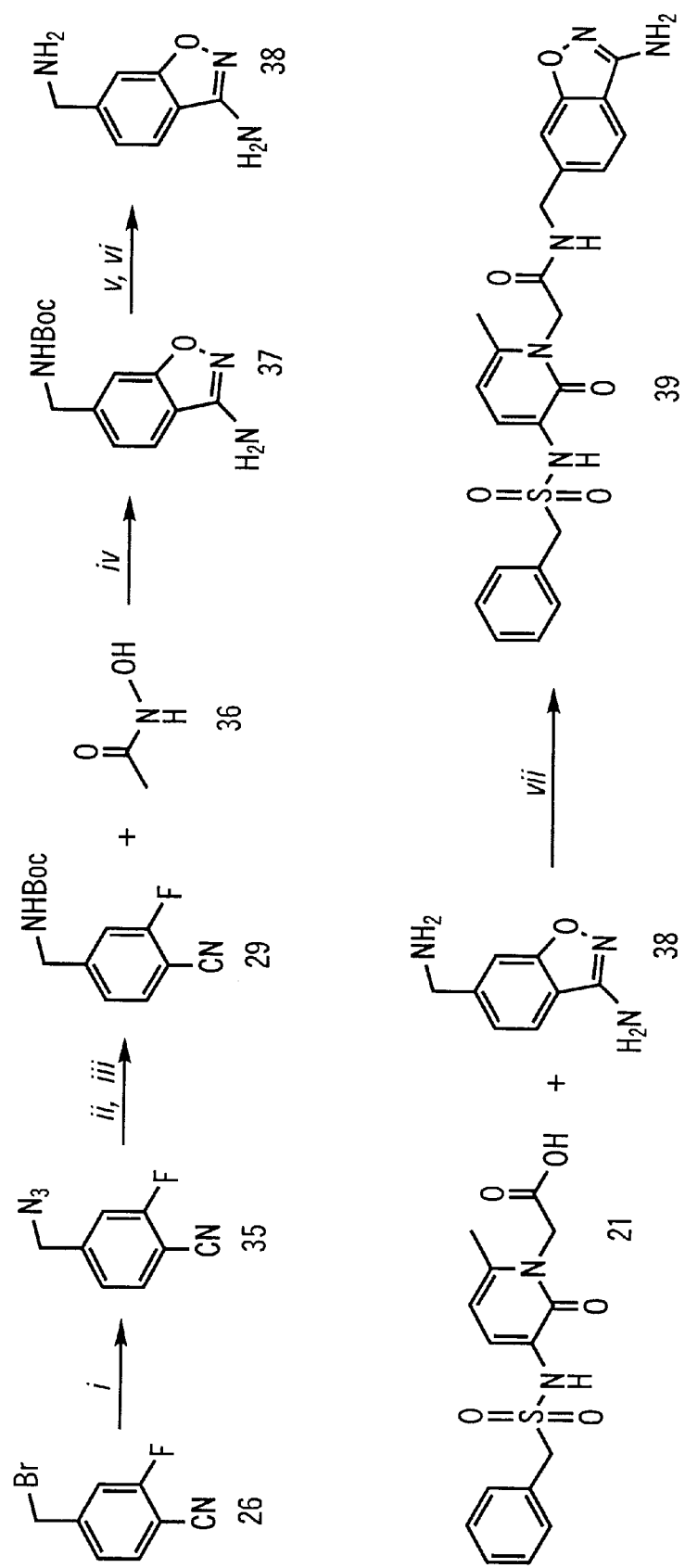
FIG. 5 depicts a reaction scheme for the synthesis of a compound having thrombin inhibitory activity. In this figure "i" through "vii" are defined as follows: i) NaN$_3$, DMF, room temperature 15 hours; ii) Ph$_3$P, THF/H$_2$O, room temperature 15 hours; iii) Boc$_2$O in DMF, room temperature overnight; iv) t-BuOK, DMF, room temperature 30 minutes, add 29, room temperature 15 hours, 70° C., 24 hours; v) 2N HCl, methanol/dioxane, room temperature 0.5 hour; vi) OH$^-$ resin; and vii) HOAt, EDC, DMF, room temperature 15 hours. These procedures are more fully described in Examples 27 to 30.

E. Preparation of Compound 39 (FIG. 5) Examples 27 to 30

Example 27

Preparation of (35)

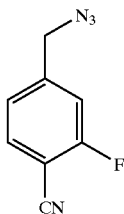

To a solution of α-bromo-4-cyano-3-fluorotoluene (compound 26, 10.00 g, 46.72 mmol) in DMF (100 mL) was added sodium azide (Aldrich, 3.64 g, 56.06 mmol). The reaction mixture was stirred at room temperature under nitrogen for 15 hours, and then poured into water (500 mL). The product was extracted with ether and the combined extracts were washed with brine three times, and dried over Na$_2$SO$_4$. After filtration, evaporation and high vacuum dry, a light yellow crystalline product (compound 37, 8.22 g, 100% yield) was obtained which was used for the next step without further purification. TLC R$_f$ 0.72 (hexane:EtOAc 5:1), $^1$H-NMR (400 MHz, CDCl$_3$): δ 7.64 (dd, 1H, J 7.6 Hz, J 6.7 Hz), 7.22 (d, 1H, J 6.7 Hz), 7.21 (d, 1H, J 10.4 Hz), 4.47 (s, 2H).

Example 28

Preparation of (37)

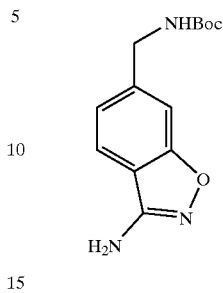

To a solution of α-azido-4-cyano-3-fluorotoluene (compound 35, 1.75 g, 10 mmol) in THF (46 mL) and water (2 mL), was slowly added triphenylphosphine (Aldrich, 2.89 g, 11 mmol). The mixture was stirred at room temperature for 15 hours, and then the solvents were evaporated. The residue was dissolved in 0.25 M HCl (75 mL, 18.7 mmol). The water solution was washed by EtOAc until no UV active compounds were detected, neutralized to pH ~10 by 2M NaOH solution, and then extracted with dichloromethane. The combined extracts were dried over Na$_2$SO$_4$. After filtration, the filtrate was condensed to 50 mL and used in the next step without further isolation. To that solution was added 1M (Boc)$_2$O in THF (Aldrich, 11 mL, 11 mmol). The reaction mixture was stirred at room temperature for overnight. The solvents were evaporated and the residue was dissolved in dichloromethane (200 mL), washed by 0.5 N HCl, saturated aqueous NaHCO$_3$ and brine, and dried over Na$_2$SO$_4$. After filtration, evaporation and high vacuum dry, the product (compound 29) was obtained as a light yellow crystalline solid (2.48 mg, 99% yield). TLC R$_f$ 0.40 (hexane:EtOAc 3:1), $^1$H-NMR (400 MHz, CDCl$_3$): δ7.57 (dd, 1H, J 7.9 Hz, J 6.4 Hz), 7.17 (d, 1H, J 7.9 Hz), 7.14 (d, 1H, J 9.5 Hz), 5.02 (bs, 1H), 4.36 (bd, 2H, J 5.5 Hz), 1.46 (s, 9H).

The following procedure is based on a literature reference (M. G. Palermo, Tetrahedron Lett. 37 (17), 1996, 2885–2886) for making the similar compounds. To the solution of acetohydroxamic acid (Aldrich, compound 36, 450.4 mg, 6.0 mmol) in anhydrous DMF (4 mL) was added t-BuOK (Aldrich, 673.3 mg, 6.0 mmol). The mixture was stirred at room temperature under nitrogen for 30 minutes to get a gel-like suspension. Compound 29 (1.00 g, 4.0 mmol) was introduced, and the reaction mixture was stirred at room temperature under nitrogen for 15 hours and then at 70° C. for 24 hours. The mixture was cooled to room temperature, poured into water, and extracted with EtOAc. The combined extracts were washed with brine five times and dried over Na$_2$SO$_4$. After filtration and evaporation, the crude product was purified on a silica gel column eluting with hexane-EtOAc (from 4:1 to 1:1) to give some recovered compound 29 (415 mg, 1.66 mmol, 41%) and the product 37 as a white crystalline solid (583 mg, 55% yield, 95% yield based on the recovered starting material). TLC R$_f$ 0.09 (hexane:EtOAc 3:1); $^1$H-NMR (400 MHz, CDCl$_3$): δ 7.47 (d, 1H, J 8.1 Hz), 7.34 (s, 1H), 7.18 (d, 1H, J 8.1 Hz), 4.97 (bs, 1H), 4.45 (bd, 2H, J 5.5 Hz), 4.36 (bs, 2H), 1.47 (s, 9H).

Example 29

Preparation of (38)

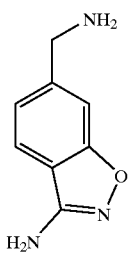

Compound 37 (580 mg, 2.20 mmol) was dissolved in 2M HCl in methanol/dioxane (1:1) (20 mL). The reaction mixture was stirred at room temperature for half an hour and a voluminous white precipitate formed. After evaporation of solvents and co-evaporation with dichloromethane, the residue was suspended in methanol (20 mL), and to the mixture was added hydroxide form basic resin (AG 1-X8 Resin from Bio-Rad Laboratories) to make a clear solution and adjust the pH to ~10. The resin was filtered and washed with methanol thoroughly. The methanol solution was evaporated and the residue was dried under high vacuum to provide a free amine (compound 38) as a white solid (356 mg, 100% yield).

Example 30

Preparation of (39)

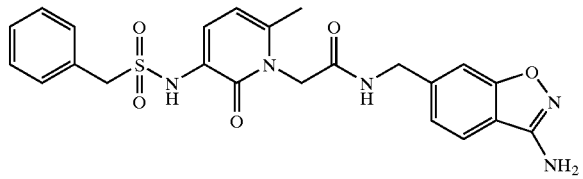

To a solution of 3-benzylsulfonylamino-6-methyl-1-methylenecarboxy-2-pyridinone (compound 21, 288.6 mg, 0.85 mmol) in DMF (4 mL), were added HOAt (Aldrich, 127.3 mg, 0.94 mmol), EDC (Aldrich, 180.2 mg, 0.94 mmol) and compound 38 (140 mg, 0.85 mmol). The mixture was stirred under nitrogen at room temperature for 15 hours, and then poured into water (60 mL). The product was extracted with EtOAc, and the combined extracts were washed with aqueous saturated NaHCO$_3$ and dried over Na$_2$SO$_4$. After filtration and evaporation, the residue was purified using reversed phase preparatory HPLC, eluting with an acetonitrile-0.1% TFA in water system. The pure fractions were concentrated and lyophilized to provide a white solid product (175 mg, 100% purity, 43% yield). MS: m/e 482.2 (M+H)$^+$, 963.4 (2M+H)$^+$; $^1$H-NMR (400 MHz, CD$_3$OD): δ 7.67 (d, 1H, J 8.2 Hz), 7.37 (s, 1H), 7.31 (d, 1H, J 7.6 Hz), 7.28–7.20 (m, 6H), 6.13 (d, 1H, J 7.6 Hz), 4.86 (s, 2H), 4.55 (s, 2H), 4.40 (s, 2H), 2.31 (s, 3H).

Figure 6:
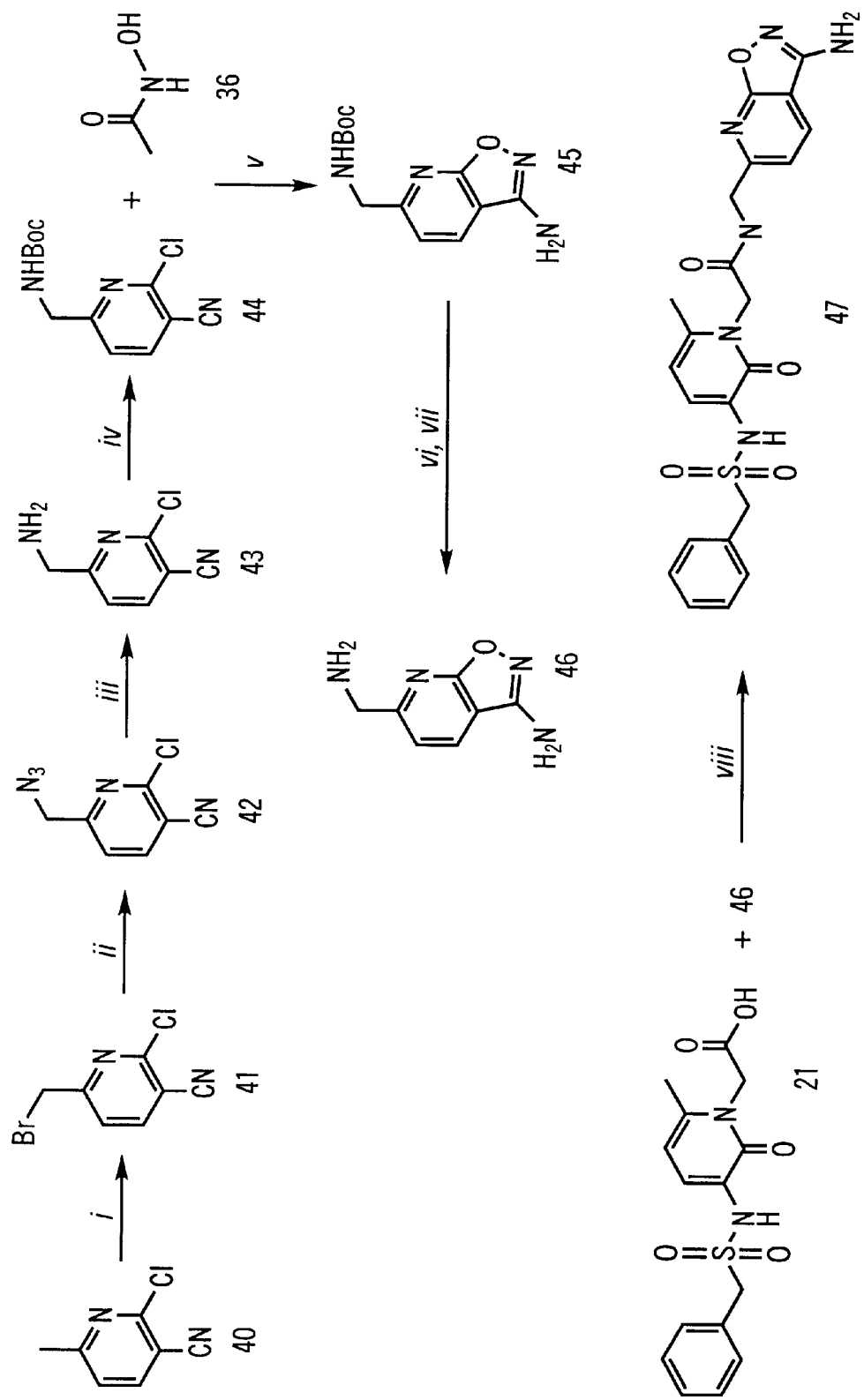
FIG. 6 depicts a reaction scheme for the synthesis of a compound having thrombin inhibitory activity. In this figure "i" through "viii" are defined as follows: i) NBS, benzoyl peroxide, CCl$_4$, reflux 6 hours; ii) NaN$_3$, DMF, room temperature 15 hours; iii) Ph$_3$P, THF/H$_2$O, 0° C., 0° C. to room temperature 15 hours, 0.25M HCl, neutralize with NaOH; iv) DCM, 1M Boc$_2$O in THF, room temperature 15 hours; v) t-BuOK, DMF, room temperature 15 hours, add 44, room temperature 15 hours, 65° C. 4 hours; vi) 2M HCl, methanol/dioxane, room temperature 4 hours; vii) OH$^-$ resin; and viii) HOAt, EDC, DMF, room temperature 15 hours. These procedures are more fully described in Examples 31 to 36.

F. Preparation of Compound 47 (FIG. 6) Examples 31 to 36

Example 31

Preparation of (41)

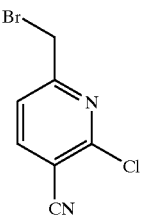

To a solution of 2-chloro-3-cyano-4-methylpyridine (compound 40, Aldrich, 10 g, 65.54 mmol) in carbon tetrachloride (250 mL), were added NBS (Aldrich, 12.83 g, 72.09 mmol) and benzoyl peroxide (1.59 g, 6.55 mmol). The reaction mixture was degassed and charged with nitrogen three times, and then refluxed at 85° C. for 6 hours. After cooling to room temperature, the solid by-product was removed by filtering and washed by CCl$_4$. The filtrate was evaporated and purified on a silica gel column eluting with hexane-EtOAc (from 10:1 to 5:1). The product 41 (5.28 g, 35% yield) was obtained as a light yellow solid. TLC R$_f$ 0.35 (hexane:EtOAc 5:1), $^1$H-NMR (400 MHz, CDCl$_3$) δ 8.01 (d, 1H, J 7.9 Hz), 7.53 (d, 1H, J 7.9 Hz), 4.50 (s, 2H).

Example 32

Preparation of (42)

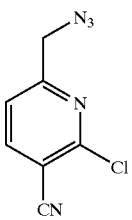

To a solution of α-bromo-2-chloro-3-cyano-4-methylpyridine (compound 41, 5.28 g, 22.83 mmol) in DMF (50 mL), was added sodium azide (Aldrich, 1.78 g, 27.40 mmol). The mixture was stirred at room temperature under nitrogen for 15 hours, and then poured into water (300 mL). The product was extracted with ether, the combined extracts were washed with brine three times, and dried over MgSO$_4$. After filtration and evaporation, the crude product was purified on a silica gel column eluting with hexane-EtOAc (from 9:1 to 5:1) to provide a product 42 as a light yellow solid (3.48 g, 79% yield). TLC R$_f$ 0.11 (hexane:EtOAc 9:1), $^1$H-NMR (400 MHz, CDCl$_3$): δ 8.03 (d, 1H, J 7.9 Hz), 7.47 (d, 1H, J 7.9 Hz), 4.57 (s, 2H).

Example 33

Preparation of (43)

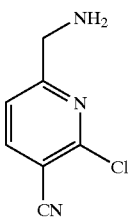

To a solution of α-azido-2-chloro-3-cyano-4-methylpyridine (compound 42, 3.48 g, 17.98 mmol) in THF (84 mL) and water (4 mL), was added triphenylphosphine (5.19 g, 19.77 mmol) slowly at 0° C. The reaction mixture was stirred at a temperature of from 0° C. to room temperature for 15 hours. During this time the color of the solution changed from light yellow to green, and then to deep red color. After evaporation of the solvents, the residue was dissolved in 0.25M HCl (100 mL, 25 mmol). The aqueous solution was washed with EtOAc to give a colorless solution, and then neutralized to pH=11 with 2M NaOH solution. The free amine was extracted with dichloromethane and the combined extracts were dried over $Na_2SO_4$. After filtration, evaporation and high vacuum dry, a green crystalline solid product (43) was obtained (1.58 g, 52% yield). $^1$H-NMR (400 MHz, $CDCl_3$): δ 7.96 (d, 1H, J 7.9 Hz), 7.45 (d, 1H, J 7.9 Hz), 4.05 (s, 2H), 1.64 (bs, 2H).

Example 34
Preparation of (44)

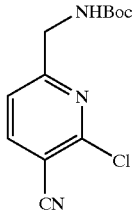

To the solution of a-amino-2-chloro-3-cyano-4-methylpyridine (compound 43, 1.58 g, 9.43 mmol) in dichloromethane (40 mL), was added 1M $(Boc)_2O$ in THF (11.3 mL, 11.3 mmol). The mixture was stirred at room temperature for 15 hours. After evaporation of the solvent, the residue was purified on a silica gel column eluting with hexane-EtOAc (from 5:1 to 3:1) to provide product 44 as an off-white solid (1.07 g, 42% yield). TLC $R_f$ 0.73 (hexane:EtOAc 1:1); $^1$H-NMR (400 MHz, $CDCl_3$): δ 7.96 (d, 1H, J 7.9 Hz), 7.38 (d, 1H, J 7.9 Hz), 5.32 (bs, 1H), 4.46 (bd, 2H, J 5.8 Hz), 1.46 (s, 9H).

Example 35
Preparation of (45)

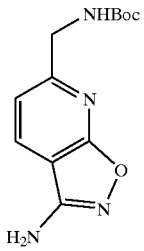

This is an modification based on a literature procedure (M. G. Palermo, Tetrahedron Lett. 37 (17), 1996, 2885–2886). To a solution of acetohydroxamic acid (36, 224.6 mg, 2.99 mmol) in anhydrous DMF (4 mL), was added t-BuOK (335.5 mg, 2.99 mmol). The mixture was stirred at room temperature under nitrogen for 15 minutes to get a gel-like suspension. To the mixture was added compound 44 (534 mg, 1.99 mmol). The reaction mixture was stirred at room temperature under nitrogen for 15 hours and then at 65° C. for 4 hours. After cooling to room temperature, the mixture was poured into water (100 mL) and extracted with EtOAc. The combined extracts were washed with brine five times and dried over $Na_2SO_4$. After filtration and evaporation, the crude product was purified on a silica gel column eluting with hexane-EtOAc (from 3:1 to 1:2) to provide the product, compound 45, as an off-white solid (370 mg, 70% yield). TLC $R_f$ 0.20 (hexane:EtOAc 1:1); $^1$H-NMR (400 MHz, $CDCl_3$): δ 7.89 (d, 1H, J 7.9 Hz), 7.25 (d, 1H, J 7.9 Hz), 5.56 (bs, 1H), 4.56 (bd, 2H, J 5.5 Hz), 4.42 (bs, 2H), 1.46 (s, 9H).

Example 36
Preparation of (47)

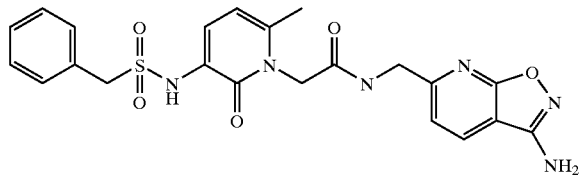

Compound 45 (340 mg, 1.29 mmol) was dissolved in a 2M HCl methanol/dioxane (1:1) solution (20 mL). The reaction mixture was stirred at room temperature for 4 hours and a voluminous white precipitate was formed. After evaporation of solvent and co-evaporation with dichloromethane, the residue was suspended in methanol (20 mL). To that mixture was added hydroxide form basic resin (AG 1-X8 Resin from Bio-Rad Laboratories) to make a clear solution and adjust the pH ~10. The resin was filtered and washed with methanol thoroughly. The methanol solution was evaporated and the residue was dried under high vacuum to provide the free amine compound 46 as a white solid (204 mg, 99% yield).

To the solution of 3-benzylsulfonylamino-6-methyl-1-methylenecarboxy-2-pyridinone (compound 21, 206.9 mg, 0.62 mmol) in DMF (3 mL), were added HOAt (Aldrich, 92.8 mg, 0.68 mmol), EDC (Aldrich, 130.4 mg, 0.68 mmol) and the amine compound 46 (101 mg, 0.62 mmol). The reaction mixture was stirred under nitrogen at room temperature for 15 hours and then poured into water (50 mL). The product was extracted with EtOAc, the combined extracts were washed with aqueous saturated $NaHCO_3$ and dried over $Na_2SO_4$. After filtration and evaporation, the residue was purified by reversed phase preparatory HPLC, eluting with an acetonitrile-0.1% TFA in water system. The pure fractions were concentrated and lyophilized to provide product compound 47 as a white solid (180 mg, 100% purity, 60% yield). MS: m/e 483.0 $(M+H)^+$, 965.2 $(2M+H)^+$; $^1$H-NMR (400 MHz, $CD_3OD$): δ $^1$H-NMR (400 MHz, $CD_3OD$): δ 8.18 (d, 1H, J 7.9 Hz), 7.35 (d, 1H, J 7.9 Hz), 7.31 (d, 1H, J 7.6 Hz), 7.28–7.22 (m, 5H), 6.14 (d, 1H, J 7.6 Hz), 4.91 (s, 2H), 4.61 (s, 2H), 4.40 (s, 2H), 2.35 (s, 3H).

Figure 7:
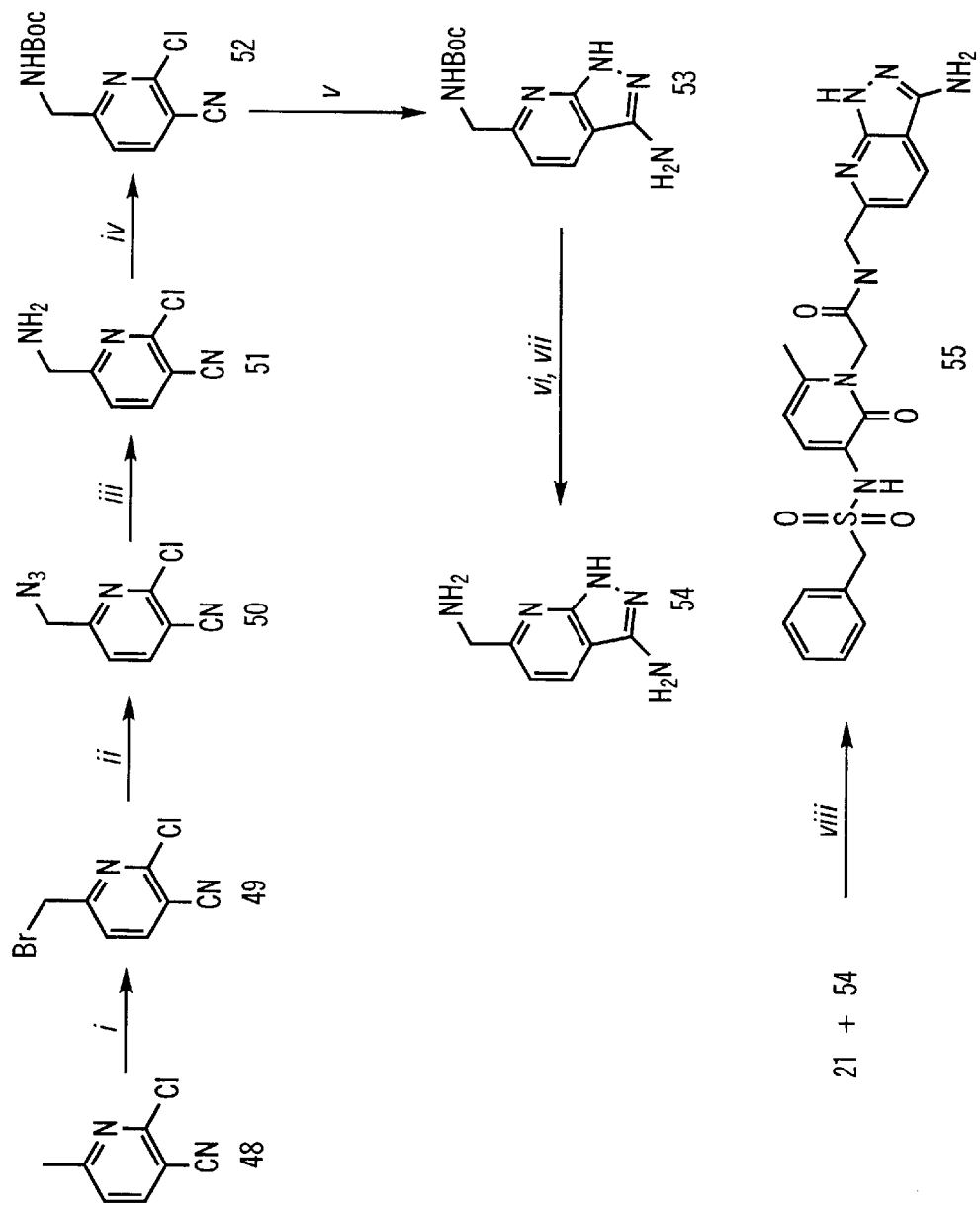
FIG. 7 depicts a reaction scheme for the synthesis of a compound having thrombin inhibitory activity. In this figure, "i" through "viii" are defined as follows: i) NBS, benzoyl peroxide, CCl$_4$, reflux 6 hours; ii) NaN$_3$, DMF, room temperature 15 hours; iii) Ph$_3$P, THF/H$_2$O, room temperature 15 hours; iv) DCM, 1M Boc$_2$O in THF, room temperature 15 hours; v) hydrazine, n-butanol, reflux 4 hours; vi) 2M HCl methanol/dioxane, room temperature 3 hours; vii) OH$^-$ resin; and viii) HOAt, EDC, DMF, room temperature 15 hours. These procedures are more fully described in Examples 39 to 45.

G. Preparation of Compound 55 (FIG. 7) Examples 39 to 45

Example 39
Preparation of (49)

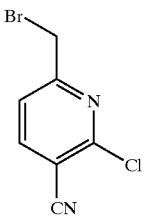

To a solution of 2-chloro-3-cyano-4-methylpyridine (compound 48, Aldrich, 10 g, 65.54 mmol) in carbon tetrachloride (250 mL), were added NBS (Aldrich, 12.83 g, 72.09 mmol) and benzoyl peroxide (Aldrich, 1.59 g, 6.55 mmol). The reaction mixture was degassed and charged with nitrogen three times, and then refluxed at 85° C. for 6 hours. After cooling to room temperature, the solid by-product was filtered off and washed by CCl$_4$. The filtrate was evaporated and purified on a silica gel column eluting with hexane-EtOAc (from 10:1 to 5:1). The product (Compound 49, 5.28 g, 35% yield) was obtained as a light yellow solid. TLC R$_f$ 0.35 (hexane:EtOAc 5:1), $^1$H-NMR (400 MHz, CDCl$_3$): δ 8.01 (d, 1H, J 7.9 Hz), 7.53 (d, 1H, J 7.9 Hz), 4.50 (s, 2H).

Example 40
Preparation of (50)

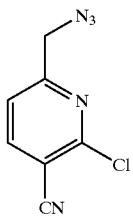

To a solution of a-bromo-2-chloro-3-cyano-4-methylpyridine (compound 49, 5.28 g, 22.83 mmol) in DMF (50 mL), was added sodium azide (Aldrich, 1.78 g, 27.40 mmol). The mixture was stirred at room temperature under nitrogen for 15 hours, and then poured into water (300 mL). The product was extracted with ether, the combined extracts were washed with brine three times, and dried over MgSO$_4$. After filtration and evaporation, the crude product was purified on a silica gel column eluting with hexane-EtOAc (from 9:1 to 5:1) to provide a light yellow solid product (compound 50, 3.48 g, 79% yield). TLC R$_f$ 0.11 (hexane:EtOAc 9:1), $^1$H-NMR (400 MHz, CDCl$_3$): δ 8.03 (d, 1H, J 7.9 Hz), 7.47 (d, 1H, J 7.9 Hz), 4.57 (s, 2H).

Example 41
Preparation of (51)

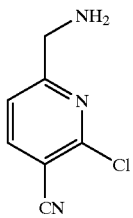

To a solution of α-azido-2-chloro-3-cyano-4-methylpyridine (compound 50, 3.48 g, 17.98 mmol) in THF (84 mL) and water (4 mL), was added triphenylphosphine (Aldrich, 5.19 g, 19.77 mmol) slowly at 0° C. The mixture was stirred at a temperature of from 0° C. to room temperature for 15 hours. During this time, the color of the solution changed from light yellow to green, and then to a deep red color. After evaporation of the solvents, the residue was dissolved in 0.25M HCl (100 mL, 25 mmol). The aqueous solution was washed by EtOAc to give a colorless solution, and then neutralized to pH 11 with 2M NaOH solution. The free amine was extracted with dichloromethane and the combined extracts were dried over Na$_2$SO$_4$. After filtration, evaporation and high vacuum dry, a green crystalline solid product (51) was obtained (1.58 g, 52% yield). $^1$H-NMR (400 MHz, CDCl$_3$): δ 7.96 (d, 1H, J 7.9 Hz), 7.45 (d, 1H, J 7.9 Hz), 4.05 (s, 2H), 1.64 (bs, 2H).

Example 42
Preparation of (52)

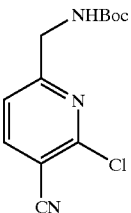

To a solution of α-amino-2-chloro-3-cyano-4-methylpyridine (compound 51, 1.58 g, 9.43 mmol) in dichloromethane (40 mL) was added 1M (Boc)$_2$O in THF (11.3 mL, 11.3 mmol). The reaction mixture was stirred at room temperature for 15 hours. After evaporation of the solvent, the residue was purified on a silica gel column eluting with hexane-EtOAc (from 5:1 to 3:1) to provide an off-white solid product (1.07 g, 42% yield). TLC R$_f$ 0.73 (hexane:EtOAc 1:1), $^1$H-NMR (400 MHz, CDCl$_3$): δ 7.96 (d, 1H, J 7.9 Hz), 7.38 (d, 1H, J 7.9 Hz), 5.32 (bs, 1H), 4.46 (bd, 2H, J 5.8 Hz), 1.46 (s, 9H).

Example 43
Preparation of (53)

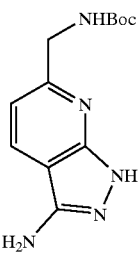

To a solution of compound 52 (535.4 mg, 2.0 mmol) in n-butanol (10 mL) was added hydrazine (0.19 mL, 6.0 mmol). The reaction mixture was refluxed under nitrogen for 4 hours. After evaporation of n-butanol and high vacuum dry, the product was obtained as a light yellow solid (526 mg, 100% yield). TLC R$_f$ 0.15 (5% MeOH in CH$_2$Cl$_2$), $^1$H-NMR (400 MHz, CD$_3$OD): δ 8.07 (d, 1H, J 8.2 Hz), 6.99 (d, 1H, J 8.2. Hz), 4.37 (s, 2H), 1.44 (s, 9H).

Example 44
Preparation of (54)

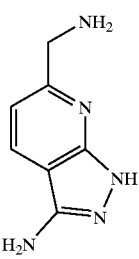

Compound 53 (520 mg, 1.97 mmol) was dissolved in a 2M HCl methanol/dioxane (1:1) solution (20 mL). The reaction mixture was stirred at room temperature for 3 hours and a voluminous red precipitate formed. The precipitate was filtered off. After evaporation of solvent and co-evaporation with dichloromethane, the residue was suspended in methanol (20 mL), and to the mixture was added hydroxide form basic resin (AG 1-X8 Resin from Bio-Rad Laboratories) to make a clear solution and adjust the pH=10. The resin was filtered and washed with methanol thoroughly. The methanol solution was evaporated and the residue was dried under high vacuum to provide the free amine (compound 54) as a light yellow-green solid (303 mg, 94% yield). $^1$H-NMR (400 MHz, CD$_3$OD): δ 8.09 (d, 1H, J 8.2 Hz), 7.02 (d, 1H, J 8.2 Hz), 4.05 (s, 2H).

Example 45
Preparation of (55)

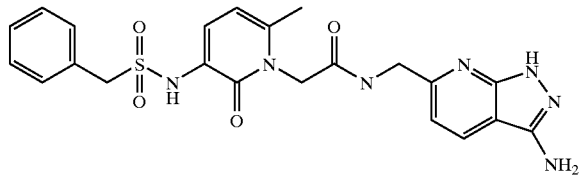

To the solution of 3-benzylsulfonylamino-6-methyl-1-methylenecarboxy-2-pyridinone (compound 21, 282 mg, 0.84 mmol) in DMF (4 mL), were added HOAt (Aldrich, 125.2 mg, 0.92 mmol), EDC (Aldrich, 176.4 mg, 0.92 mmol) and the amine compound 54 (136.8 mg, 0.84 mmol). The mixture was stirred under nitrogen at room temperature for 15 hours, and then poured into water (50 mL). The product was extracted with EtOAc, and the combined extracts were washed by saturated aqueous NaHCO$_3$ and dried over Na$_2$SO$_4$. After filtration and evaporation, the residue was purified by reversed phase preparatory HPLC, eluting with an acetonitrile-0.1% TFA in water system. The pure fractions were concentrated and lyophilized to provide a white solid product 55 (11.0 mg, 90% purity). MS: m/e 482.2 (M+H)$^+$, 963.4 (2M+H)$^+$; $^1$H-NMR (400 MHz, CD$_3$OD): δ 8.18 (d, 1H, J 7.9 Hz), 7.33 (d, 1H, J 7.6 Hz), 7.25–7.18 (m, 5H), 7.11 (d, 1H, J 7.9 Hz), 6.16 (d, 1H, J 7.6 Hz), 4.90 (s, 2H), 4.62 (s, 2H), 4.40 (s, 2H), 2.35 (s, 3H).

Figure 8:
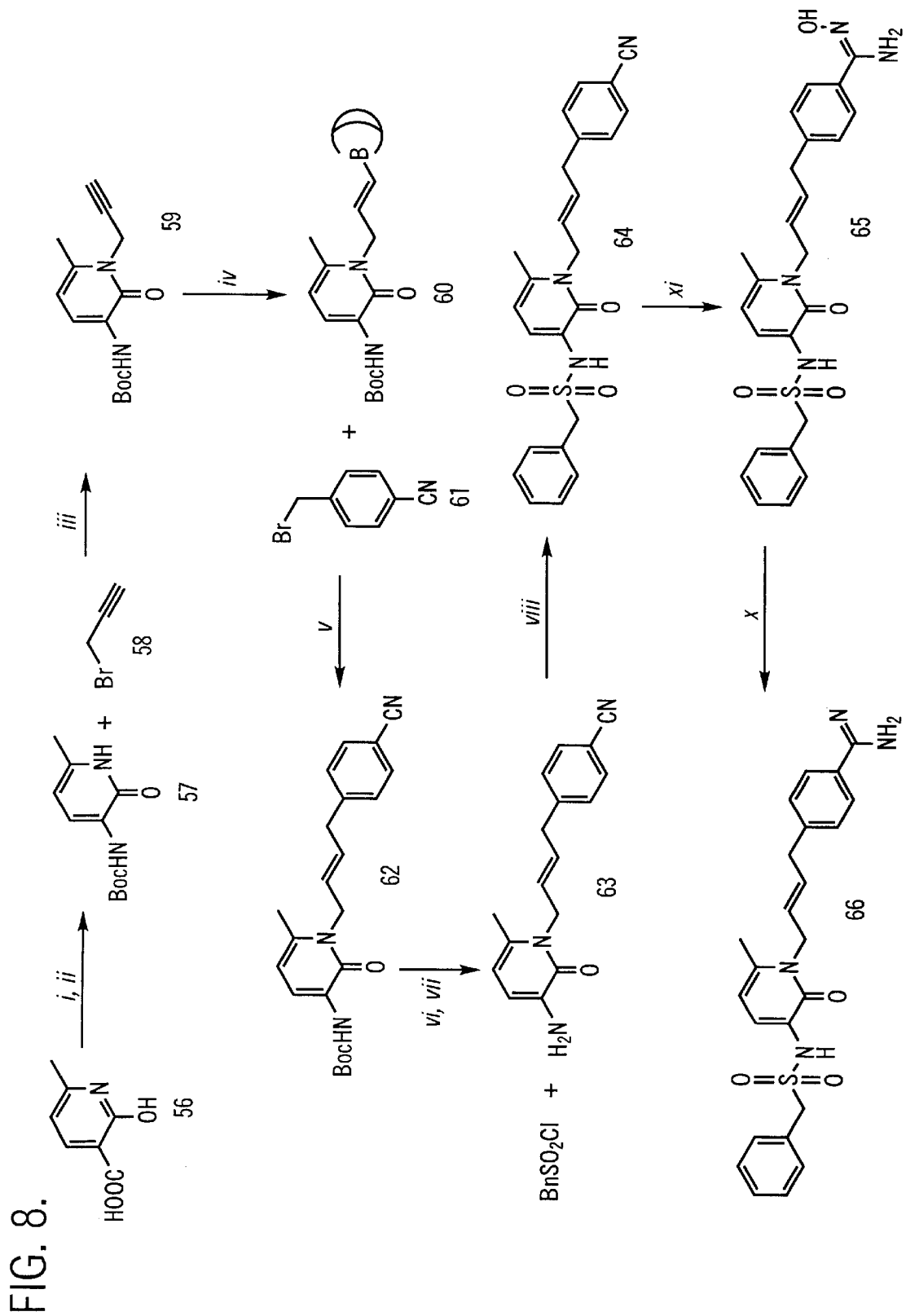
FIG. 8 depicts a reaction scheme for the synthesis of a compound having thrombin inhibitory activity. In this figure, "i" through "xx" are defined as follows: i) DPPA, Et$_3$N, dioxane, reflux 20 hours; ii) tert-butanol, Et$_3$N, reflux 20 hours; iii) 58, CS$_2$CO$_3$, DMF, room temperature 15 hours; iv) 9-BBN, THF, 0° C. one hour, 5° C. 16 hours; v) warm 60 to room temperature, 3M NaOH, Pd(PPh$_3$)$_4$, reflux 7 hours; vi) 2M HCl/dioxane, 5° C., fifteen hours, room temperature 4 hours; vii) OH$^-$ resin; viii) CH$_3$CN, α-toluene-sulfonyl chloride, 2,4,6-collidine, room temperature, 15 minutes; ix) hydroxylamine hydrochloride, Et$_3$N, ethanol, 80° C., four hours; and x) Zn, HOAc/H$_2$O. These procedures are more fully described in Examples 46 to 51.

H. Preparation of Compound 66 (FIG. 8) Examples 46 to 51

Example 46
Preparation of 3-tert-Butyloxycarbonylamino-6-methyl-2-pyridinone (57)

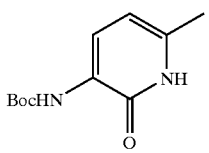

To the suspension of 2-hydroxy-6-methylpyridine-3-carboxylic acid (56) (Aldrich, 15.31 g, 100 mmol) in anhydrous 1,4-dioxane (200 mL), were added triethylamine (Aldrich, 13.9 mL, 100 mmol), and then DPPA (Aldrich, 21.6 mL, 100 mmol). The reaction mixture was refluxed under nitrogen for 20 hours and the solid dissolved gradually to give a clear solution. A voluminous precipitate formed. To the mixture were added tert-butanol (9.6 mL, 100 mmol) and triethylamine (13.9 mL, 100 mmol). The mixture refluxed under nitrogen for 20 hours. After evaporation of most of the solvent, the residue was partitioned between water and dichloromethane. The aqueous layer was acidified to pH=1 with 0.5 M HCl and then extracted with dichloromethane twice. The combined extracts were washed by saturated aqueous NaHCO$_3$, brine, and dried over Na$_2$SO$_4$. After filtration and evaporation, the crude mixture was purified on a silica gel column eluting with hexane-EtOAc-AcOH (2:1:0.004, 3:2:0.004, and 1:1:0.004). The pure fractions were concentrated and dried under high vacuum to provide a white crystalline solid product (6.00 g, 27% yield). TLC R$_f$ 0.53 (Hexane:EtOAc:AcOH 1:1:0.002); $^1$H-NMR (400 MHz, CDCl$_3$): δ 7.99 (bd, 1H, J 7.6 Hz), 7.42 (bs, 1H), 6.05 (d, 1H, J 7.6), 2.30 (s, 3H), 1.52 (s, 9H).

Example 47
Preparation of (59)

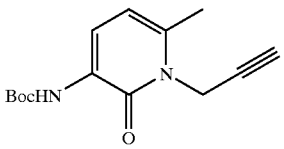

To a mixture of 3-tert-butyloxycarbonylamino-6-methyl-2-pyridinone (compound 57, 2.24 g, 10.0 mmol) and Cs$_2$CO$_3$ (Aldrich, 3.26 g, 10.0 mmol) in DMF (20 mL), was added propargyl bromide (compound 58, Aldrich, 1.1 mL, 10 mmol). The reaction mixture was stirred under nitrogen at room temperature for 15 hours and then poured into water (200 mL). The aqueous mixture was extracted with ether three times. The combined extracts were washed with brine and dried over Na$_2$SO$_4$. After filtration and evaporation, the crude product was purified on a silica gel column eluting with hexane-EtOAc (5:1) to provide a white crystalline solid product (2.26 g, 86% yield). TLC R$_f$ 0.17 (hexane:EtOAc 5:1); $^1$H-NMR (400 MHz, CDCl$_3$): δ 7.85 (bd, 1H, J 7.6 Hz), 7.54 (bs, 1H), 6.06 (d, 1H, J 7.6), 4.88 (d, 2H, J 2.1 Hz), 2.44 (s, 3H), 2.24 (t, 1H, J 2.1 Hz), 1.48 (s, 9H).

Example 48
Preparation of (62)

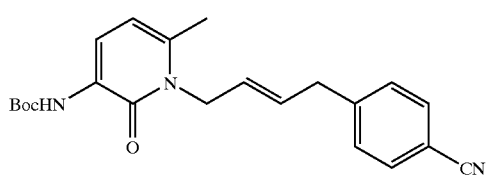

To a solution of compound 59 (2.207 g, 8.41 mmol) in anhydrous THF (20 mL), was added a 0.5 M solution of 9-BBN in THF (Aldrich, 16.8 mL, 8.41 mmol) slowly through a syringe at 0° C. under nitrogen. After the addition was complete, the reaction mixture was stirred at 0° C. under nitrogen for one hour, and then was stored in a refrigerator (5° C.) under nitrogen for 16 hours to form compound 60. The reaction flask was warmed to room temperature under nitrogen. To the reaction mixture were added 4-cyanobenzylbromide (compound 61, Aldrich, 1.649 g, 8.41 mmol), 3M NaOH (8.4 mL, 25.2 mmol), and the catalyst Pd(PPh$_3$)$_4$ (Aldrich, 288.9 mg, 0.25 mmol) The yellow reaction mixture was degassed and charged with nitrogen; the procedure was repeated for two more times. The reaction mixture refluxed under nitrogen for 7 hours, then was cooled to room temperature and diluted with hexane (50 mL). To the resulting solution was added a 30% solution of H$_2$O$_2$ in water (6 mL) and the mixture was stirred for 10 minutes at room temperature. The layers were separated; the aqueous layer was extracted with EtOAc. The combined extracts were washed with brine and dried over Na$_2$SO$_4$. After filtration and evaporation, the crude product was purified on a silica gel column eluting with hexane-EtOAc (from 5:1 to 2:1) to provide a colorless foam solid product (1.27 g, 40% yield). TLC R$_f$ 0.23 (hexane:EtOAc 2:1); $^1$H-NMR (400 MHz, CD$_3$OD): δ 7.82 (bd, 1H, J 7.0 Hz), 7.59 (d, 2H, J 8.2 Hz), 7.31 (d, 2H, J 8.2 Hz), 6.16 (d, 1H, J 7.0 Hz), 5.60 (m, 2H), 4.72 (d, 2H, J 4.3 Hz), 3.42 (d, 2H, J 5.5 Hz), 2.32 (s, 3H), 1.48 (s, 9H).

Example 49

Preparation of (63)

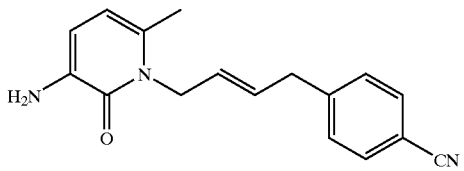

A solution of compound 62 (1.11 g, 2.93 mmol) in a 2M HCl/dioxane solution (Aldrich, 40 mL) was allowed to stand at 5° C. for 15 hours and then at room temperature for 4 hours. After evaporation and co-evaporation with toluene, the residue was dissolved in methanol (20 mL), and the resulting solution was neutralized to pH=9 with basic OH$^-$ resin. TLC of the methanol solution showed very complicated results which indicated decomposition of the product. After evaporation, the crude mixture was purified on a silica gel column eluting with 1% methanol in dichloromethane and 2% methanol in dichloromethane to provide a colorless foam solid free amine product (compound 63, 114 mg, 14% yield). TLC R$_f$ 0.22 (hexane:EtOAc:AcOH 1:1:0.02); $^1$H-NMR (400 MHz, CD$_3$OD): δ 7.60 (d, 2H, J 8.2 Hz), 7.31 (d, 2H, J 8.2 Hz), 6.60 (d, 1H, J 7.6 Hz), 6.04 (d, 1H, J 7.6 Hz), 5.66 (dt, 1H, J 15.6 Hz, J 4.9 Hz), 5.56 (dt, 1H, J 15.6 Hz, J 6.4 Hz), 4.72 (d, 2H, J 4.9 Hz), 3.42 (d, 2H, J 6.4 Hz), 2.27 (s, 3H).

Example 50

Preparation of (64)

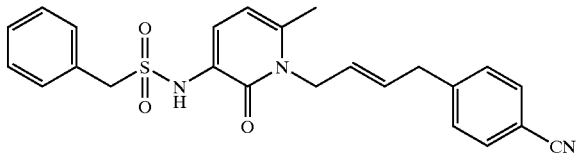

To a solution of compound 63 (114 mg, 0.41 mmol) in anhydrous acetonitrile (2 mL) were added α-toluenesulfonyl chloride (Aldrich, 122.5 mg, 0.49 mmol) and 2,4,6-collidine (Aldrich, 0.12 mL, 0.90 mmol). The solution was stirred under nitrogen at room temperature for 15 minutes, diluted with EtOAc, washed with saturated aqueous NH$_4$Cl, saturated aqueous NaHCO$_3$ and brine, and dried over Na$_2$SO$_4$. After filtration and evaporation, the crude product was purified on a silica gel column eluting with hexane-EtOAc (2:1 and 1:1) to provide product compound 64 as a light yellow foam solid (148 mg, 83% yield). TLC R$_f$ 0.46 (hexane:EtOAc:AcOH 1:1:0.02); $^1$H-NMR (400 MHz, CD$_3$OD): δ7.57 (d, 2H, J 8.2 Hz), 7.32 (d, 2H, J 8.2 Hz), 7.24 (m, 6H), 6.04 (d, 1H, J 7.3 Hz), 5.69 (dt, 1H, J 15.9 Hz, J 4.6 Hz), 5.60 (dt, 1H, J 15.9 Hz, J 6.4 Hz), 4.72 (d, 2H, J 4.6 Hz), 4.38 (s, 2H), 3.45 (d, 2H, J 6.4 Hz), 2.32 (s, 3H).

Example 51

Preparation of (66)

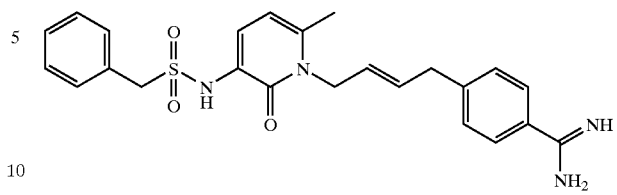

To a solution of compound 64 (83 mg, 0.19 mmol) in ethanol (2 mL), was added hydroxylamine hydrochloride (20.2 mg, 0.29 mmol) and triethylamine (0.053 mL, 0.38 mmol). The reaction mixture was stirred under nitrogen at 80° C. for 4 hours. The solvent was evaporated and the residue was dissolved in dichloromethane. The organic solution was washed by water and dried over Na$_2$SO$_4$. After filtration and evaporation, crude product, compound 65 (79 mg, 89% mass recovery, TLC R$_f$ 0.41, 5% MeOH in CH$_2$Cl$_2$), was obtained, which was used for the next step without further purification.

To the solution of compound 65 in acetic acid (2 mL) and water (0.5 mL), was added freshly activated zinc dust. The reduction was monitored by Mass Spectrum for completion. The reaction mixture was diluted with water, filtered, and purified by a reversed phase preparatory HPLC. The pure fractions were concentrated and lyophilized to give compound 66 (30 mg, 90% purity determined by $^1$H-NMR method). $^1$H-NMR (400 MHz, CD$_3$OD): δ7.66 (d, 2H, J 8.5 Hz), 7.34 (d, 2H, J 8.5 Hz), 7.23 (m, 6H), 6.06 (d, 1H, J 7.6 Hz), 5.69 (dt, 1H, J 15.6 Hz, J 4.7 Hz), 5.62 (dt, 1H, J 15.6 Hz, J 6.3 Hz), 4.73 (d, 2H, J 4.7 Hz), 4.39 (s, 2H), 3.49 (d, 2H, J 6.3 Hz), 2.33 (s, 3H).

Figure 9:
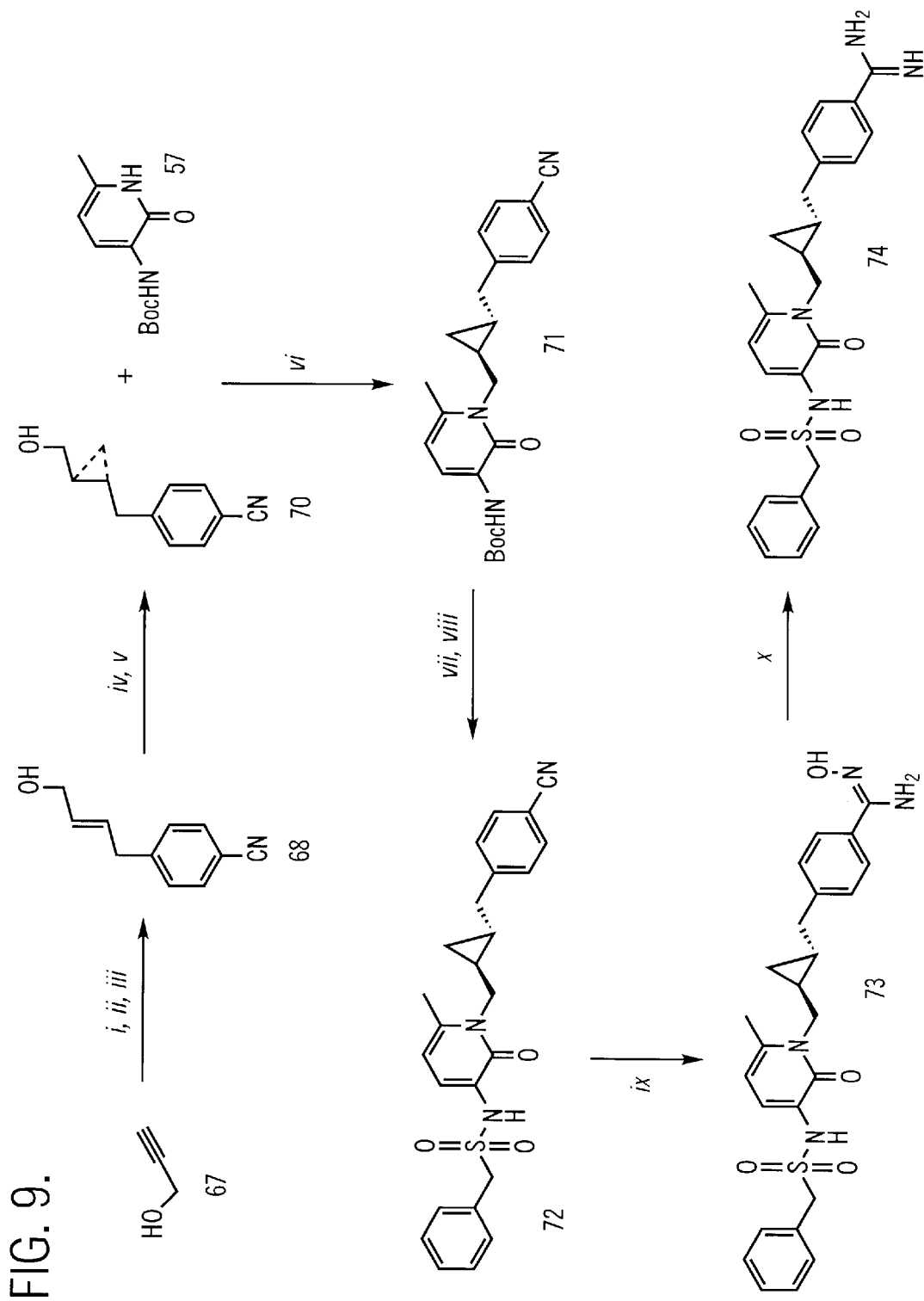
FIG. 9 depicts a reaction scheme for the synthesis of a compound having thrombin inhibitory activity. In this figure, "i" through "x" are defined as follows: i) 9-BBN, THF, 0° C. one hour, 5° C., 18 hours, warm to room temperature; ii) compound 61, Pd(PPh$_3$)$_4$, 2M NaOH, reflux 2 hours, cool to room temperature; iii) 30% H$_2$O$_2$/H$_2$O, room temperature about one hour; iv) ZnEt$_2$ in hexane/DCM, CH$_2$I$_2$, 69 (see Example 53) in DCM, 0° C. to room temperature 15 hours; v) 2N NaOH, room temperature overnight; vi) Ph$_3$P, THF, DEAD, 0° C. ten minutes, room temperature 30 minutes; vii) 4M HCl/EtOAc, room temperature 3 hours; viii) CH$_3$CN, 2,4,6-collidine, α-toluene sulfonyl chloride, room temperature 4 hours; ix) hydroxylamine HCl, Et$_3$N, ethanol, 60° C. overnight; and x)Zn, HOAc/H$_2$O. These procedures are described more fully in Examples 52 to 57.

I. Preparation of Compound 74 (FIG. 9) Examples 52 to 57

Example 52

Preparation of E-4-(4-cyanophenyl)-2-buten-1-ol (68)

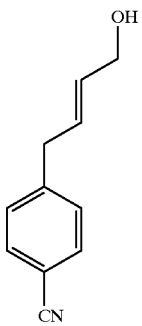

To a solution of propargyl alcohol (67, Aldrich, 1.46 mL, 25 mmol) in anhydrous tetrahydrofuran (10 mL), was added 0.5M 9-BBN in THF (Aldrich, 100 mL, 50 mmol) through an addition funnel at 0° C. under nitrogen over a period of 1 hour. After the addition was complete, the flask with the reaction mixture was stored in a 5° C. refrigerator under nitrogen for 18 hours. The reaction mixture was warmed to room temperature under nitrogen. To the reaction mixture was added 4-bromotolunitrile (compound 61, Aldrich, 5.88 g, 30 mmol), tetrakis(triphenyl-phosphine)palladium (0) (Aldrich, 1.00 g, 0.86 mmol), and 2M sodium hydroxide solution (25 mL, 50 mmol). The reaction mixture was degassed with nitrogen three times, and then refluxed at 65° C. for 2 hours. The reaction mixture was cooled to room temperature. To that solution was added slowly 30% hydrogen peroxide in water (30 mL) and 2M sodium hydroxide solution (10 mL). A lot of gas was released during addition of hydrogen peroxide. The resulting solution was stirred at room temperature for an additional hour. The reaction mixture was extracted with ethyl acetate. The combined extracts were washed with brine and then dried over $Na_2SO_4$. After filtration and evaporation, the crude product was purified on a silica gel column, eluting with hexane-ethyl acetate (4:1 and 3:1). The product 68 was obtained as colorless oil (1.05 g, 24% yield). TLC $R_f$ 0.30 (Hexane:EtOAc 1:1); $^1$H-NMR (400 MHz, $CDCl_3$): δ 7.58 (d, 2H, J 8.1 Hz), 7.29 (d, 2H, J 8.1 Hz), 5.82 (dt, 1H, J 15.6 Hz, J 6.4 Hz), 5.71 (dt, 1H, J 15.6 Hz, J 5.4 Hz), 4.14 (d, 2H, J 5.4 Hz), 3.44 (d, 2H, J 6.4 Hz), 1.62 (s, 1H).

Example 53

Preparation of (4R)-trans-2-Butyl-N,N,N',N'-tetramethyl[1,3,2]dioxaborolane-4,5-dicarboxamide (69)

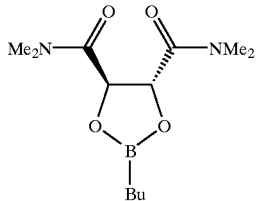

This compound was prepared using a modified literature procedure: A. B. Charette, S. Prescott, and C. Brochu, *J. Org. Chem.* 1995, 60, 1081–1083. To a solution of L-N,N,N',N'-tetramethyltartamide (Aldrich, 15.3 g, 74.9 mmol) in anhydrous toluene (50 mL), was added 1-butaneboronic acid (Aldrich, 9.15 g, 89.9 mmol). The mixture was heated under reflux to remove the water produced in the reaction using a Dean-Stark collector, and 2.3 mL water was collected (compared to 2.7 mL water in theoretical yield). Toluene was evaporated and the residue was dried under high vacuum. A small amount of dichloromethane was introduced, but no 1-butaneboronic acid precipitate was observed (as described in the reference). $^1$H-NMR of the crude product showed the presence of 1-butaneboronic acid. The crude product was dissolved in dichloromethane (300 mL), washed with saturated aqueous $NaHCO_3$ and brine, and dried over $Na_2SO_4$. After filtration, evaporation and high vacuum dry, a viscous light-yellow product 69 was obtained (15.6 g, 77%). $^1$H-NMR (400 MHz, $CDCl_3$): δ 5.53 (s, 2H), 3.20 (s, 6H), 2.98 (s, 6H), 1.40–1.29 (m, 4H), 0.89–0.83 (m, 5H)

Example 54

Preparation of (70)

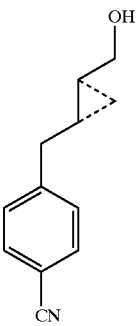

This procedure is developed based on general references for enantioselective cyclopropanation of olefins: (a) A. G. M. Barrett, W. W. Doubleday, K. Kasdorf, and G. J. Tustin, *J. Org. Chem.* 1996, 61, 3280–3288. (b) A. B. Charette, S. Prescott, and C. Brochu, *J. Org. Chem.* 1995, 60, 1081–1083.

To a flask of anhydrous dichloromethane (6 mL) was added a 1.0 M solution of diethylzinc in hexane (Aldrich, 2.93 mL, 2.93 mmol) under nitrogen at 0° C. To another flask of anhydrous dichloromethane (6 mL) were added (E)-4-(4-cyanophenyl)-2-buten-1-ol (compound 68, 230 mg, 1.33 mmol) and (4R-trans)-2-Butyl-N,N,N',N'-tetramethyl[1,3,2]dioxaborolane-4,5-dicarboxamide (compound 69, 395.2 mg, 1.46 mmol) under nitrogen at room temperature. To above solution was added diiodomethane (Aldrich, 0.47 mL, 5.85 mmol) slowly through a syringe, and the reaction mixture was stirred under nitrogen at 0° C. for 10 minutes. Gradually a white slurry mixture was observed. To that mixture was added the solution of allyl alcohol derivative (68) and the chiral dioxaborolane (69) in dichloromethane. A clear solution was observed which then became gradually cloudy. The reaction mixture was stirred under nitrogen at a temperature of from 0° C. to room temperature for 15 hours. The reaction mixture was quenched by slowly adding saturated aqueous $NH_4Cl$. The product was extracted with dichloromethane, and the combined extracts were washed by saturated aqueous $NaHCO_3$ and brine, and dried over $Na_2SO_4$. After filtration and evaporation, the crude product was purified on a silica gel column eluting with hexane-ethyl acetate (from 4:1 to 1:1). The product (120 mg) obtained was contaminated with butylboronic acid. This mixture was dissolved in ether (10 mL). To the ether solution was added 2N NaOH solution (3 mL), and the mixture was stirred at room temperature overnight. The layers were separated, and the organic layer was washed with brine and dried over $Na_2SO_4$. After filtration, evaporation and high vacuum dry, a clean colorless oily product (70) was obtained (100 mg, 40% yield). TLC $R_f$ 0.23 (Hexane: EtOAc 1:1); $^1$H-NMR (400 MHz, $CDCl_3$): δ 7.59 (d, 2H, J 7.8 Hz), 7.37 (d, 2H, J 7.8 Hz) 3.53 (m, 1H), 3.46 (m, 1H), 2.66 (m, 2H), 1.25 (t, 1H, J 5.5 Hz), 1.04 (m, 1H), 0.93 (m, 1H), 0.53 (m, 2H).

Example 55

Preparation of (71)

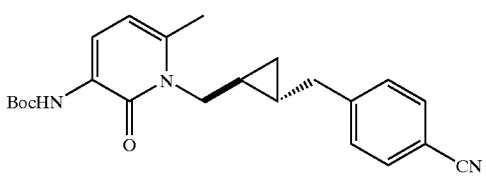

To a solution of the cyclopropane alcohol from Example 54 (compound 70, 108 mg, 0.58 mmol), compound 57 (257.9 mg, 1.15 mmol), and triphenylphosphine (Fluka, 301.6 mg, 1.15 mmol) in anhydrous THF (3 mL), was added diethyl azodicarboxylate (Fluka, 0.18 mL, 1.15 mmol) at 0° C. under nitrogen. The solution was stirred at 0° C. for 10 minutes and at room temperature for 30 minutes under nitrogen. The reaction was quenched by adding ethanol. After evaporation of solvents, the residue was purified on a silica gel column eluting with hexane-ethyl acetate (from 5:1 to 2:1). A solid product (71) was obtained as a foam (54 mg, 24% yield). TLC $R_f$ 0.64 (Hexane: EtOAc 1:1); $^1$H-NMR (400 MHz, CDCl$_3$): δ 7.83 (bd, 1H, J 7.6 Hz), 7.53 (bs, 1H), 7.48 (d, 2H, J 8.9 Hz), 7.19 (d, 2H, J 8.9 Hz), 6.00 (d, 1H, J 7.6 Hz), 4.03 (m, 2H), 2.71 (dd, 1H, J 15.3 Hz, J 6.3 Hz), 2.71 (dd, 1H, J 15.3 Hz, J 7.8 Hz), 2.28 (s, 3H), 1.51 (s, 9H), 1.20 (m, 1H), 1.07 (m, 1H), 0.93 (m, 1H), 0.75 (m, 1H).

Example 56

Preparation of (72)

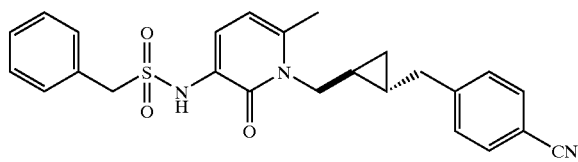

Compound 71 (54 mg, 0.14 mmol) was dissolved in a freshly prepared 4M solution of hydrogen chloride in ethyl acetate (hydrogen chloride was produced from acetyl chloride and ethanol) and the solution was stirred at room temperature for three hours. After removal of hydrogen chloride by evaporation, the residue was dissolved in acetonitrile (1.5 mL) and to that solution was added 2,4,6-collidine (Aldrich, 0.1 mL) to adjust the pH=8. To that solution was added α-toluenesulfonyl chloride (Aldrich, 39.8 mg, 0.16 mmol) and the mixture was stirred at room temperature under nitrogen for 4 hours. The mixture was diluted with ethyl acetate, washed with 1M KHSO$_4$ solution, saturated aqueous NaHCO$_3$ and brine, and then dried over Na$_2$SO$_4$. After filtration and evaporation, the crude products were purified on a silica gel column eluting with hexane-ethyl acetate (from 4:1 to 1:1). The first fraction was compound 72 (6.0 mg, 9.6% yield) which was obtained as a white foaming solid. $^1$H-NMR (400 MHz, CDCl$_3$): 7.51 (d, 2H, J 7.6 Hz), 7.31–7.18 (m, 9H), 5.92 (d, 1H, J 7.6 Hz), 4.31 (s, 2H), 4.04 (m, 2H), 2.69 (dd, 1H, J 15.0 Hz, J 6.7 Hz), 2.49 (dd, 1H, J 15.0 Hz, J 7.3 Hz), 2.30 (s, 3H), 1.20 (m, 1H), 1.07 (m, 1H), 0.87 (m, 1H), 0.56 (m, 1H).

Example 57

Preparation of (74)

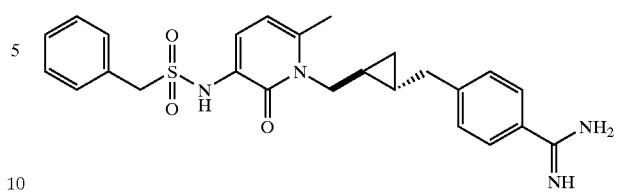

To a solution of compound 72 (6.0 mg, 0.013 mmol) in ethanol (1 mL) was added hydroxylamine hydrochloride (Aldrich, 1.8 mg, 0.026 mmol) and triethylamine (Fluka, 0.005 mL, 0.039 mmol). The reaction mixture was stirred under nitrogen at 60° C. overnight. The solvent was evaporated and the residue was dissolved in ethyl acetate. The organic solution was washed with water and dried over Na$_2$SO$_4$. After filtration and evaporation, crude product compound 73 (7.0 mg) was obtained which was used for the next step without further purification.

To a solution of compound 73 in acetic acid (1 mL) and water (0.25 mL) was added freshly activated zinc dust. The reduction was monitored using Mass Spectrum to determine completion. The reaction mixture was diluted with ethyl acetate, washed with water, saturated aqueous NaHCO$_3$ and brine, and dried over Na$_2$SO$_4$. After filtration and evaporation, a crude product was obtained which was purified using reversed phase preparatory HPLC eluting with an acetonitrile-0.1% TFA/water system. The pure fractions were concentrated and lyophilized to give compound 74 (1.3 mg, 96% purity, 97% ee). The enantiomeric excess of compound 72 was determined by reversed phase chiral HPLC analysis (chiral column: CHIRALCEL OD-R, lot No. 597-007-60416 from Chiral Technologies, Inc.). $^1$H-NMR (400 MHz, CD$_3$OD): δ 7.59 (d, 2H, J 8.2 Hz), 7.30–7.26 (m, 7H), 7.09 (d, 1H, J 7.6 Hz), 5.98 (d, 1H, J 7.6 Hz), 4.40 (s, 2H), ), 4.13 (dd, 1H, J 14.0 Hz, J 5.4 Hz), 3.93 (dd, 1H, J 14.0 Hz, J 8.5 Hz), 2.88 (dd, 1H, J 14.6 Hz, J 5.3 Hz), 2.33 (s, 3H), 2.28 (dd, 1H, J 14.6 Hz, J 8.7 Hz), 1.24 (m, 1H), 1.17 (m, 1H), 0.74 (m, 1H), 0.62 (m, 1H).

Figure 10:
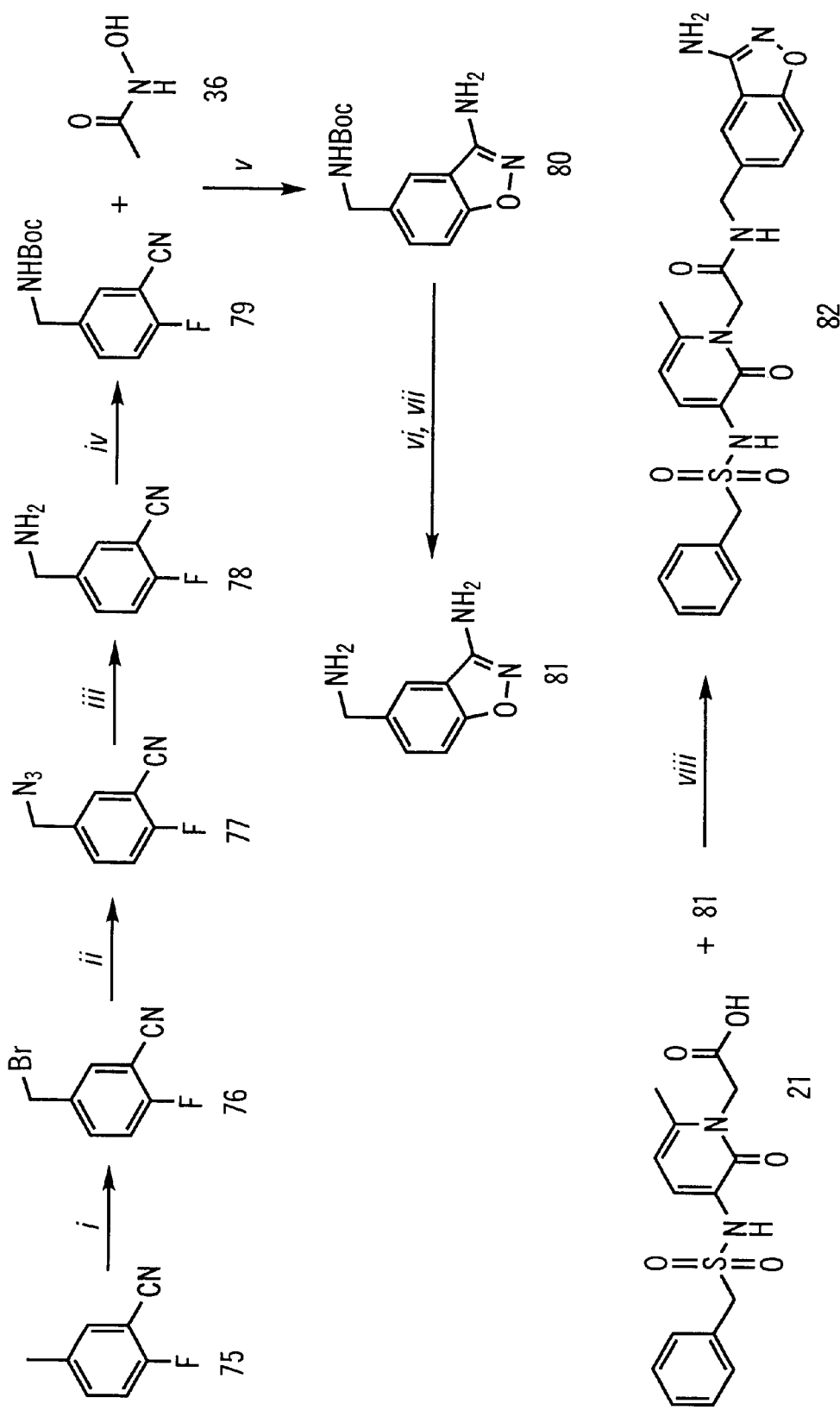
FIG. 10 depicts a reaction scheme for the synthesis of a compound having thrombin inhibitory activity. In this figure, "i" through "viii" are defined as: i) NBS, AIBN, CCl$_4$, reflux 8 hours; ii) NaN$_3$, DMF, room temperature 15 hours; iii) Ph$_3$P, THF, 0° C., 0° C. to room temperature 15 hours; iv) Boc$_2$O, DCM, room temperature 2 hours; v) t-BuOK, DMF, room temperature 15 hours; vi) 2N HCl, methanol/dioxane, room temperature 5 hours; vii) OH$^-$ resin; and viii) HOAt, EDC, DMF, room temperature 15 hours. These procedures are described more fully in Examples 58 to 64.

J. Preparation of Compound 82 (FIG. 10) Examples 58 to 64

Example 58

Preparation of (76)

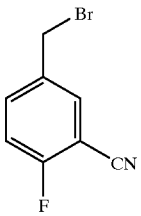

To a solution of 3-cyano-4-fluorotoluene (75) (Aldrich, 20.00 g, 148.0 mmol) in carbon tetrachloride (600 mL), were added NBS (Aldrich, 28.98 g, 162.8 mmol) and AIBN (Aldrich, 2.43 g, 14.8 mmol). The reaction mixture was degassed and charged with nitrogen three times, and then was refluxed at 85° C. for 8 hours. After standing at room temperature overnight, the mixture was filtered to remove solids and the solid by-product was washed by CCl$_4$. The filtrate was evaporated and purified on a silica gel column eluting with hexane-EtOAc (20:1). The product (Compound 76, 18.67 g, 59% yield) was obtained as a light yellow liquid which solidified after standing at room temperature. TLC $R_f$ 0.44 (hexane:EtOAc 10:1); $^1$H-NMR (400 MHz, CDCl$_3$): δ 7.66–7.61 (m, 2H), 7.20 (t, 1H, J 8.5 Hz), 4.44 (s, 2H).

Example 59

Preparation of (77)

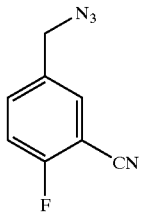

To the solution of α-bromo-3-cyano-4-fluorotoluene (compound 76, 18.67 g, 87.23 mmol) in DMF (200 mL) was added sodium azide (Aldrich, 6.80 g, 104.67 mmol). The reaction mixture was stirred at room temperature under nitrogen for 15 hours, and then poured into water (300 mL). The product was extracted with ether and the combined extracts were washed with brine three times and then dried over Na$_2$SO$_4$. After filtration, evaporation and high vacuum dry, a light yellow liquid product (compound 77, 15.31 g, 100% yield) was obtained which was used for the next step without further purification. TLC R$_f$ 0.47 (hexane:EtOAc 10:1); $^1$H-NMR (400 MHz, CDCl$_3$): δ 7.59–7.54 (m, 2H), 7.24 (t, 1H, J 8.4 Hz), 4.39 (s, 2H)

Example 60

Preparation of (78)

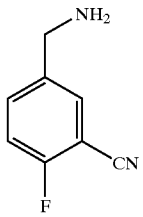

To the solution of α-azido-3-cyano-4-fluorotoluene (compound 77, 12.82 g, 74.45 mmol) in THF (348 mL) and water (16 mL) was added triphenylphosphine (Aldrich, 21.00 g, 80.05 mmol) slowly at 0° C. The mixture was stirred at a temperature of from 0° C. to room temperature for 15 hours, and then the solvents were evaporated. The residue was dissolved in 0.25 M HCl (300 mL, 75 mmol). The aqueous solution was washed with EtOAc until no UV active compounds were detected, adjusted to pH=10 with a 2M NaOH solution, and then extracted with dichloromethane. The combined extracts were dried over Na$_2$SO$_4$. After filtration, evaporation and high vacuum dry, a light yellow liquid product (9.25 g, 85% yield) was obtained which was used for the next step without further purification. $^1$H-NMR (400 MHz, CDCl$_3$): δ 7.60 (d, 1H, J 6.1 Hz), 7.56 (m, 1H), 7.16 (t, 1H, J 8.5 Hz), 3.89 (s, 2H), 1.44 (bs, 2H).

Example 61

Preparation of (79)

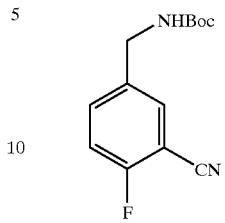

To a solution of α-amino-3-cyano-4-fluorotoluene (compound 78, 9.25 g, 63.27 mmol) in dichloromethane (316 mL), was added (Boc)$_2$O (Fluka, 15.19 g, 69.60 mmol). The mixture was stirred at room temperature for 2 hours. After evaporation of the solvent, the residue was purified on a silica gel column eluting with hexane-EtOAc (5:1 and 4:1) to provide a white crystalline solid product (13.10 g, 83% yield). TLC R$_f$ 0.27 (hexane:EtOAc 3:1); $^1$H-NMR (400 MHz, CDCl$_3$): δ 7.54–7.50 (m, 2H), 7.17 (t, 1H, J 8.7 Hz), 4.99 (bs, 1H), 4.29 (bd, 2H, J 5.8 Hz), 1.45 (s, 9H).

Example 62

Preparation of (80)

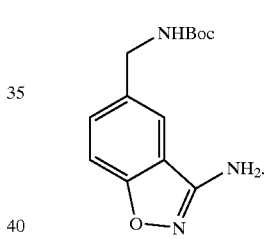

This procedure was developed in our laboratory based on a literature reference for making a desired bicyclic benzisoxazole ring (M. G. Palermo, Tetrahedron Lett. 37 (17), 1996, 2885–2886).

To a solution of acetohydroxamic acid (36) (227.5 mg, 3.0 mmol) in anhydrous DMF (4 mL) was added t-BuOK (Aldrich, 336.7 mg, 3.0 mmol). The mixture was stirred at room temperature under nitrogen for 15 minutes to obtain a gel-like suspension. To that mixture, was added compound 79 (500.6 mg, 2.0 mmol). The reaction mixture was stirred at room temperature under nitrogen for 15 hours. The mixture was poured into water and extracted with EtOAc. The combined extracts were washed with brine five times and dried over Na$_2$SO$_4$. After filtration and evaporation, the crude product was purified on a silica gel column eluting with hexane-EtOAc (from 4:1 to 1:1). Some starting material, acetohydroxamic acid (310 mg, 1.24 mmol, 62%), was recovered. The product (80) was obtained as a white solid (184 mg, 35% yield, 92% yield based on the recovered starting material). TLC R$_f$ 0.09 (hexane:EtOAc 3:1); $^1$H-NMR (400 MHz, CDCl$_3$): δ 7.45 (s, 1H), 7.43 (d, 1H, J 8.5 Hz), 7.38 (d, 1H, J 8.5 Hz), 4.93 (bs, 1H), 4.39 (bd, 4H, J 5.5 Hz), 1.46 (s, 9H).

Example 63

Preparation of (81)

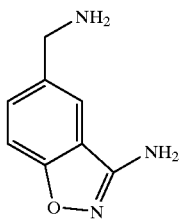

Compound 80 (178 mg, 0.68 mmol) was dissolved in 2M HCl methanol/dioxane (1:1) (10 mL). The reaction mixture was stirred at room temperature for 5 hours and a voluminous white precipitate formed. After evaporation of solvent and co-evaporation with dichloromethane, the residue was suspended in methanol (20 mL). To that mixture was added hydroxide form basic resin (AG 1-X8 Resin from Bio-Rad Laboratories) to make a clear solution and adjust the pH to about 10. The resin was filtered and washed with methanol thoroughly. The methanol solution was evaporated and the residue was dried under high vacuum to provide the free amine compound 81 as a white solid (111 mg, 100% yield). $^1$H-NMR (400 MHz, CDCl$_3$): δ 7.51 (s, 1H), 7.47 (d, 1H, J 8.8 Hz), 7.39 (d, 1H, J 8.5 Hz), 4.34 (bs, 2H), 3.99 (s, 4H, J 5.5 Hz).

Example 64

Preparation of (82)

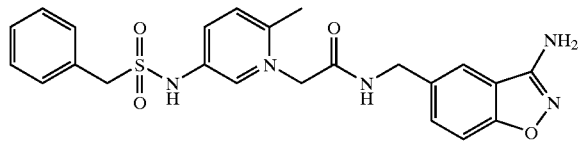

To a solution of 3-benzylsulfonylamino-6-methyl-1-methylenecarboxy-2-pyridinone (compound 21, 228.8 mg, 0.68 mmol) in DMF (3.4 mL), were added HOAt (Nova, 102.1 mg, 0.75 mmol), EDC (Nova, 143.8 mg, 0.75 mmol) and amine compound 81 (111 mg, 0.68 mmol). The reaction mixture was stirred under nitrogen at room temperature for 15 hours, and then poured into water (50 mL). The product was extracted with EtOAc, and the combined extracts were washed with saturated aqueous NaHCO$_3$ and dried over Na$_2$SO$_4$. After filtration and evaporation, the residue was purified using reversed phase preparatory HPLC eluting with an acetonitrile-0.1% TFA in water system. The pure fractions were concentrated and lyophilized to provide a white solid product (compound 82, 163 mg, 98% purity, 50% yield). MS: m/e 482.2 (M+H)$^+$, 963.4 (2M+H)$^+$; $^1$H-NMR (400 MHz, CD$_3$OD): δ7.70 (s, 1H), 7.49 (dd, 1H, J 8.5 Hz, J 1.5 Hz), 7.33–7.20 (m, 7H), 6.14 (d, 1H, J 7.6 Hz), 4.84 (s, 2H), 4.51 (s, 2H), 4.40 (s, 2H), 2.31 (s, 3H).

Figure 11:
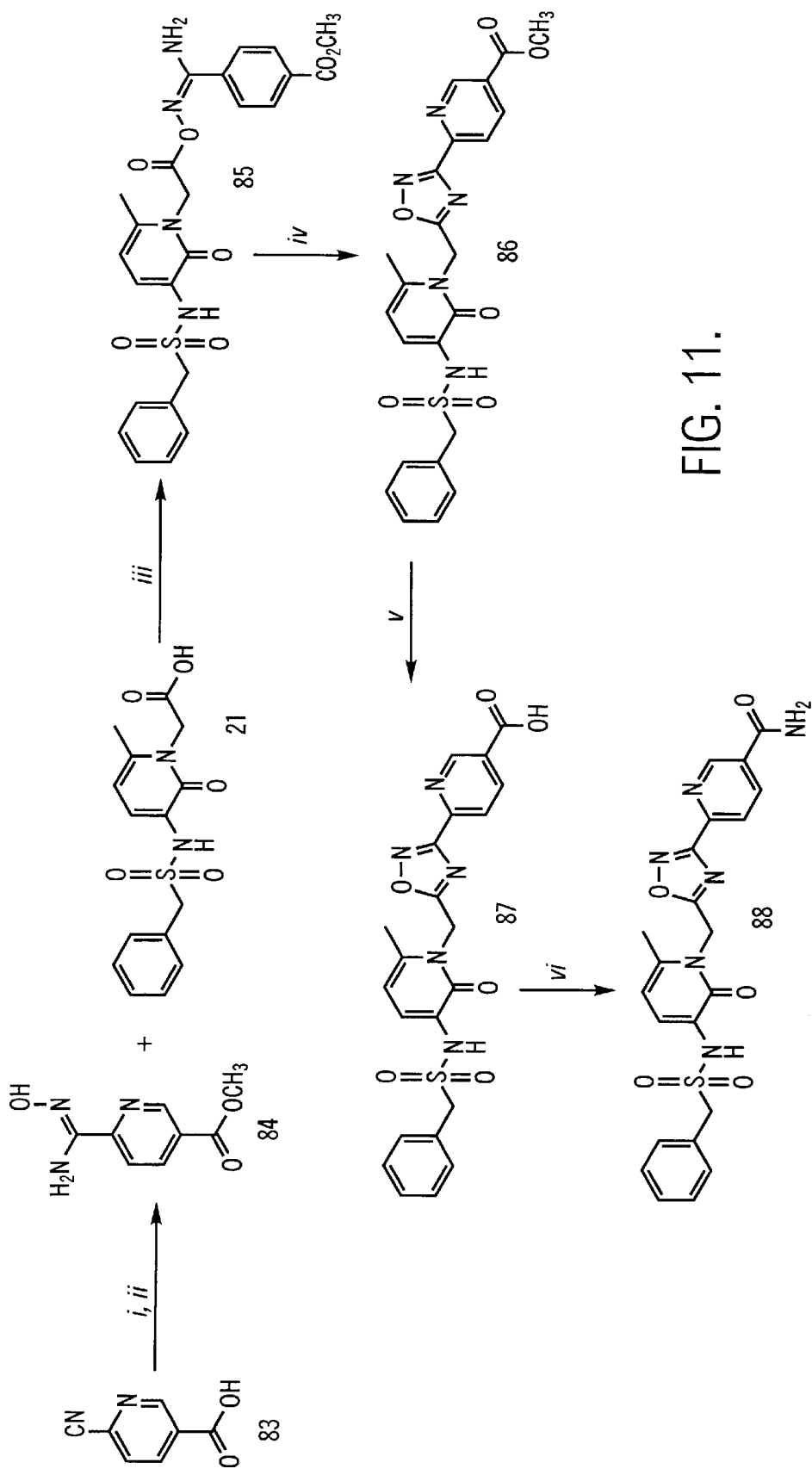
FIG. 11 depicts a reaction scheme for the synthesis of a compound having thrombin inhibitory activity. In this figure, "ii" through "vi" are defined as follows: i) hydroxylamine HCl, Et$_3$N, ethanol, room temperature 2 days; ii) methanol (anhydrous), acetylchloride, reflux 2 hours; iii) HOAt, EDC, DMF, room temperature 15 hours; iv) pyridine, reflux 3 hours; v) LiOH.H$_2$O methanol/water, room temperature 10 hours; and vi) HOAt, EDC, NH$_4$Cl, Et$_3$N, DMF, room temperature 15 hours. These procedures are more fully described in Examples 65 to 69.

K. Preparation of Compound 88 (FIG. 11) Examples 65 to 69

Example 65

Preparation of (84)

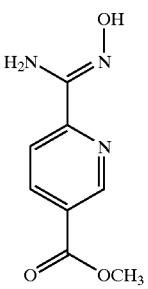

To a solution of 2-cyanopyridine-5-carboxylic acid (83) (Aldrich, 1.00 g, 6.75 mmol) in ethanol (30 mL) was added hydroxylamine hydrochloride (Aldrich, 514.2 mg, 7.40 mmol) and triethylamine (Aldrich, 1.29 mL, 9.26 mmol). The reaction mixture was stirred at room temperature for two days. Solvent was evaporated and the residue was dissolved in anhydrous methanol (20 mL). To that solution was added acetyl chloride (1 mL) carefully and the mixture was refluxed for 2 hours. After evaporation of the solvents, the residue was washed by dichloromethane, saturated aqueous NaHCO$_3$, water, methanol and ether, and dried under high vacuum. A pure product 84 (532 mg, 49% yield) was obtained. $^1$H NMR (400 MHz, CD$_3$OD): δ 9.10 (s, 1H), 8.28 (dd, 1H, J 8.5 Hz, J 1.5 Hz), 7.97 (d, 1H, J 8.5 Hz), 3.93 (s, 3H).

Example 66

Preparation of (85)

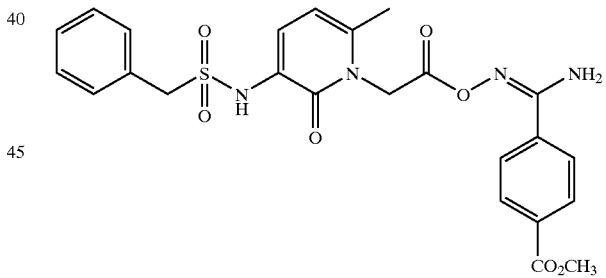

To a solution of 3-benzylsulfonylamino-6-methyl-1-methylenecarboxy-2-pyridinone (compound 21, 336.4 mg, 1 mmol) in DMF (5 mL), were added HOAt (Nova, 149.7 mg, 1.1 mmol), EDC (Nova, 210.9 mg, 1.1 mmol) and compound 84 (195.2 mg, 1 mmol). The reaction mixture was stirred under nitrogen at room temperature for 15 hours. A voluminous white precipitate was formed, which could not be dissolved in EtOAc and dichloromethane. To the reaction mixture was added water (100 mL) and the mixture was filtered, washed with water, saturated aqueous NaHCO$_3$, water and ether. After drying under high vacuum, a white solid product compound 85 (467 mg, 93% yield) was obtained. $^1$H NMR (400 MHz, CDCl$_3$): δ 9.20 (s, 1H), 8.36 (dd, 1H, J 8.2 Hz, J 1.5 Hz), 8.21 (d, 1H, J 8.2 Hz), 7.34 (d, 1H, J 7.6 Hz), 7.31–7.26 (m, 5H), 6.06 (d, 1H, J 7.6 Hz), 5.06 (s, 2H), 4.34 (s, 2H), 3.93 (s, 3H), 2.37 (s, 3H).

Example 67
Preparation of (86)

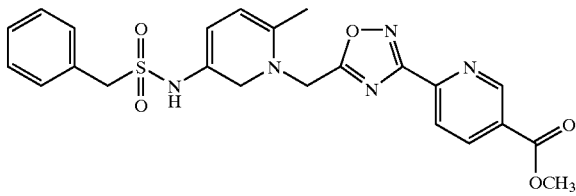

A mixture of compound 85 (460 mg, 0.90 mmol) in pyridine (10 mL) was refluxed under nitrogen for 3 hours; then the pyridine solvent was evaporated. The residue was washed with methanol and ether to provide an off-white solid product (86) (375 mg, 84% yield). MS: m/e 496 (M+H)$^+$, $^1$H NMR (400 MHz, CDCl$_3$): δ 9.34 (d, 1H, J 1.5 Hz), 8.42 (dd, 1H, J 8.2 Hz, J 1.5 Hz), 8.20 (d, 1H, J 8.2 Hz), 7.33–7.20 (m, 6H), 6.07 (d, 1H, J 7.6 Hz), 5.63 (s, 2H), 4.36 (s, 2H), 3.99 (s, 3H), 2.41 (s, 3H).

Example 68
Preparation of (87)

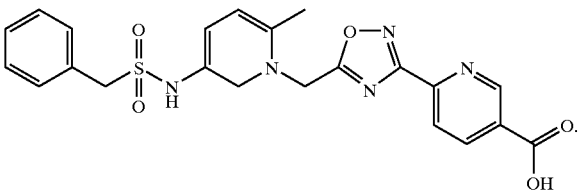

To a suspension of compound 86 (370 mg, 0.75 mmol) in methanol (6 mL) and water (2 mL), was added lithium hydroxide monohydrate (156.7 mg, 3.73 mmol). The reaction mixture was stirred at room temperature for 10 minutes and a clear solution was obtained. The solution was neutralized to pH=7 with 0.5 M HCl and concentrated. The residue was purified using reversed phase preparatory HPLC eluting with an acetonitrile-0.1% TFA in water system. The pure fractions were concentrated and lyophilized to provide product compound 87 as a white solid (340 mg, 94% yield). $^1$H NMR (400 MHz, CD$_3$OD): δ 9.15 (d, 1H, J 1.5 Hz), 8.37 (dd, 1H, J 8.2 Hz, J 1.5 Hz), 8.09 (d, 1H, J 8.2 Hz), 7.34–7.20 (m, 6H), 6.18 (d, 1H, J 7.6 Hz), 5.65 (s, 2H), 4.40 (s, 2H), 2.45 (s, 3H).

Example 69
Preparation of (88)

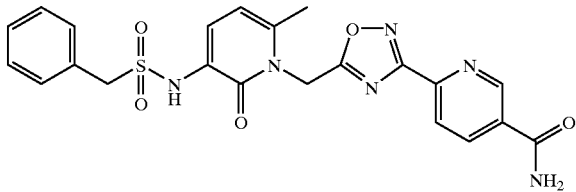

To a solution of compound 87 (120 mg, 0.25 mmol) in DMF (2 mL), were added HOAt (Nova, 40.8 mg, 0.30 mmol), EDC (Nova, 57.5 mg, 0.30 mmol), ammonium chloride (Aldrich, 66.8 mg, 1.25 mmol) and triethylamine (Aldrich, 0.21 ml, 1.50 mmol). The reaction mixture was stirred under nitrogen at room temperature for 15 hours. HPLC showed only 30% product formed and 67% of compound 87 was still in the reaction mixture. Additional ammonium chloride and triethylamine were added to the reaction flask, and the reaction mixture was stirred for another day, but the same ratio of starting material and product was observed. The solution was diluted with water (20 mL) and purified using reversed phase preparatory HPLC eluting with an acetonitrile-0.1% TFA in water system. The pure fractions were concentrated and lyophilized to provide product compound 88 as a white solid (7 mg, 100% purity). MS: m/e 481 (M+H)$^+$; $^1$H NMR (400 MHz, CD$_3$OD): δ 9.09 (s, 1H), 8.36 (dd, 1H, J 8.2 Hz, J 2.1 Hz), 8.19 (d, 1H, J 8.2 Hz), 7.33 (d, 1H, J 7.6 Hz), 7.28–7.20 (m, 5H), 6.19 (d, 1H, J 7.6 Hz), 5.66 (s, 2H), 4.40 (s, 2H), 2.45 (s, 3H).

L. Preparation of Compound 91 (FIG. 12) Examples 70 to 72

Example 70
Preparation of (89)

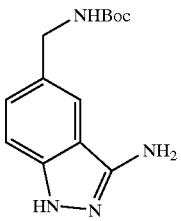

To a solution of compound 79 (10.0 g, 39.96 mmol) in n-butanol (200 mL) was added hydrazine (Aldrich, 2.63 mL, 83.91 mmol). The reaction mixture was refluxed under nitrogen for 22 hours. After evaporation of n-butanol, the residue was purified on a silica gel column eluting with 5% to 10% methanol in dichloromethane to provide a white crystalline solid product (compound 89, 5.47 g, 52% yield). TLC R$_f$ 0.26 (5% MeOH in CH$_2$Cl$_2$); $^1$H-NMR (400 MHz, CDCl$_3$): δ 8.94 (bs, 1H), 7.46 (s, 1H), 7.30–7.27 (m, 2H), 4.87 (bs, 1H), 4.38 (bd, 2H, J 5.5 Hz), 4.09 (bs, 2H), 1.47 (s, 9H).

Example 71
Preparation of (90)

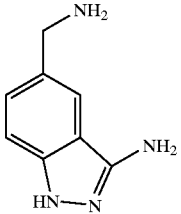

Compound 89 (2.47 g) was dissolved in 2M HCl dioxane solution. The reaction mixture was stirred at room temperature for 3 hours. After evaporation of solvent, co-evaporation with dichloromethane and high vacuum dry, an off-white solid product (compound 90, 2.27 g, 99% yield) was obtained. $^1$H-NMR (400 MHz, D$_2$O): δ 7.85 (s, 1H), 7.59 (d, 1H, J 8.8 Hz), 7.52 (d, 1H, J 8.8 Hz), 4.25 (s, 2H).

To a solution of compound 90 (2.00 g, 7.36 mmol) in methanol was added hydroxide form basic resin (AG 1-X8 Resin from Bio-Rad Laboratories) to adjust the pH to about 10. After filtration, the resin was washed by methanol thoroughly. The methanol solution was evaporated and the residue was dried under high vacuum to provide the free amine form of compound 90 as a yellow solid (1.15 g, 96% yield).

Example 72

Preparation of (91)

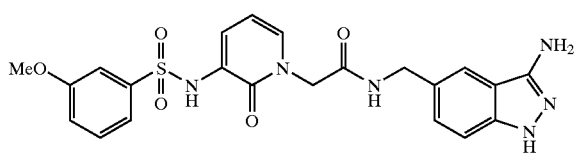

To a solution of compound 32 (676.7 mg, 2.00 mmol) in DMF (8 mL) were added HOAt (Fluka, 326.7 mg, 2.40 mmol), EDC (Fluka, 474.5 mg, 2.40 mmol) and compound 90 (389.3 mg, 2.40 mmol). The reaction mixture was stirred under nitrogen at room temperature for 15 hours, and then poured into water (100 mL). The product precipitated out of the aqueous solution and was collected by filtration. The product was purified again using reversed phase preparatory HPLC eluting with an acetonitrile-0.1% TFA in water system. The pure fractions were concentrated and lyophilized to provide a white solid product 91 (64 mg, 100% purity). MS: m/e 483.2 (M+H)$^+$; $^1$H-NMR (400 MHz, CD$_3$OD): δ 7.76 (s, 1H), 7.54 (dd, 1H, J 7.3 Hz, J 1.5 Hz), 7.50 (d, 1H, J 8.8 Hz), 7.38–7.30 (m, 4H), 7.26 (dd, 1H, J 6.9 Hz, J 1.7 Hz), 7.05 (dd, 1H, J 7.5 Hz, J 1.7 Hz), 6.27 (dd, 1H, J 6.9 Hz, J 7.5 Hz), 4.61 (s, 2H), 4.44 (s, 2H), 3.74 (s, 3H).

Figure 13:
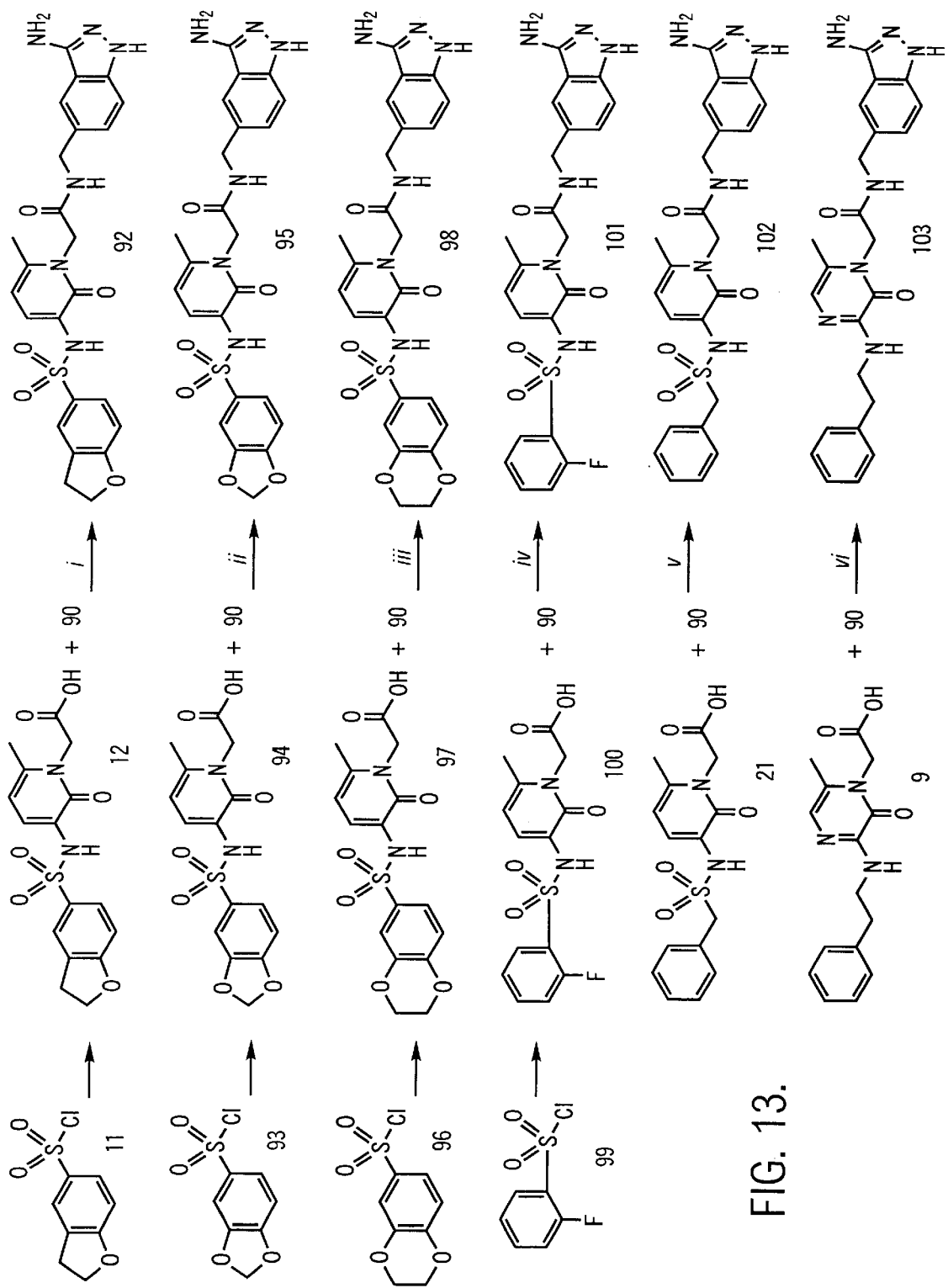
FIG. 13 depicts reaction schemes for the synthesis of compounds having thrombin inhibitory activity which have a 3-aminoindazole at P1. In this figure, "i" through "vi" are defined as follows: i) EDC, HOAt, NMM, DMF, room temperature 16 hours; ii) EDC, HOAt, NMM, DMF, room temperature 13 hours; iii) EDC, HOAt, NMM, DMF, room temperature 13 hours; iv) EDC, HOAt, NMM, DMF, room temperature 16 hours; v) EDC, HOAt, NMM, DMF, room temperature 13 hours; and vi) EDC, HOAt, NMM, DMF, room temperature 13 hours. These procedures are more fully described in Examples 73 to 78.

M. Preparation of other Compounds with a 3-Aminoindazole at P1 (FIG. 13)—Examples 73 to 78

Example 73

Preparation of (92)

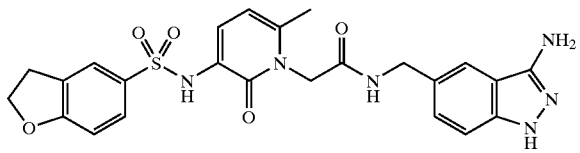

A solution of compound 12 (260 mg, 0.5 mmol), 3-amino-5-(aminomethyl)indazole (compound 90, 150 mg, 1.0 mmol), 1-(3-dimethylaminopropyl)-3-ethylcarbodiimide hydrochloride (EDC, Nova, 200 mg, 1.0 mmol), 1-hydroxy-7-azabenzotriazole (HOAt, Nova, 136 mg, 1.0 mmol), and 4-methylorpholine (NMM, Aldrich, 10.6 mL, 3.5 mmol) in DMF (10 mL) was stirred at room temperature. After 16 hours, the reaction mixture was diluted with water, filtered through a 2 micro-filter, and purified using reversed phase preparatory HPLC eluting with an acetonitrile-0.1% of TFA in water system. Those fractions of >90% purity were combined and concentrated. Lyophilization under high vacuum (0.1 mm Hg) for 48 hours afforded a white solid (compound 92, 110 mg, 31%). MS (electrospray) 509 (M+1); $^1$H NMR (CD$_3$OD): δ 2.20 (s, 3H), 3.22 (t, 2H, J=7.2 Hz), 4.38 (t, 2H, J=7.2 Hz), 4.40 (s, 2H), 4.65 (s, 2H), 6.10 (d, 1H, J=8.2 Hz), 6.58 (d, 1H, J=8.2 Hz), 7.26 (d, 1H, J=8.2 Hz), 7.35 (d, 1H, J=8.2 Hz), 7.42 (d, 1H, J=8.2 Hz), 7.48 (m, 1H), 7.66 (s, 1H).

Example 74

Preparation of (95)

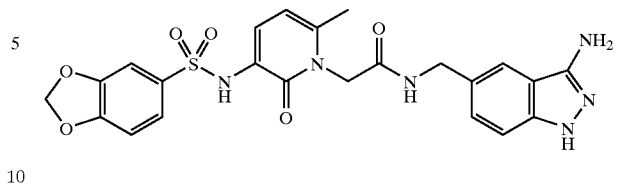

Intermediate 93 was synthesized using the procedures described for synthesizing compound 11 (see Example 9), substituting 1,3-benzodioxole for 2,3-dihydrobenzofuran. Intermediate 93 was converted to compound 94 using the same reaction sequences described in Examples 10 and 11.

A solution of compound 94 (500 mg, 1.4 mmol), 3-amino-5-(aminomethyl)indazole (compound 90, 262 mg, 1.6 mmol), 1-(3-dimethylaminopropyl)-3-ethylcarbodiimide hydrochloride (EDC, Nova, 345 mg, 1.8 mmol), 1-hydroxy-7-azabenzotriazole (HOAt, Nova, 250 mg, 1.8 mmol), and DIEA (Aldrich, 1.25 mL, 7.0 mmol) in DMF (10 mL) was stirred at room temperature. After 13 hours, the reaction mixture was diluted with water, filtered through a 2 micro-filter, and purified using reversed phase preparatory HPLC eluting with an acetonitrile-0.1% of TFA in water system. Those fractions of >90% purity were combined and concentrated. Lyophilization under high vacuum (0.1 mm Hg) for 48 hours afforded a white solid (compound 95, 117 mg, 16%). MS (electrospray) 511 (M+1); $^1$H NMR (CD$_3$OD): δ 2.25 (s, 3H), 4.45 (s, 2H), 4.75 (s, 2H), 5.96 (s, 1H), 6.20 (d, 1H, J=8.2 Hz), 6.80 (d, 1H, J=8.2 Hz), 7.23 (s, 1H), 7.35 (m, 1H), 7.42 (d, 1H, J=7.8 Hz), 7.48 (d, 1H, J=7.8 Hz), 7.78 (s, 1H).

Example 75

Preparation of 3-(1,4-benzodioxan-6-sulfonyl)-6-methyl-1-(3-amino-5-methylenecarboxamidomethylindazolyl)pyridinone (98)

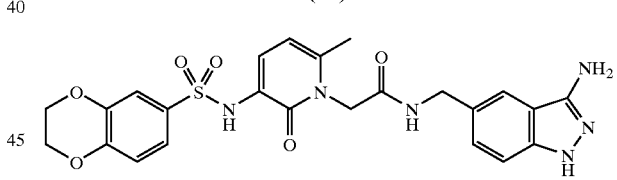

Intermediate 96 was synthesized using the procedures described for synthesizing compound 11 (see Example 9), substituting 1,4-benzodioxane for 2,3-dihydrobenzofuran. Intermediate 96 was converted to compound 97 using the reaction sequences described in Examples 10 and 11.

A solution of compound 97 (380 mg, 1.0 mmol), 3-amino-5-(aminomethyl)indazole (compound 90, 162 mg, 1.0 mmol), 1-(3-dimethylaminopropyl)-3-ethylcarbodiimide hydrochloride (EDC, Nova, 383 mg, 2.0 mmol), 1-hydroxy-7-azabenzotriazole (HOAt, Nova, 272 mg, 2.0 mmol), and 4-methylorpholine (NMM, Aldrich, 1.0 mL, 9.1 mmol) in DMF (10 mL) was stirred at room temperature. After 13 hours, the reaction mixture was diluted with water, filtered through a 2 micro-filter, and purified using reversed phase preparatory HPLC eluting with an acetonitrile-0.1% of TFA in water system. Those fractions of >90% purity were combined and concentrated. Lyophilization under high vacuum (0.1 mm Hg) for 48 hours afforded a white solid (compound 98, 242 mg, 46%). MS (electrospray) 525

(M+1); ¹H NMR (CD₃OD): δ 2.24 (s, 3H), 4.20 (m, 4H), 4.45 (d, 2H, J=3.5 Hz), 4.76 (s, 2H), 6.19 (d, 1H, J=7.8 Hz), 6.82 (d, 1H, J=7.8 Hz), 7.22 (d, 1H, J=7.8 Hz), 7.24 (s, 1H), 7.38 (d, 1H, J=7.6 Hz), 7.42 (d, 1H, J=7.8 Hz), 7.51 (d, 1H, J=7.6 Hz), 7.80 (s, 1H), 8.67 (br s, 1H).

Example 76

Preparation of (101)

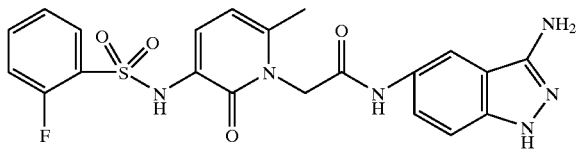

Compound 99 (Aldrich) was converted to intermediate 100 using the reaction sequences described in Examples 10 and 11.

A solution of compound 100 (355 mg, 0.7 mmol), 3-amino-5-(aminomethyl)indazole (compound 90, 150 mg, 0.9 mmol), 1-(3-dimethylaminopropyl)-3-ethylcarbodiimide hydrochloride (EDC, Nova, 383 mg, 2.0 mmol), 1-hydroxy-7-azabenzotriazole (HOAt, Nova, 272 mg, 2.0 mmol), and 4-methylorpholine (NMM, Aldrich, 1.0 mL, 9.1 mmol) in DMF (10 mL) was stirred at room temperature. After 16 hours, the reaction mixture was diluted with water, filtered through a 2 micro-filter, and purified using reversed phase preparatory HPLC eluting with an acetonitrile-0.1% of TFA in water system. Those fractions of >90% purity were combined and concentrated. Lyophilization under high vacuum (0.1 mm Hg) for 48 hours afforded a white solid (compound 101, 44 mg, 16%). MS (electrospray) 485 (M+1); ¹H NMR (CD₃OD): δ 2.35 (s, 3H), 4.45 (s, 2H), 4.75 (s, 2H), 6.15 (s, 1H), 7.20 (m, 2H), 7.40 (m, 2H), 7.55 (m, 2H), 7.78 (s, 1H), 7.82 (m, 1H).

Example 77

Preparation of (102)

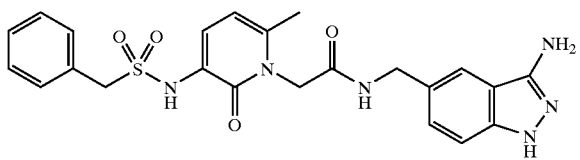

A solution of compound 21 (380 mg, 1.0 mmol), 3-amino-5-(aminomethyl)indazole (compound 90, 162 mg, 1.0 mmol), 1-(3-dimethylaminopropyl)-3-ethylcarbodiimide hydrochloride (EDC, Nova, 383 mg, 2.0 mmol), 1-hydroxy-7-azabenzotriazole (HOAt, Nova, 272 mg, 2.0 mmol), and 4-methylorpholine (NMM, Aldrich, 1.0 mL, 9.1 mmol) in DMF (10 mL) was stirred at room temperature. After 13 hours, the reaction mixture was diluted with water, filtered through a 2 micro-filter, and purified using reversed phase preparatory HPLC eluting with an acetonitrile-0.1% of TFA in water system. Those fractions of >90% purity were combined and concentrated. Lyophilization under high vacuum (0.1 mm Hg) for 48 hours afforded a white solid (compound 62, 109 mg, 56%). MS (electrospray) 481 (M+1); ¹H NMR (CD₃OD): δ 2.35 (s, 3H), 4.40 (s, 2H), 4.56 (s, 2H), 6.18 (d, 1H, J=7.8 Hz), 7.20 (m, 4H), 7.25 (m, 1H), 7.30 (d, 1H, J=7.8 Hz), 7.38 (d, 1H, J=7.8), 7.80 (s, 1H), 8.78 (br t, 1H, NH).

Example 78

Preparation of 3-(2-phenethylamino)-6-methyl-1-(3-amino-5-methylenecarboxamido-methylindazolyl) pyrazinone (103)

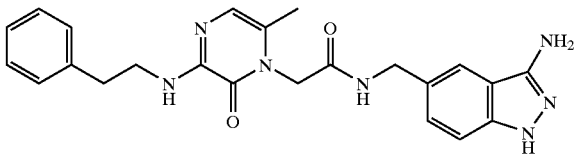

A solution of 3-(2-phenethylamino)-6-methyl-1-methylenecarboxypyrazinone (compound 9, 646 mg, 2.25 mmol), 3-amino-5-(aminomethyl)indazole (compound 90, 300 mg, 1.5 mmol), 1-(3-dimethylaminopropyl)-3-ethylcarbodiimide hydrochloride (EDC, Nova, 575 mg, 3.0 mmol), 1-hydroxy-7-azabenzotriazole (HOAt, Nova, 408 mg, 3.0 mmol), and 4-methylorpholine (NMM, Aldrich, 2.5 mL, 22 mmol) in DMF (10 mL) was stirred at room temperature. After 13 hours, the reaction mixture was diluted with water, filtered through a 2 micro-filter, and purified using reversed phase preparatory HPLC eluting with an acetonitrile-0.1% of TFA in water system. Those fractions of >90% purity were combined and concentrated. Lyophilization under high vacuum (0.1 mm Hg) for 48 hours afforded a white solid (compound 103, 332 mg, 51%). MS (electrospray) 432 (M+1); ¹H NMR (CD₃OD): δ 2.18 (s, 3H), 2.95 (t, 2H, J=7.2 Hz), 3.64 (t, 2H, J=7.2 Hz), 4.47 (s, 2H), 4.79 (s, 2H), 6.59 (s, 1H), 7.28 (m, 5H), 7.38 (d, 1H, J=7.3 Hz), 7.52 (d, 1H, J=7.3 Hz), 7.79 (s, 1H), 8.85 (br s, 1H).

N. Preparation of 5-(Aminomethyl)indazole Intermediate (110)—Examples 79 to 84 (FIG. 14)

Example 79

Preparation of 4-(hydroxymethyl)-2-methylaniline (105)

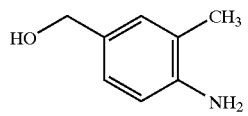

(Literature reference for making this compound see: Sun, J.-H.; Teleha, C. A.; Yan, J.-S.; Rodgers, J. D.; Nugiel, D. A. *J. Org. Chem.* 1997, 62, 5627–5629).

A solution of 3-methyl-4-nitrobenzyl alcohol (compound 104, 8.5 g, 50.9 mmol) in ethanol (100 mL) was stirred at room temperature, while 10% Pd/C (1.0 g) was added in one portion. The resulting suspension was hydrogenated (10 psi) in a Parr apparatus at room temperature for 1.5 hours. The catalyst was removed by filtration, and solvent was evaporated under vacuum to give the title compound (105, 6.9 g, 99%). MS (electrospray) 138 (M+1); ¹H N MR (CDCl₃) δ 2.16 (s, 3H), 2.72 (br s, 3H), 4.52 (s, 2H), 6.64 (d, 1H, J=8.0 Hz), 7.02 (d, 1H, J=8.0 Hz), 7.05 (s, 1H).

Use of high pressure (30 Psi) of hydrogen and a long reaction time (8 hours) resulted a hydrogenolysis product. The same starting material (104) (21.05 g, 126 mmol) yielded 2,4-dimethylaniline (15.20 g, 100%) under such conditions. MS (electrospray) 122 (M+1); ¹H N MR (CDCl₃) δ 2.14 (s, 3H), 2.23 (s, 3H), 3.72 (br s, 1H), 6.58 (d, 1H, J=8.0 Hz), 6.84 (d, 1H, J=8.0 Hz), 6.87 (s, 1H).

Example 80

Preparation of 1-acetyl-5-(acetoxymethyl)indazole (106)

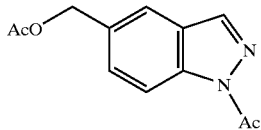

To a suspension of 2-methyl-4-(hydroxymethyl)aniline (compound 105, 4.0 g, 29 mmol) and potassium acetate (Aldrich, 8.6 g, 88 mmol) in chloroform (Calbiochem, 60 mL), was added acetic anhydride (Aldrich, 8.3 mL, 88 mmol) at room temperature, and the temperature was allowed to increase to 45° C. The mixture was then heated to reflux temperature for 2 hours under nitrogen. After cooling to room temperature, isoamylnitrite (Aldrich, 7.8 mL, 88 mmol) and 18-crown-6 (Aldrich, 1.5 g, 0.6 mmol) were added. The reaction mixture was heated at its reflux temperature for 28 hours. After returning to room temperature, the mixture was further treated with acetic anhydride (10 mL) and the solution was stirred at room temperature for 12 hours. The reaction mixture was diluted with methylene chloride (600 mL) and washed with saturated aqueous $NaHCO_3$ aqueous solution (300 mL), water (300 mL) and brine (50 mL). After drying ($Na_2SO_4$), the organic solvent was removed under vacuum to give a yellow oil which was purified by flash chromatography on silica gel (85:15 hexane-ethyl acetate) to yield the title compound (106, 6.21 g, 91%). TLC $R_f$ 0.45 (70:30 hexane-ethyl acetate); MS (electrospray) 233 (M+1); $^1$H N MR ($CDCl_3$) δ 2.12 (s, 3H), 2.79 (app d, 3H, J=0.4 Hz), 5.23 (s, 2H), 7.56 (dd, 1H, J=8.8, 1.6 Hz), 7.74 (t, 1H, J=0.8 Hz), 8.12 (s, 1H), 8.43 (dd, 1H, J=8.8, 0.6 Hz).

Example 81

Preparation of 5-(bromomethyl)-1H-indazole Hydrogen Bromide (107)

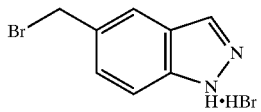

A suspension of 1-acetyl-5-(acetoxymethyl)indazole (106) (3.0 g, 13 mmol) in aqueous hydrobromic acid (15 mL, 226 mmol) was stirred at room temperature for 25 hours. The solid was collected on a Buchner funnel and dried under vacuum for 12 hours. The filtrate was stirred at room temperature for additional 24 hours and more solid was collected. After drying under vacuum, title compound was obtained as a yellow solid (107, 3.48 g, 92%) which was used in the next synthesis step without further purification. $^1$H NMR ($CDCl_3$) δ 4.88 (s, 2H), 7.43 (d, 1H, J=8.8), 7.56 (d, 1H, J=8.8 Hz), 7.87 (s, 1H), 8.10 (s, 1H).

Example 82

Preparation of 5-(bromomethyl)-1-(2-tetrahydropyranyl)indazole (108)

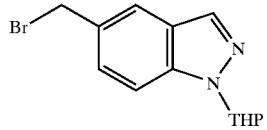

A yellow suspension of 5-(bromomethyl)-1H-indazole hydrogen bromide (compound 107, 3.0 g, 14 mmol) and 3,4-dihydro-2H-pyran (Aldrich, 2.4 g, 29 mmol) in THF (100 mL) was heated at reflux temperature for 2 hours. After cooling down to room temperature, the reaction mixture was stirred at room temperature for 12 hours under nitrogen. The reaction mixture was diluted with methylene chloride (250 mL), washed with saturated aqueous $NaHCO_3$, water and brine. After drying ($MgSO_4$), the solvent was removed under vacuum to give a yellow oil. Flash chromatography yielded the title compound (108, 3.34 g, 80%). TLC $R_f$ 0.58 (70:30 hexane-ethyl acetate); MS (electrospray) 295, 297 (M+1); $^1$H N MR ($CDCl_3$) δ 1.57–1.84 (m, 3H), 2.16 (m, 2H), 2.55 (m, 1H), 3.75 (m, 1H), 4.01 (m, 1H), 4.65 (s, 2H), 5.71 (d, 1H, J=9.2 Hz), 7.44 (d, 1H, J=8.8 Hz), 7.59 (d, 1H, J=8.8 Hz), 7.73 (s, 1H), 8.00 (s, 1H).

Example 83

Preparation of 5-(azidomethyl)-1-(2-tetrahydropyranyl)indazole (109)

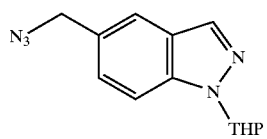

To a solution of 5-(bromomethyl)-1-(2-tetrahydropyranyl)indazole (compound 108, 3.0 g, 10.2 mmol) in DMF (30 mL), was added with sodium azide (Aldrich, 2.64 g, 40.6 mmol) in one portion. The suspension was heated at 90° C. for 30 minutes and a yellow solution formed. After cooling to room temperature, the reaction mixture was poured into water (100 mL) and extracted with ether (2×150 mL). Combined organic layers were washed with brine, then dried ($MgSO_4$). Evaporation of solvent gave the product (109) as a yellow oil (2.61 g, 99%). TLC $R_f$ 0.63 (60:40 hexane-ethyl acetate); MS (electrospray) 258 (M+1); $^1$H NMR ($CDCl_3$) δ2.03–2.15 (m, 2H), 2.55 (m, 1H), 3.72 (m, 1H), 4.02 (m, 1H), 4.52 (s, 1H), 5.71 (d, 1H, J=9.4 Hz), 7.32 (d, 1H, J=8.8 Hz), 7.56 (d, 1H, J=8.8 Hz), 7.63 (s, 1H), 8.00 (s, 1H).

Example 84

Preparation of 5-(aminomethyl)-1-(2-tetrahydropyranyl)indazole (110)

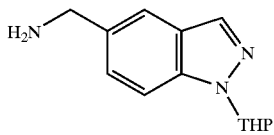

A solution of LiAlH₄ (Aldrich, 10.5 mL, 10.5 mmol, 1.0 M) in THF was added dropwise into a yellow solution of 5-(azidomethyl)-1-(2-tetrahydropyranyl)indazole (compound 109, 2.6 g, 10.1 mmol) in THF (30 mL) at 0° C. After stirring at 0° C. for 1 hour, NaOH (1.0M, 1.5 mL) was added. The reaction mixture was allowed to warm to room temperature. Ethyl acetate (100 mL) was added, and the suspension was filtered (Celite). The filter cake was washed with an addition portion of ethyl acetate (40 mL). Combined organic layers were evaporated under vacuum to give free amine 110 (2.14 g, 92%). MS (electrospray) 232.5 (M+1); $^1$H NMR (CDCl₃) δ 1.61 (m, 3H), 2.02 (m, 2H), 2.50 (m, 1H), 2.83 (br s, 2H), 3.68 (m, 1H), 3.85 (s, 2H), 3.95 (m, 1H), 5.62 (d, 1H, J=9.2 Hz), 7.29 (d, 1H, J=8.8 Hz), 7.48 (d, 1H, J=8.8 Hz), 7.53 (s, 1H), 7.92 (s, 1H).

Figure 15:
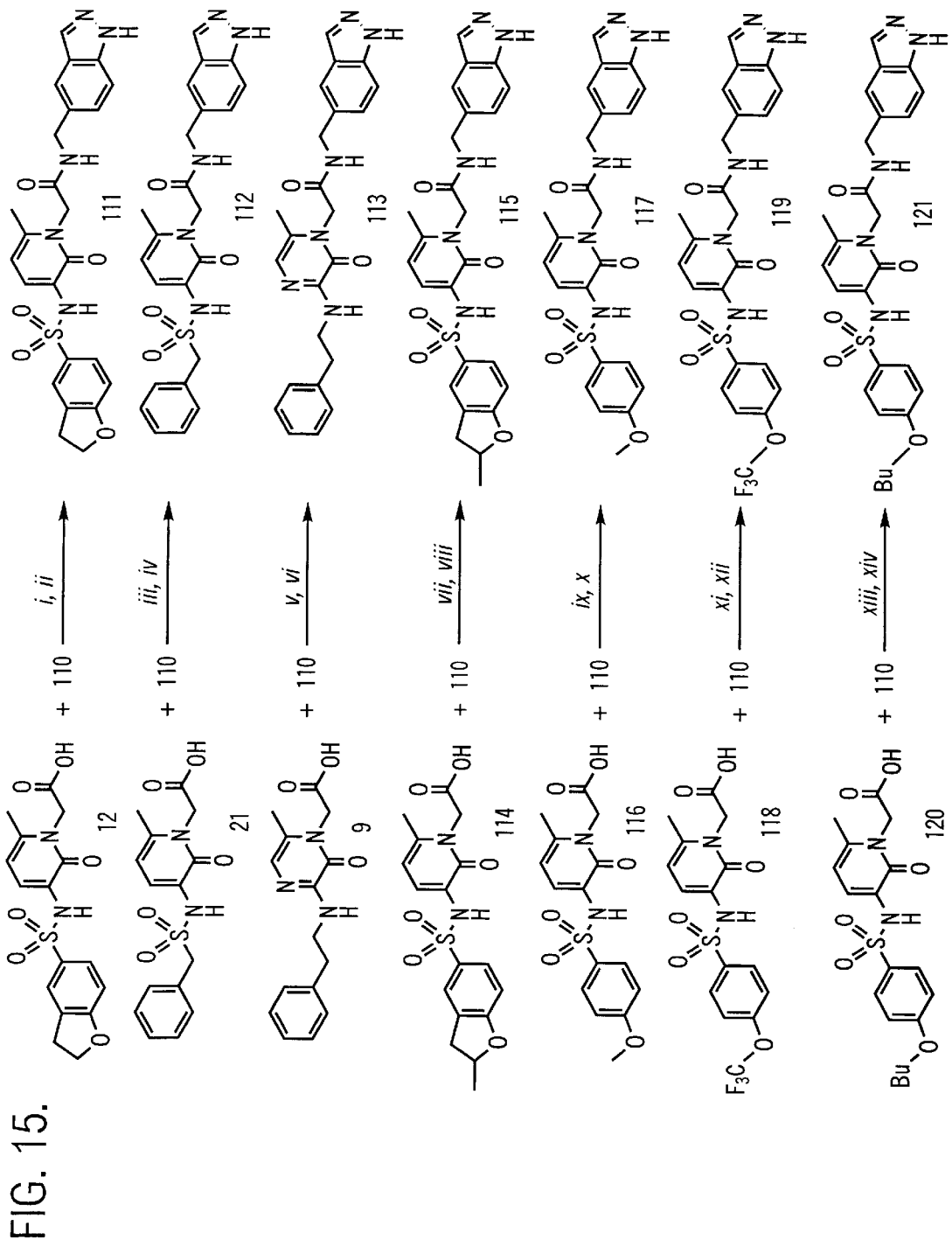
FIG. 15 depicts reaction schemes for the synthesis of compounds having thrombin inhibitory activity which have an indazole group as P1. In this figure, "i" through "xiv" are defined as follows: i) EDC, HOAt, NMM, DMF, room temperature 16 hours; ii) 4M HCl, dioxane, 60° C. 2 hours; iii) EDC, HOAt, NMM, DMF, room temperature 16 hours; iv) 4M HCl, dioxane, 60° C. 2 hours; v) EDC, HOAt, NMM, DMF, room temperature 16 hours; vi) 4M HCl, dioxane, 60° C. 2 hours; vii) EDC, HOAt, NMM, DMF, room temperature 16 hours; viii) 4M HCl, dioxane, 60° C. 2 hours; ix) EDC, HOAt, NMM, DMF, room temperature 16 hours; x) 4M HCl, dioxane, 60° C. 2 hours; xi) EDC, HOAt, NMM, OMF, room temperature 16 hours; xii) 4M HCl, dioxane, 60° C. 2 hours; xiii) EDC, HOAt, NMM, DMF, room temperature 16 hours; and xiv) 4M HCl, dioxane, 60° C. 2 hours. These procedures are more fully described in Examples 85 to 91.

O. Synthesis of Certain Compounds with Indazole as P1 (FIG. 15)—Examples 85 to 91

Example 85

Preparation of (111)

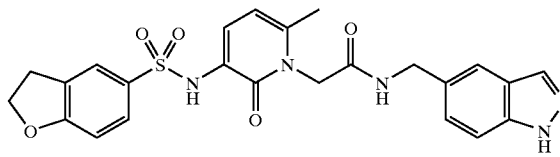

A solution of compound 12 (646 mg, 2.25 mmol), compound 110 (300 mg, 1.5 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase preparatory HPLC eluting with an acetonitrile-0.1% of TFA in water system. Those fractions of >95% purity were combined and concentrated. Lyophilization under high vacuum (0.1 mm Hg) afforded the product (111) as a white solid (332 mg, 51%). MS (electrospray) 494 (M+1); $^1$H NMR (CD₃OD): δ 2.25 (s, 3H), 3.15 (t, 2H, J=7.8 Hz), 4.45 (s, 2H), 4.55 (2H, J=7.8 Hz), 4.75 (s, 2H), 6.18 (d, 1H, J=8.2 Hz), 6.74 (d, 1H, J=8.2 Hz), 7.33 (d, 1H, J=8.2 Hz), 7.45 (d, 1H, J=8.2 Hz), 7.50 (d, 1H, J=8.2 Hz), 7.58 (d, 1H, J=8.2 Hz), 7.61 (s, 1H), 7.65 (s, 1H), 8.00 (s, 1H).

Example 86

Preparation of (112)

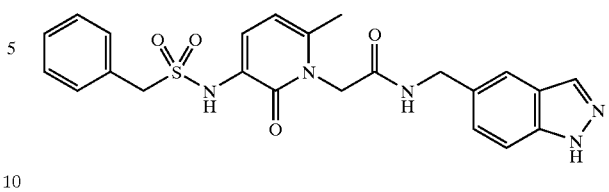

A solution of compound 21 (646 mg, 2.25 mmol), compound 112 (300 mg, 1.5 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase preparatory HPLC eluting with an acetonitrile-0.1% of TFA in water system. Lyophilization under high vacuum (0.1 mm Hg) afforded the product (112) as a white solid (23 mg, 51%). MS (electrospray) 466 (M+1); $^1$H NMR (DMSO-d₆): δ2.25 (s, 3H), 4.40 (d, 2H, J=3.5 Hz), 4.50 (s, 2H), 4.78 (s, 2H), 6.10 (d, 1H, J=8.2 Hz), 7.15 (d, 1H, J=8.2 Hz), 7.32 (m, 6H), 7.48 (d, 1H, J=8.2 Hz), 7.65 (s, 1H), 8.00 (s, 1H), 8.58 (s, 1H), 8.78 (br t, 1H).

Example 87

Preparation of 3-(2-phenethylamino)-6-methyl-1-(3-amino-5-methylenecarboxamidomethylindazolyl)pyrazinone (113)

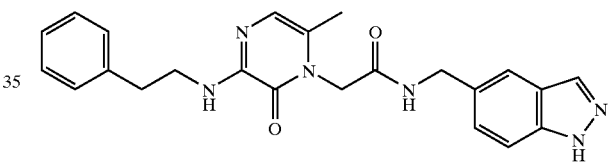

A solution of compound 9 (646 mg, 2.25 mmol), compound 110 (300 mg, 1.5 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase preparatory HPLC eluting with an acetonitrile-0.1% TFA in water system. Lyophilization under high vacuum afforded the product (113) as a white solid (332 mg, 51%). MS (electrospray) 494 (M+1); $^1$H NMR (CD₃OD): δ 2.18 (s, 3H), 2.95 (t, 2H, J=7.2 Hz), 3.64 (t, 2H, J=7.2 Hz), 4.47 (s, 2H), 4.79 (s, 2H), 6.59 (s, 1H), 7.28 (m, 5H), 7.38 (d, 1H, J=7.3 Hz), 7.52 (d, 1H, J=7.3 Hz), 7.79 (s, 1H), 8.85 (br s, 1H).

Example 88

Preparation of (115)

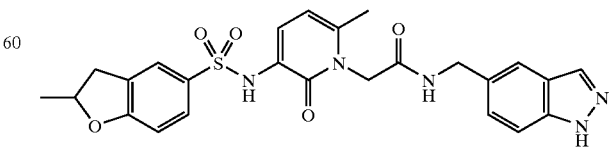

The intermediate 114 was synthesized using the reaction procedures which are described in Examples 9, 10 and 11, substituting 2-methyl-2,3-dihydrobenzofuran (TCI chemicals, Inc.) for 2,3-dihydrobenzofuran (in Example 9).

A solution of compound 114 (300 mg, 0.7 mmol), compound 110 (231 mg, 0.7 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase preparatory HPLC eluting with an acetonitrile-0.1% TFA in water system. Lyophilization under high afforded the product (115) as a white solid (120 mg, 39%). MS (electrospray) 508 (M+1); $^1$H NMR (DMSO-d$_6$): δ 2.20 (s, 3H), 2.32 (s, 3H), 3.25 (t, 2H, J=7.2 Hz), 4.38 (s, 2H), 4.65 (s, 2H), 4.95 (m, 1H), 6.10 (d, 1H, J=7.8 Hz), 6.80 (d, 1H, J=7.8 Hz), 7.22 (m, 2H), 7.50 (m, 1H), 7.62 (m, 2H), 8.05 (s, 1H), 8.70 (m, 1H), 9.00 (s, 1H).

Example 89

Preparation of (117)

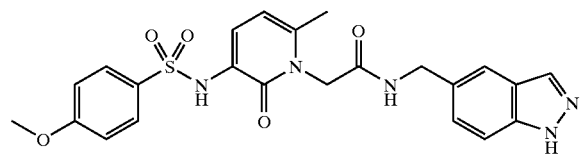

4-Methoxybenzenesulphonyl chloride (Lancaster) was converted to intermediate 116 using the reaction procedures described in Examples 10 and 11.

A solution of compound 116 (180 mg, 0.5 mmol), compound 110 (300 mg, 1.5 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase reparatory HPLC eluting with an acetonitrile-0.1% TFA in water system. Lyophilization under high vacuum afforded the product (117) as a white solid (175 mg, 51%). MS (electrospray) 482 (M+1); $^1$H NMR (DMSO-d$_6$): δ 2.18 (s, 3H), 3.78 (s, 3H), 4.36 (s, 2H), 4.60 (s, 2H), 4.95 (m, 1H), 6.02 (d, 1H, J=7.8 Hz), 6.95 (d, 2H, J=7.8 Hz), 7.20 (t, 2H, J=7.8 Hz), 7.42 (d, 1H, J=7.8 Hz), 7.55 (s, 1H), 7.70 (d, 2H, J=7.8 Hz), 8.00 (s, 1H), 8.65 (m, 1H), 9.05 (s, 1H).

Example 90

Preparation of (119)

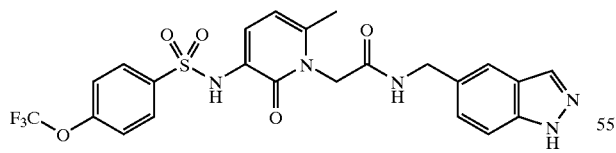

4-(Trifluoromethoxy)benzenesulphonyl chloride (Aldrich) was converted to intermediate 118 using the reaction procedures described in Examples 10 and 11.

A solution of compound 118 (180 mg, 0.5 mmol), compound 110 (300 mg, 1.5 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase prepa- ratory HPLC eluting with an acetonitrile-0.1% TFA in water system. Lyophilization under high vacuum afforded the product (119) as a white solid (2 mg, 1%). MS (electrospray) 536 (M+1);

Example 91

Preparation of (121)

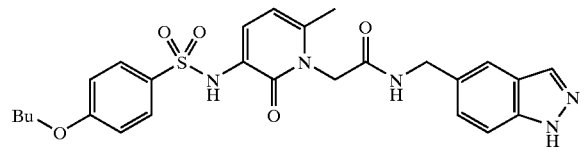

4-(n-Butoxy)benzenesulphonyl chloride (Lancaster) was converted to intermediate 120 using the reaction procedures described in Examples 10 and 11.

A solution of compound 120 (500 mg, 0.13 mmol), compound 110 (290 mg, 1.3 mmol), EDC (Aldrich, 575 mg, 3.0 mmol), HOAt (Aldrich, 408 mg, 3.0 mmol), and NMM (Aldrich, 2.5 mL, 22 mmol) in DMF (10 mL) was stirred at room temperature. After 16 hours, the reaction mixture was treated with 4M HCl in dioxane (Aldrich) at 60° C. for 2 hours, followed by purification using reversed phase preparatory HPLC eluting with an acetonitrile-0.1% TFA in water system. Lyophilization under high vacuum afforded the product (121) as a white solid (101 mg, 3.9%). MS (electrospray) 524 (M+1); $^1$H NMR (DMSO-d$_6$): δ 0.90 (t, 3H J=7.8 Hz), 1.40 (m, 2H), 1.65 (m, 2H), 2.10 (s, 3H), 3.98 (t, 2H, J=7.8 Hz), 4.35 (d, 2H, J=2.5 Hz), 4.62 (s, 2H), 6.05 (d, J=8.2 Hz), 7.00 (m, 2H), 7.21 (m, 2H), 7.50 (m, 1H), 7.60 (s, 1H), 7.75 (d, 2H, J=8.2 Hz), 8.00 (s, 1H), 8.65 (m, 1H), 9.10 (s, 1H).

Figure 16:
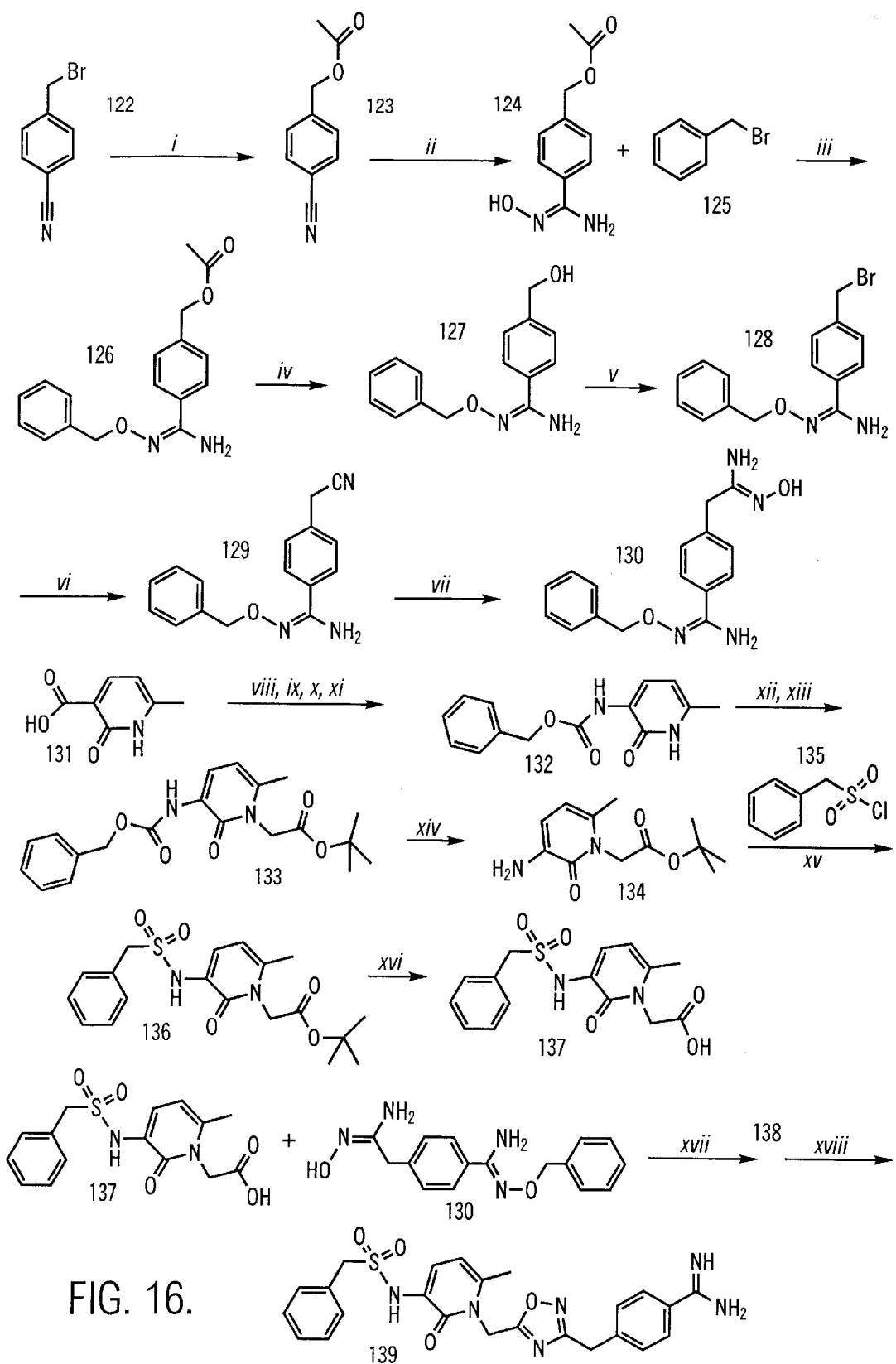
FIG. 16 depicts a reaction scheme for the synthesis of a compound having thrombin inhibitory activity. In this figure, "i" through "xviii" are defined as follows: i) CsOAc, DMF, room temperature 16 hours; ii) hydroxylamine HCl, Et$_3$N, ethanol, room temperature one week; iii) CS$_2$CO$_3$, DMF, room temperature 16 hours; iv) LiOH.H$_2$O, methanol, H$_2$O, room temperature 48 hours; v) DCM, CBr$_4$, Ph$_3$P, room temperature 30 minutes; vi) Et$_4$NCN, CH$_3$CN, room temperature 72 hours; vii) hydroxylamine HCl, Et$_3$N, ethanol, room temperature 72 hours; viii) acetone, Et$_3$N, −5° C., benzyl chloroformate, 0° C. 30 minutes; ix) −5° C., NaN$_3$, H$_2$O, 3° C., 1 hour; x) toluene, 65° C., 16 hours; xi) CH$_3$CN, 1N NaOH, room temperature, 1 hour; xii) 0° C., lithium bis(trimethylsilyl)amide, THF, room temperature, 1.5 hours; xiii) 10° C., t-butyl bromoacetate, room temperature, 16 hours; xiv) 20% Pd(OH)$_2$/C, H$_2$ (40 psi), methanol/H$_2$O, 4 hours; xv) benzylsulfonyl chloride (135), CH$_3$CN, 2,4,6-collidine, room temperature 72 hours; xvi) 50% TFA/DCM, room temperature, 4 hours; xvii) HOAt, EDC, DMF, room temperature 16 hours; and xviii) Zn, HOAc/H$_2$O, 5 minutes. These procedures are more fully described in Examples 92 to 105.
Figure 17:
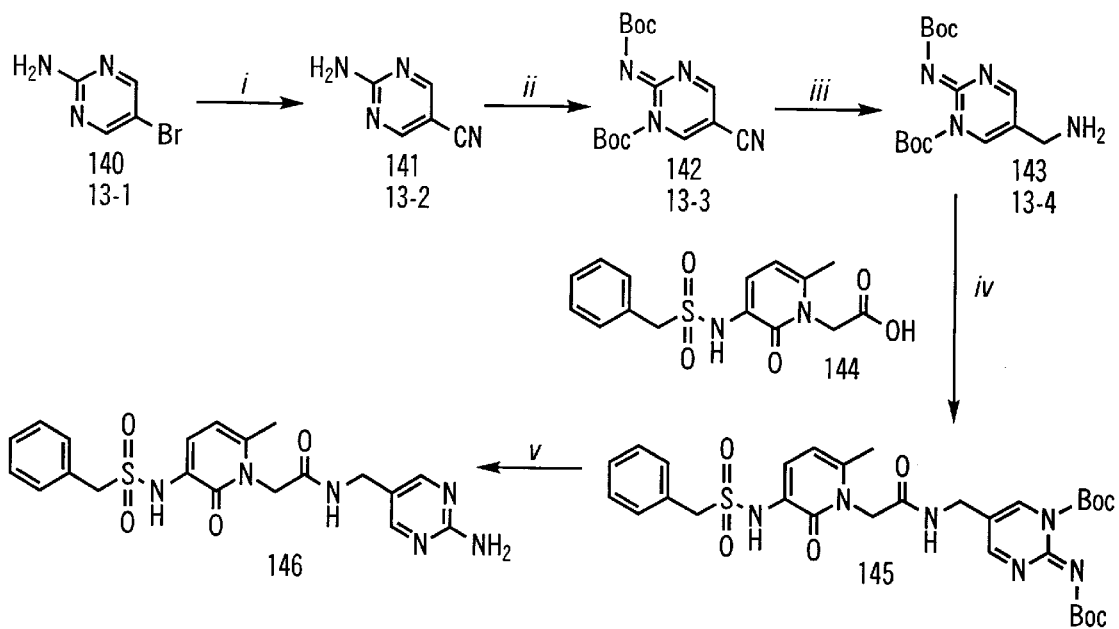
FIG. 17 depicts a reaction scheme for the synthesis of a compound having thrombin inhibitory activity. In this figure, "i" through "v" are defined as follows: i) Cu(I)CN, DMF, reflux, 20 hours; ii) DMAP, Boc$_2$O, THF, room temperature, 2 hours; iii) 10% Pd/C, 1M HCl (aq)/ethanol, H$_2$ (50 psi), 16 hours; iv) EDC, HOBt, NMM, THF, room temperature, 16 hours; and v) TFA/DCM, room temperature 40 minutes. These procedures are more fully described in Examples 106 to 110.
Figure 18:
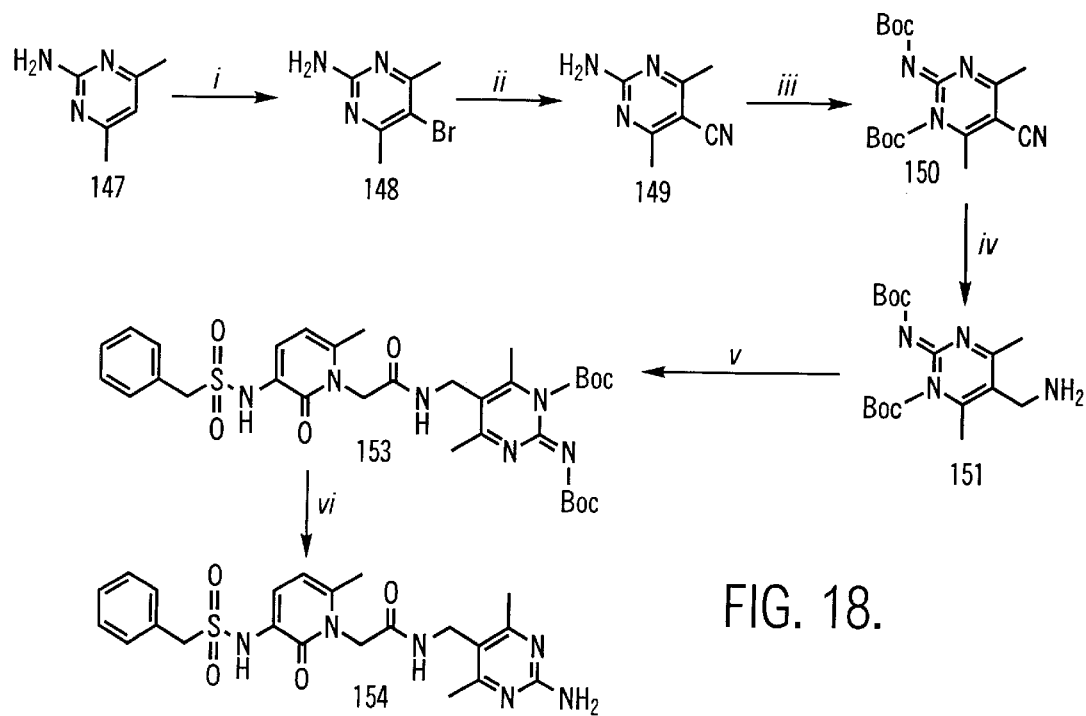
FIG. 18 depicts a reaction scheme for the synthesis of a compound having thrombin inhibitory activity. In this figure, "i" through "vi" are defined as follows: i) H$_2$O/HOAc, Br$_2$, NaHCO$_3$; ii) Cu(I)CN, DMF, reflux 20 hours; iii) Boc$_2$O, DMAP, THF, room temperature 2 hours; iv) 10% Pd/C, 1 N HCl/EtOH, H$_2$(45 psi), 16 hours; v) compound (152), EDC, HOBt, Et$_3$N, room temperature 16 hours; vi) TFA/DCM (1:2), room temperature 25 minutes. These procedures are more fully described in Examples 111 to 116.
Figure 19:
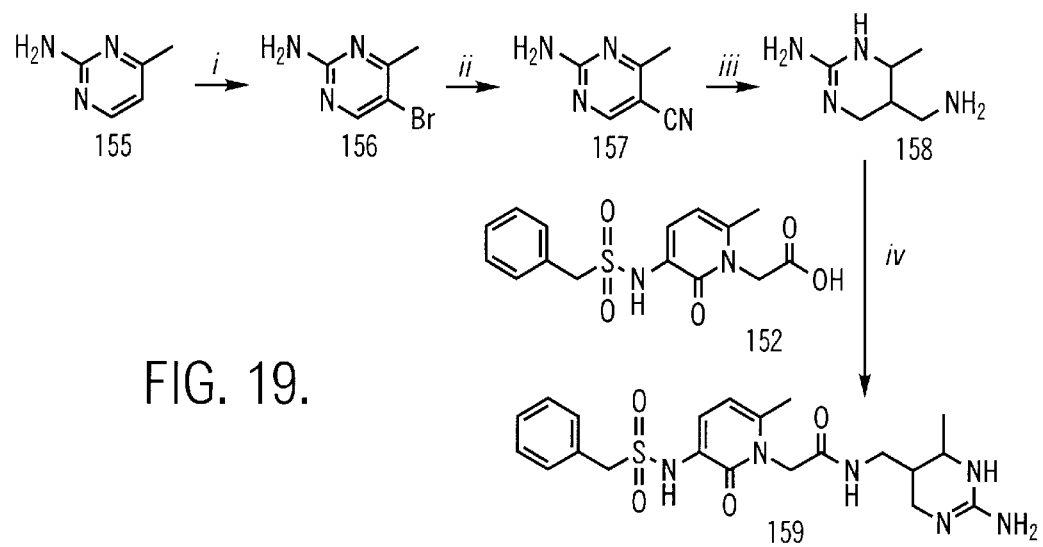
FIG. 19 depicts a reaction scheme for the synthesis of a compound having thrombin inhibitory activity. In this figure, "i" through "iv" are defined as follows: i) Na$_2$CO$_3$, water, Br$_2$, 65° C., 1.5 hours; ii) Cu(I)CN, DMF, 185° C. reflux 20 hours; iii) 10% Pd/C, 1M HCl (aq), EtOH, THF, H$_2$(20 psi), 16 hours; and iv) compound (152), EDC, HOBt, NMM, room temperature 16 hours. These procedures are more fully described in Examples 117 to 120.
Figure 20:
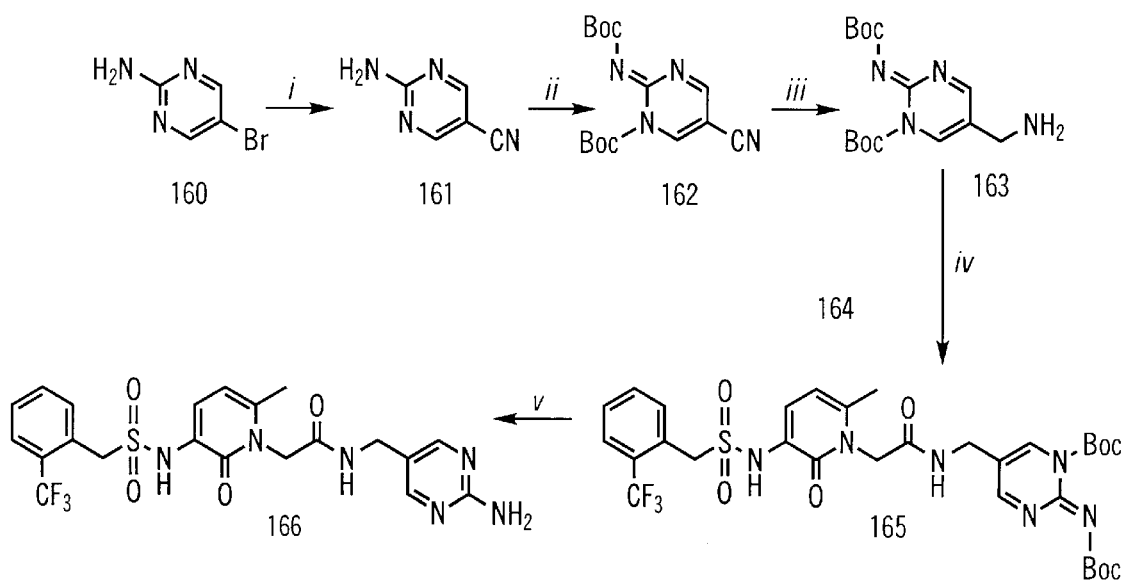
FIG. 20 depicts a reaction scheme for the synthesis of a compound having thrombin inhibitory activity. In this figure, "i" through "v" are defined as follows: i) Cu(I)CN, DMF, reflux 20 hours; ii) Boc$_2$O, DMAP, THF, ambient temperature 2 hours; iii) 10% Pd/C, 1M HCl (aq), EtOH, H$_2$ (50 psi), room temperature 16 hours; iv) compound (164), EDC, HOBt, NMM, THF, room temperature, 16 hours; and v) TFA/DCM (1:1), room temperature 40 minutes. These procedures are more fully described in Examples 121 to 125.
Figure 21:
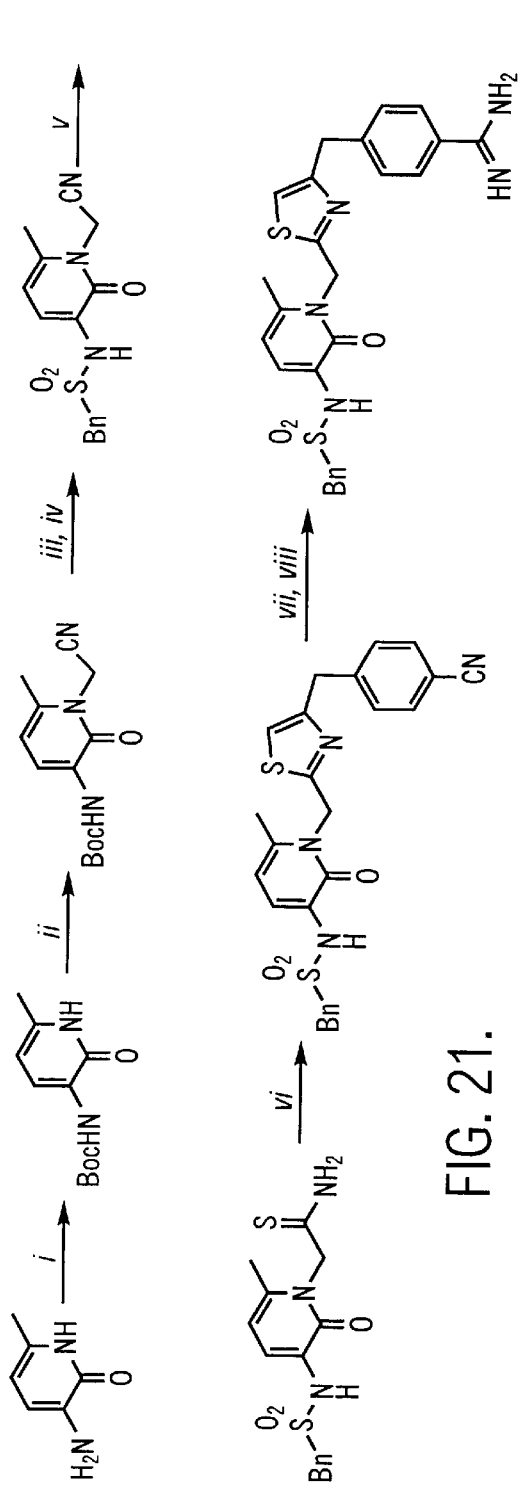
FIG. 21 depicts a reaction scheme for the synthesis of a compound having thrombin inhibitory activity. In this figure, "i" through "viii" are defined as follows: i) BOC$_2$O, K$_2$CO$_3$ in THF; ii) LiN(TMS)$_2$, THF, BrCH$_2$CN, 0° C. to room temperature; iii) HCl, EtOAc, 0° C. to room temperature; iv) BnSO$_2$Cl, N-methylmorpholine, CH$_3$CN, 0° C. to room temperature; v) H$_2$S, pyridine; vi) p-CNPhCH$_2$C(=O)CH$_2$Cl (preparation: P. Richter and G. Wagner, *Pharmazie* 1976, 31, 445–449), benzene, reflux; vii) NH$_2$OH.HCl, Et$_3$N, EtOH, room temperature to reflux; and viii) H$_2$, Pd/C, EtOH, HOAc, H$_2$O.
Figure 22:
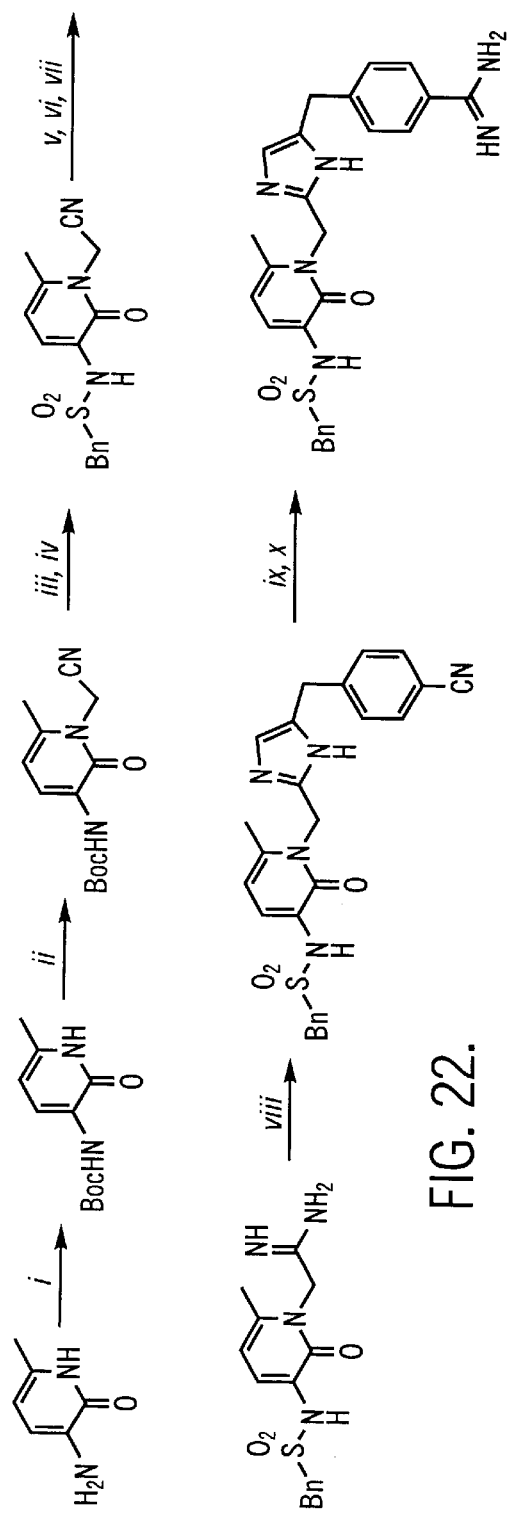
FIG. 22 depicts a reaction scheme for the synthesis of a compound having thrombin inhibitory activity. In this figure, "i" through "x" are defined as follows: i) Boc$_2$O, K$_2$CO$_3$ in THF; ii) LiN(TMS)$_2$, THF, BrCH$_2$CN, 0° C. to room temperature; iii) HCl, EtOAc, 0° C. to room temperature; iv) BnSO$_2$Cl, N-methylmorpholine, CH$_3$CN, 0° C. to room temperature; v) H$_2$S, pyridine; vi) methyl iodide, acetone; vii) NH$_4$OAc, EtOH; viii) p-CNPhCH$_2$C(=O)CH$_2$Cl (preparation: P. Richter and G. Wagner, *Pharmazie*, 1976, 31, 445–449), benzene, reflux; ix) NH$_2$OH.HCl, Et$_3$N, EtOH, room temperature to reflux; and x) H$_2$, Pd/C, EtOH, HOAc, H$_2$O.
Figure 23:
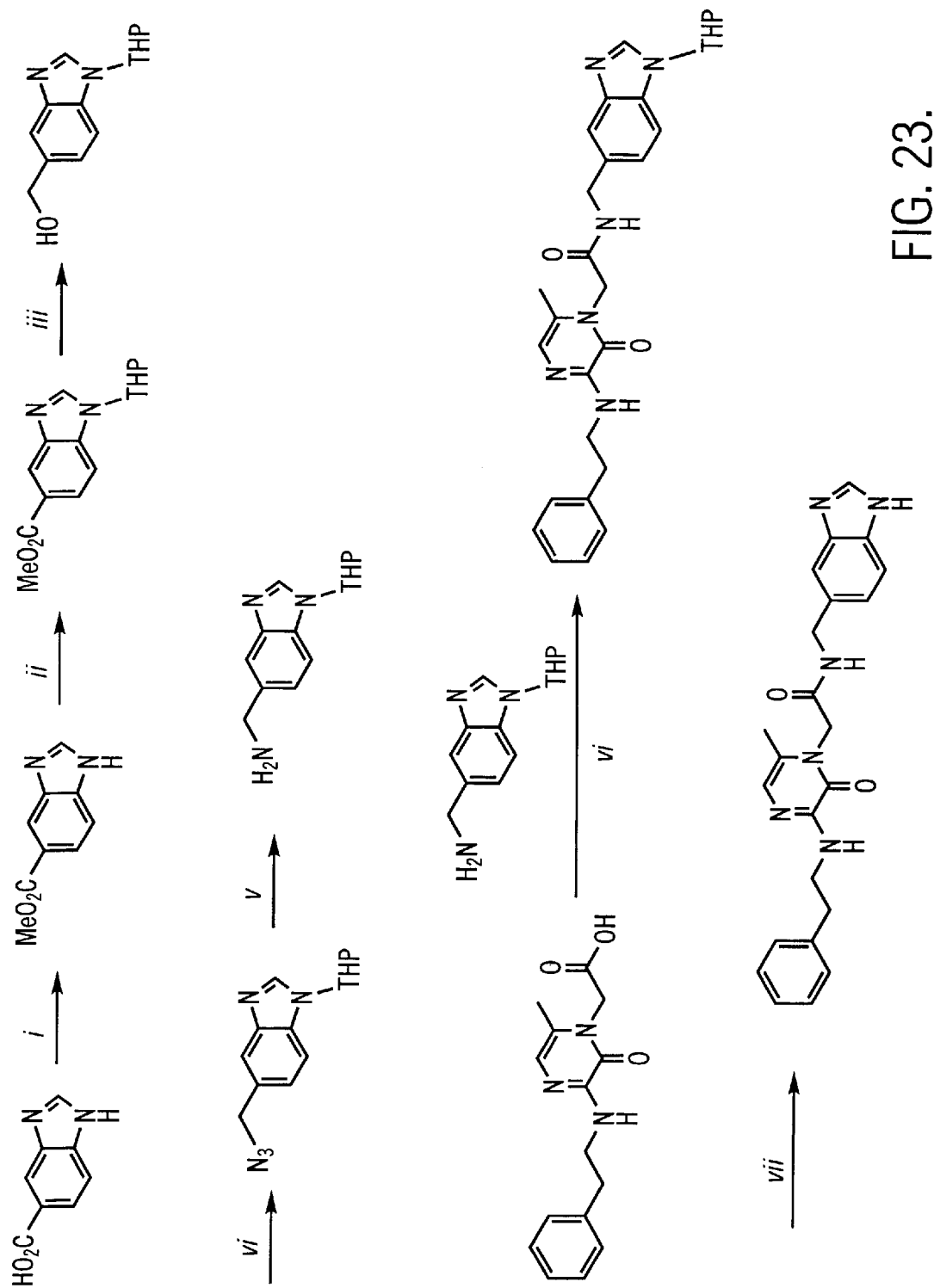
FIG. 23 depicts a reaction scheme for the synthesis of a compound having thrombin inhibitory activity. In this figure, "i" through "vii" are defined as follows: i) H$_2$SO$_4$, methanol, reflux, 20 hours; ii) DHP, PTSA, THF, reflux, 20 hours; iii) LiAH$_4$, THF, room temperature, 30 minutes; iv) DPPA, DBU, THF, room temperature, 18 hours; v) LiAlH$_4$, THF, room temperature, 30 minutes; vi) EDC, HOAt, NMM, DMF, room temperature, 18 hours; and vii) 3N HCl, THF, 50° C., 18 hours.

P. Synthesis of Compound (138, CVS 3401) (FIG. 16)— Examples 92 to 105

Example 92

Preparation of (123)

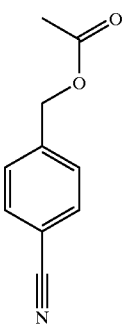

To a solution of p-cyano-benzyl bromide (122) (Aldrich Chemical Company, Inc., 5.08 g, 26 mmol) dissolved in dimethylformamide (52 mL), was added cesium acetate (9.99 g, 52.0 mmoles). After stirring for 16 hours at room temperature, the solution was diluted with diethyl ether (300 mL) and the organic layer was washed with water. The aqueous layer was extracted by diethyl ether again. The organic phases were combined and washed with brine. The organic layer was dried over anhydrous sodium sulfate. The solid was filtered away and the organic solution was concentrated under vacuum to give 4.54 g (99% yield) of the above-identified product (123) as a white crystalline solid. $R_f$=0.2 (3:1 hexane/ethyl acetate).

Example 93

Preparation of (124)

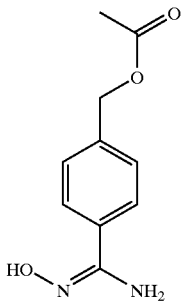

To a solution of the compound of Example 92 (123) (4.00 g, 22.8 mmol) in 100 mL ethanol, was added 1.90 g (27.4 mmol) hydroxy amine hydrochloride followed by 4.8 mL (34.2 mmol) triethylamine. The reaction mixture was stirred under nitrogen for a week at room temperature. Thin layer chromatography (1:1 hexane/ethyl acetate) revealed that the reaction was complete in two days. The reaction mixture was concentrated under vacuum. The resulting residue was dissolved in ethyl acetate and was washed with water, followed by brine. The organic layer was dried over anhydrous sodium sulfate. The solid was filtered away and the organic solution was concentrated under vacuum to give 4.75 g (99% yield) of the above-identified product (124) as a white solid. $R_f$=0.3 ( 1:1 hexane/ethyl acetate).

Example 94

Preparation of (126)

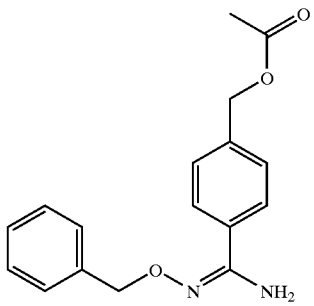

To a solution of the compound of Example 93 (124) (4.75 g, 22.8 mmol) in 50 mL dimethylformamide, was added 12.71 g (39.0 mmol) cesium carbonate and then 4.6 mL (39.0 mmol) benzyl bromide (125). After stirring for 16 hours at room temperature, the reaction mixture was diluted with 200 mL of diethyl ether. The organic layer was washed with water and the aqueous layer was extracted with diethyl ether. The two organic phases were combined, washed with brine, and dried over anhydrous sodium sulfate. The solid was filtered away and the organic solution was concentrated under vacuum. Flash chromatography (silica, 16 to 25% ethyl acetate in hexane) afforded 5.45 g (80% yield) of the above-identified product (126) as a white crystalline solid.

Example 95

Preparation of (127)

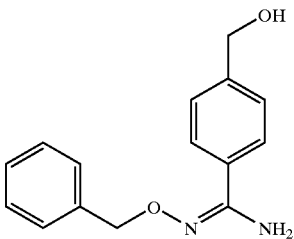

A solution of the compound of Example 94 (126) (6.5 g, 21.79 mmol) in 75 mL of methanol was added to a solution of 3.66 g (87.16 mmol) lithium hydroxide monohydrate in 25 mL water. The resulting mixture was stirred for 48 hours at room temperature. The methanol was evaporated under vacuum. The aqueous solution was neutralized with 1M HCl and extracted twice with 500 mL ethyl acetate. The organic layers were combined and washed with sodium bicarbonate and then brine. The organic layer was dried over anhydrous sodium sulfate. The solid was filtered away and the organic solution was concentrated under vacuum. 4.2 g (75% yield) of the above-identified product (127) was obtained as a white solid. $R_f$=0.4 (1:1 hexane/ethyl acetate).

Example 96

Preparation of (128)

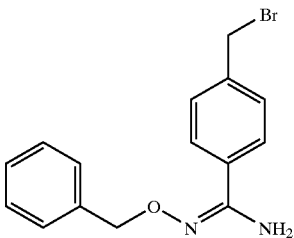

To a solution of the compound of Example 95 (127) (3.90 g, 15.2 mmol) in 115 mL of dichloromethane, was added 7.6 g (22.8 mmol) carbontetrabromide. The reaction mixture was stirred until it became homogeneous. Triphenylphosphine (5.6 g, 21.3 mmol) was added slowly. After the addition was complete, a yellow color appeared, which dissipated after a few minutes. This solution was stirred under nitrogen for 30 minutes at room temperature. The solution was concentrated under vacuum and purified by flash chromatography (silica, 11 to 50% ethyl acetate in hexane) to afford 3.45 g (60% yield) of the above-identified product (128) as a solid. $R_f$=0.5 (1:1 hexane/ethyl acetate).

Example 97

Preparation of (129)

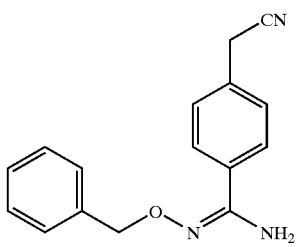

To a solution of the compound of Example 96 (128) (3.45 g, 10.8 mmol) in 40 mL acetonitrile, was added 2.53 g (16.2 mmol) tetraethyl ammonium cyanide. After stirring at room temperature for 72 hours, the reaction mixture was concentrated under vacuum to remove the solvent. The resulting residue was dissolved in ethyl acetate and washed with brine. The brine layer was extracted with ethyl acetate. The organic phases were combined and dried over anhydrous sodium sulfate. The solid was filtered away and the organic solution was concentrated under vacuum. The material was purified by flash chromatography (silica, 20 to 60% ethyl acetate in hexane) to afford 2.5 g (87% yield) of the above-identified product (129) as a solid. $R_f$=0.2 (2:1 hexane/ethyl acetate).

Example 98

Preparation of (130)

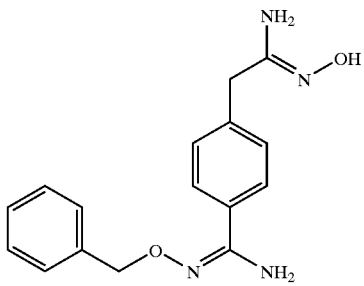

To a solution of the compound of Example 97 (129) (2.50 g, 9.40 mmol) in 40 mL ethanol, was added 0.784 g (11.28 mmol) hydroxy amine hydrochloride, followed by 2.0 mL (14.1 mmol) triethylamine. After stirring at room temperature for 72 hours, the reaction mixture was concentrated under vacuum. The resulting residue was dissolved in ethyl acetate. The organic layer was washed with saturated aqueous ammonium chloride. The ammonium chloride layer was re-extracted with ethyl acetate. The organic phases were combined, washed with brine, and dried over anhydrous sodium sulfate. The sodium sulfate was filtered away and the organic solution was concentrated under vacuum. The material was purified by flash chromatography (silica, 20 to 75% ethyl acetate in hexane) to afford 1.77 g (63% yield) of the above-identified product (130) as a slightly purple solid. $^1$H NMR (CD$_3$OD) δ3.42 (s, 2H), 5.1 (s, 2H), 7.35 (m, 1H), 7.40 (m, 4H), 7.48 (d, J=7 Hz, 2H), 7.6 (d, J=8 Hz, 2H).

Example 99

Preparation of (132)

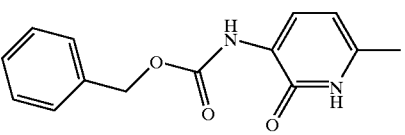

To a solution of 75.0 g (163.2 mmol) 2-hydroxy, 6-methyl nicotinic acid (131) in 200 mL acetone, was added 50 mL (359.0 mmol) triethylamine under a nitrogen atmosphere. The reaction mixture was cooled to −5° C. and 55.7 g (326.4 mmol) benzyl chloroformate in 50 mL of acetone was added over 30 minutes. The reaction mixture was stirred for 30 minutes at 0° C. and then cooled to −5° C. A solution of 21.2 g (326.4 mmol) sodium azide in 75 mL water was added to the reaction mixture over 10 minutes. The resulting mixture was stirred for 1 hour at 3° C. The reaction mixture was then poured into 700 mL ice water and let to warm to room temperature. The aqueous solution was extracted 3 times with 250 mL toluene. The organic phases were combined and dried over anhydrous sodium sulfate. The sodium sulfate was filtered away and the organic layer was concentrated to remove the acetone. The resulting solution of toluene was heated to 65° C. for 16 hours. The reaction mixture was cooled to room temperature and was then concentrated under vacuum. The remaining residue was dissolved in 100 mL acetonitrile. Once a homogeneous solution formed, 100 mL (100 mmol) of 1N NaOH was added. The resulting solution was stirred for 1 hour at room temperature. To the reaction mixture was added 100 mL isopropanol, at which time the product precipitated out of solution. The solid product was isolated via filtration. Further purification was completed by recrystallization from isopropyl alcohol or by flash chromatography (silica, 0 to 4% methanol in dichloromethane). After complete purification, the above-identified product (132) was isolated as an off-white solid, 16.0 g (38%). $R_f$=0.2 (10% ethyl acetate in dichloromethane).

Example 100

Preparation of (133)

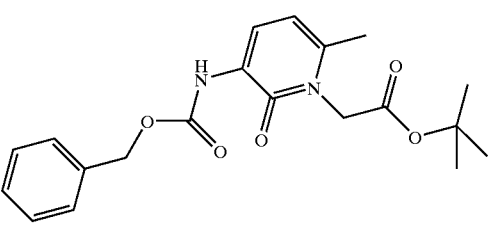

To a solution of the compound of Example 99 (132) (10.0 g, 38.7 mmol) in 50 mL anhydrous tetrahydrofuran cooled to 0° C. under a nitrogen atmosphere, was added a 1M solution of lithium bis(trimethylsilyl)amide in tetrahydrofuran (39.1 mL 39.1 mmol) over 40 minutes. The ice bath was removed and the reaction mixture was stirred for 1.5 hours at room temperature. The reaction mixture was then cooled to 10° C. and 5.72 mL (38.7 mmol) t-butyl bromoacetate was added in two portions. The reaction mixture was stirred for 16 hours at room temperature. The reaction was quenched with 1.0 mL of water. The solution was concentrated under vacuum. The residue was dissolved in 200 mL ethyl acetate and washed sequentially with 50 mL 1N hydrochloric acid, saturated aqueous sodium bicarbonate, water, and brine. The organic layer was dried over anhydrous sodium sulfate. The sodium sulfate was filtered away and the organic solution was concentrated under vacuum. The resulting oil was triturated twice with 200 mL of hexane and once with 200 mL of 1:1 hexane/diethyl ether. The solvent was removed under vacuum to afford 11.7 g (81% yield) of the above-identified product (133). $^1$H NMR (CDCl$_3$) δ 1.48 (s, 9H), 2.24 (s, 3H), 4.75 (s, 2H), 5.20 (s, 2H), 6.10 (d, 1 H), 7.35 (m, 5H) , 7.35 (d, 1H).

Example 101

Preparation of (134)

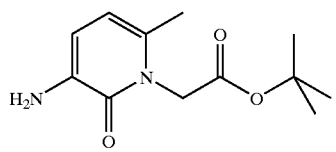

To a solution of the compound of Example 100 (133) (25.0 g, 67.1 mmol) in 280 mL methanol/water (4:1, V/V) under a nitrogen atmosphere, was added 2.5 g 20% palladium(II) hydroxide on carbon. The reaction mixture was hydrogenated at 40 psi for 4 hours. Thin layer chromatography (5% methanol in dichloromethane) revealed no more starting material was present. The catalyst was filtered off and washed with methanol. The organic solution was concentrated under vacuum to afford 15.77 g (98%) of the above-identified product (134) as a light yellow solid. R$_f$=0.4 (5% methanol in dichloromethane).

Example 102

Preparation of (136)

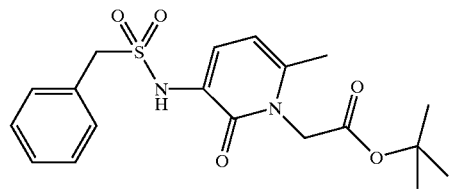

To a solution of the compound of Example 101 (134) (25.0 g, 67.1 mmol) in 200 mL of acetonitrile, was added 20.69 g (131.08 mmol) of benzyl sulfonyl chloride (135). Once the solution became homogeneous, 13.1 mL (99.4 mmol) of 2,4,6-collidine was added. The reaction mixture stirred 72 hours at room temperature. Thin layer chromatography using a solution of 5% methanol in dichloromethane revealed no starting material was present. The solvent was removed under vacuum. The resulting residue was dissolved in 400 mL dichloromethane and washed subsequently with 0.5 M hydrochloric acid and brine. The organic layer was dried over anhydrous magnesium sulfate. The magnesium sulfate was filtered away and the solution was concentrated under vacuum. The crude product was purified by flash chromatography (silica, 3 to 5% methanol in dichloromethane). The above-identified product (136) was isolated as a light brown solid, 13.6 g (77%). R$_f$=0.66 (5% methanol in dichloromethane).

Example 103

Preparation of (137)

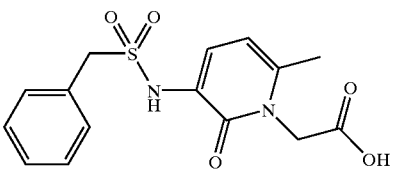

The compound of Example 102 (136) (13.6 g, 34.65 mmol) was dissolved in 50 mL 50% trifluoroacetic acid in dichloromethane and stirred at room temperature for 4 hours. The solvent was evaporated under vacuum. A solution of dichloromethane and toluene was added as an azeotrope. The solution was concentrated under vacuum to afford 13.6 g of the above-identified product (137) as a light brown solid.

Example 104

Preparation of (138)

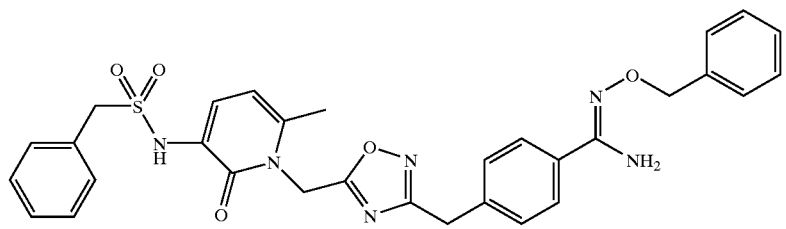

The compound of Example 103 (137) (0.336 g, 1 mmol) was dissolved in 5 mL anhydrous dimethylformamide under a nitrogen atmosphere at room temperature. To the reaction mixture was added 0.149 g (1.1 mmol) 1-hydroxy-7-azabenzotriazole and 0.210 g (1.1 mmol) 1-ethyl-3-(3'-dimethylaminopropyl)carbodiimide hydrochloride. The solution was stirred until homogeneous and then compound of Example 98 (130) (0.284 g, 1 mmol) was added. The reaction mixture was stirred for 16 hours at room temperature. A portion of the crude reaction mixture was subjected to analytical HPLC using a 4.6×250 mm reverse phase column containing a C-18 resin comprised of 5 micron-size gel particles (elution=1 mL/min, 15 to 60% acetonitrile in water with 0.1% trifluoroacetic acid over 20 minutes). The intermediate, uncyclized product had a retention time of 15.4 minutes. The reaction mixture was heated to 95° C. for 2 hours. The reaction mixture was then cooled to room temperature and was diluted with 200 mL of ethyl acetate. The organic solution was washed with 100 mL of water, saturated aqueous sodium bicarbonate, brine, and dried over anhydrous sodium sulfate. The sodium sulfate was filtered away and the organic solution was concentrated under vacuum. Using the above HPLC conditions, the retention time for cyclized product was 17.1 minutes. The material was purified by flash chromatography (silica, 16 to 33% ethyl acetate in hexane) to afford 0.140 g (24% yield) of the above-identified product (138) as a white solid.

Example 105

Preparation of (139)

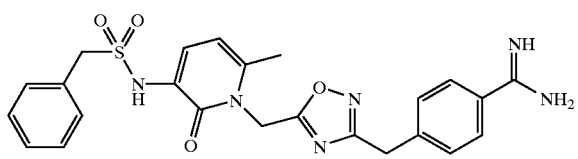

A solution of activated zinc dust was prepared by adding 0.612 g (9.36 mmol) zinc dust to 3 mL 0.5N hydrochloric acid and stirring for 5 minutes. The solution was decanted and washed with water and methanol. A portion of the activated zinc (300 mg, 4.6 mmol) was added to a solution of the compound Example 104 (138) (0.140 g, 0.234 mmol) in 5 mL 80% acetic acid in water. The reaction was quenched after 5 minutes by adding 15 mL water. The reaction mixture was filtered and washed with an additional 10 mL of water. The aqueous solution was applied directly to a preparative HPLC (a 22×250 mm reverse phase column containing a C-18 resin comprised of 10 micron-size gel particles, elution=25 mL/min, 0 to 25% acetonitrile in water with 0.1% trifluoroacetic acid over 60 minutes). The desired fractions were collected, the acetonitrile was removed under vacuum, and the aqueous solution was frozen and lyophilized to afford 1.5 mg of the above-identified product (139) as a white solid. Analytical HPLC retention time=12.1 minutes, (15 to 60% acetonitrile in water with 0.1% trifluoroacetic acid over 20 minutes).

Q. Synthesis of Compound (146) (FIG. 17) Examples 106 to 110

Example 106

Preparation of (141)

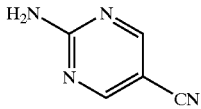

A solution of 2-amino-5-bromopyrimidine (140) (Aldrich, 50.0 g, 0.287 mol) and copper(I) cyanide (Aldrich, 33.0 g, 0.373 mol) in DMF (155 mL) was heated to reflux at 185° C. After 20 hours the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, filtered, and evaporated in vacuo to afford the product (141) (22.8 g, 66%) as a brown solid. $R_f$=0.22 (1:1 of ethyl acetate/hexane). MS: m/e 121 (M+H)$^+$.

Example 107

Preparation of (142)

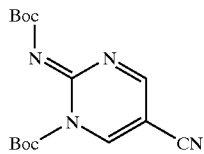

A solution of the product of Example 106 (141) (10.0 g, 0.083 mol), Boc$_2$O (54.45 g, 0.250 mol) and DMAP (10.16 g, 0.083 mol) in THF (80 mL) was stirred at ambient temperature for 2 hours. The solvent was removed under vacuum. The residue was partitioned between ethyl acetate and aqueous 0.25 M HCl solution. The organic layer was washed with 10% aqueous Na$_2$CO$_3$ solution, and brine then dried over magnesium sulfate. Removal of organic solvent afforded the product (142) (15.9 g, 60%) as a brown solid. $R_f$=0.7 (1:1 of ethyl acetate/hexane). MS: m/e 321(M+H)$^+$.

Example 108

Preparation of (143)

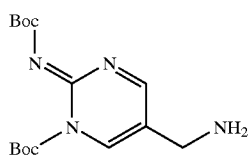

A suspension of the compound of Example 107 (142) (7.0 g, 21.8 mmol), 10% Pd/C (Aldrich, 2.8 g), and 1M aqueous HCl (21.9 mL) in ethanol (80 mL) was shaked in a Parr apparatus under H$_2$ (50 psi) for 16 hours. The solid was removed and the solution was concentrated under vacuum to give the product (143) (4.9 g, 69%). $R_f$=0.46 (1:1 of ethyl acetate/hexane). MS: m/e 325(M+H)$^+$.

Example 109

Preparation of (145)

A solution of the compound of Example 108 (143) (250 mg, 0.77 mmol), compound (144) (259 mg, 0.77 mmol), EDC (192 mg, 1.0 mmol), ), HOBt (136 mg, 1.0 mmol), and NMM (170 uL 1.5 mmol) in THF (8 mL) was stirred at room temperature for 16 hours. After removal of solvent the residue was partitioned in EtOAc and water. The organic layer was washed with water (2 times), aqueous Na$_2$CO$_3$ solution and water. After drying over magnesium sulfate, the solvent was removed to obtain the product (145) (322 mg, 65%). MS: m/e 463(M+H)$^+$.

Example 110
Preparation of (146)

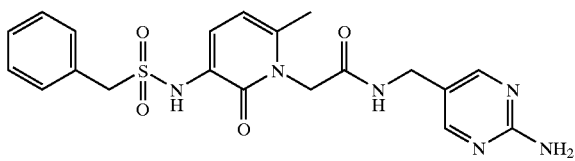

The compound of Example 109 (145) (300 mg, 0.47 mmol) was added with a solution of TFA and methylene chloride (1:1, 20 mL). The resulting mixture was stirred at room temperature for 40 minutes. After removal of solvent, the residue was subjected to preparative HPLC purification eluting with an acetonitrile-0.1% TFA in water system. The pure fractions were concentrated and lyophilized to provided a white solid product (146) (93 mg, 45%). MS: m/e 443 (M+H)$^+$. $^1$H NMR (400 MHz, CD$_3$OD): δ 2.27 (s, 3H), 4.28 (s, 2H), 4.43 (s, 2H), 4.80 (s, 2H), 6.20 (d, 1H, J=7.8 Hz), 7.25 (m, 6H), 8.42 (s, 2H).

R. Synthesis of Compound (154) (FIG. 18)—Examples 111 to 116

Example 111
Preparation of (148)

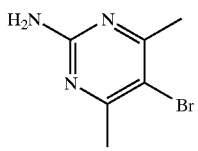

To a solution of 2-amino-4,6-dimethylpyrimidine (147, Aldrich, 20.0 g, 162.39 mmol) in HoAc (200 mL) was added bromine (Spectrum, 28.55 g, 178.62 mmol) drop-wise at 0° C. After half of the portion of bromine was added, the reaction mixture changed color from clear to dark orange. The reaction was monitored by TLC using (1 ethylacetate/1 hexane). Saturated aqueous NaHCO$_3$ was added to neutralize HOAc. The reaction mixture was extracted with ethylacetate (2×). The organic layer was washed with saturated aqueous NaHCO$_3$ and evaporated in vacuo to give compound (148) (21.32 g, 65%). R$_f$=0.29 (1:1 of ethyl acetate/hexane). MS: m/e 203 (M+H)$^+$.

Example 112
Preparation of (149)

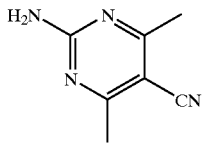

A solution of 2-amino-4,6-dimethyl-5-bromopyrimidine (148, 20.0 g, 98.93 mmol) and copper(I) cyanide (Aldrich, 11.52 g, 128.61 mmol) in DMF (200 mL) was heated to reflux at 185° C. After 20 hours, the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, and evaporated in vacuo to afford compound (149) as a yellow solid (9.0 g, 61%). R$_f$=0.17 (1:1 of ethyl acetate/hexane). MS: m/e 149 (M+H)$^+$.

Example 113
Preparation of (150)

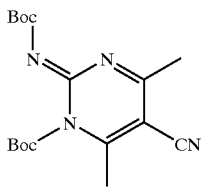

A solution of (149) (8.6 g, 58.10 mmol), Boc$_2$O (25.33 g, 116.22 mmol) and DMAP (7.1 g, 58.10 mmol) in THF (150 mL) was stirred at ambient temperature for 2 hours. The solvent was removed under vacuum. The residue was partitioned between ethyl acetate and aqueous 0.25M HCl solution. The organic layer was washed with 10% aqueous Na$_2$CO$_3$ solution and brine, then dried over magnesium sulfate. Removal of organic solvent afforded compound (150) (15.6 g, 77%) as a dark brown solid. R$_f$=0.33 (1:2 of ethyl acetate/hexane). MS: m/e 349(M+H)$^+$.

Example 114
Preparation of (151)

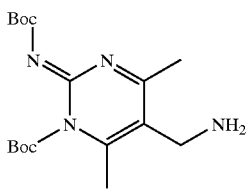

A suspension of compound (150) (6.5 g, 18.68 mmol), 10% Pd/C (Aldrich, 1.3 g), and 1M aqueous HCl (375 μL) in ethanol (30 mL) was shaked in a Parr apparatus under H$_2$ (45 psi) for 16 hours. The solid was removed and the solution was concentrated under vacuum to give compound (151) (6.11 g, 93%). MS: m/e 353(M+H)$^+$.

Example 115
Preparation of (153)

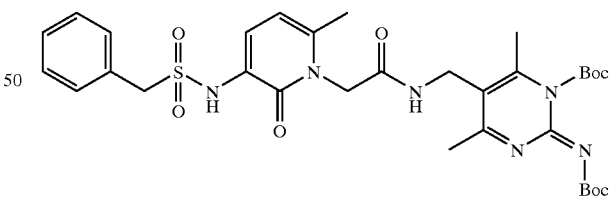

A solution of compound (151) (150 mg, 0.43 mmol), 3-benzylsulfonylamino-6-methyl-1-methylenecarboxy-2-pyridinone (compound 152)(143 mg, 0.43 mmol), EDC (106 mg, 0.55 mmol), HOBt (75 mg, 0.55 mmol), and Et$_3$N (136 μL 0.98 mmol) in DMF (5 mL) was stirred at room temperature for 16 hours. After removal of solvent, the residue was partitioned in EtOAc and water. The organic layer was washed with water (2 times), NaHCO$_3$ and water. After drying over magnesium sulfate, the solvent was removed to obtain compound (153)(285 mg, 100%). R$_f$=0.19 (9:1 of dichloromethylene/isopropylalcohol). MS: m/e 671(M+H)$^+$.

Example 116

Preparation of (154)

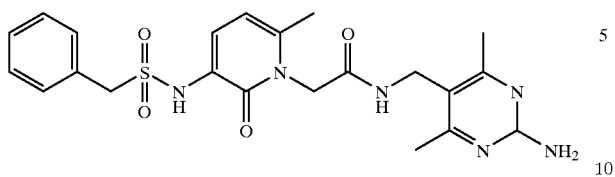

Compound (153) (250 mg, 0.37 mmol) was added to a solution of TFA and methylene chloride (1:2, 10 mL). The resulting mixture was stirred at room temperature for 25 minutes. After removal of solvent, the residue was subjected to preparative HPLC purification, eluting with an acetonitrile-0.1% TFA in water system. The pure fractions were concentrated and lyophilized to provide a white solid product compound (154) (84 mg, 48%). MS: m/e 471(M+H)$^+$. $^1$H NMR (400 MHz, CD$_3$OD): δ 2.27 (s, 3H), 2.55 (s, 6H), 3.8 (s, 2H), 4.4 (s, 2H), 4.7 (s, 2H), 6.18 (d, 1H), 7.2 (b, 6H).

S. Synthesis of Compound (159) (FIG. 19)—Examples 117 to 120

Example 117

Preparation of (156)

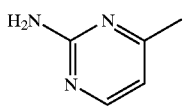

A solution of 2-amino-4-methylpyrimidine (155, Aldrich, 10.0 g, 91.63 mmol) and sodium carbonate (Aldrich, 4.8 g, 45.81 mmol) in water (100 mL) was heated to 65° C. Then, bromine (Aldrich, 16.1 g, 100.79 mmol) was added dropwise to the reaction mixture. After 1.5 hours the reaction mixture was allowed to cool to room temperature; then, saturated aqueous NaHCO$_3$ was added. The precipitate was filtered and recrystallized from ethyl alcohol. The residue was dried under vacuum to give compound (156) (11.0 g, 65%) as a yellow solid. MS: m/e 188 (N4+H)$^+$.

Example 118

Preparation of (157)

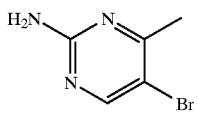

A solution of 2-amino-4-methyl-5-bromopyrimidine (156, 10.0 g, 53.19 mmol) and copper(I) cyanide (Aldrich, 6.19 g, 69.14 mmol) in DMF (80 mL) was heated to reflux at 185° C. After 20 hours, the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, and evaporated in vacuo to afford yellow solid (4.27 g, 60%). R$_f$=0.19 (1:1 of ethyl acetate/hexane). MS: m/e 135 (M+H)$^+$.

Example 119

Preparation of (158)

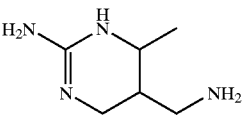

A suspension of compound (157) (1.0 g, 7.46 mmol), 10% Pd/C (Aldrich, 250 mg), and 1M aqueous HCl (14.8 mL) in ethanol (11 mL) and THF (15 mL) was shaken in a Parr apparatus under H$_2$ (20 psi) for 16 hours. The solid was removed and the solution was concentrated under vacuum to give compound (158) (1.0 g, 94%). MS: m/e 216 (M+H+MeOH+Na+H$_2$O)$^+$.

Example 120

Preparation of (159)

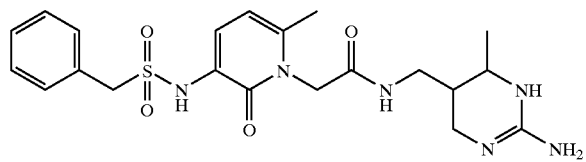

A solution of compound (158) (95 mg, 0.45 mmol), 3-benzylsulfonylamino-6-methyl-1-methylenecarboxy-2-pyridinone (compound (152)) (150 mg, 0.45 mmol), EDC (102 mg, 0.54 mmol), HOBt (73 mg, 0.54 mmol), and NMM (98 uL 0.89 mmol) in THF (6 mL) was stirred at room temperature for 16 hours. After removal of solvent the residue was partitioned in EtOAc and water. The aqueous layer was washed with EtOAc (2 times). The residue was subjected to preparative HPLC purification, eluting with an acetonitrile-0.1% TFA in water system. The pure fractions were concentrated and lyophilized to provide the product compound (159) as a white solid (13 mg, 6.3%). MS: m/e 461 (M+H)$^+$. $^1$H NMR (400 MHz, D$_2$O): δ 1.1 (d, 3H), 2.2 (s, 3H), 3–3.60 (m, 6H), 4.40 (s, 2H), 4.70 (s, 2H), 6.18 (d, 1H), 7.2 (b, 6H).

T. Synthesis of Compound (166) (FIG. 20)—Examples 121 to 125

Example 121

Preparation of (161)

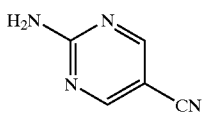

A solution of 2-amino-5-bromopyrimidine (160, Aldrich, 50.0 g, 0.287 mol) and copper(I) cyanide (Aldrich, 33.0 g, 0.373 mol) in DMF (155 mL) was heated to reflux at 185° C. After 20 hours the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, filtered, and evaporated in vacuo to afford compound (161) (22.8 g, 66%) as a brown solid. R$_f$=0.22 (1:1 of ethyl acetate/hexane). MS: m/e 121 (M+H)$^+$.

Example 122
Preparation of (162)

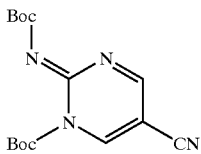

A solution compound (161) (10.0 g, 0.083 mol), $Boc_2O$ (54.45 g, 0.250 mol) and DMAP (10.16 g, 0.083 mol) in THF (80 mL) was stirred at ambient temperature for 2 hours. The solvent was removed under vacuum. The residue was partitioned between ethyl acetate and aqueous 0.25M HCl solution. The organic layer was washed with 10% aqueous $Na_2CO_3$ solution, and brine; then, dried over magnesium sulfate. Removal of organic solvent afforded compound (162) (15.9 g, 60%) as a brown solid. $R_f$=0.7 (1:1 of ethyl acetate/hexane). MS: m/e 321 $(M+H)^+$.

Example 123
Preparation of (163)

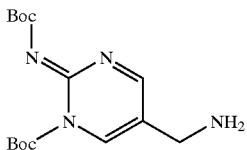

A suspension of compound (162) (7.0 g, 21.8 mmol), 10% Pd/C (Aldrich, 2.8 g), and 1M aqueous HCl (21.9 mL) in ethanol (80 mL) was shaken in a Parr apparatus under $H_2$ (50 psi) for 16 hours. The solid was removed and the solution was concentrated under vacuum to give compound (163) (4.9 g, 69%). $R_f$ 0.46 (1:1 of ethyl acetate/hexane). MS: m/e 325 $(M+H)^+$.

Example 124
Preparation of (165)

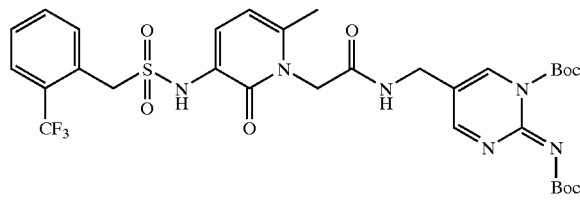

The intermediate, 3-(2-trifluoromethyl)benzyl-sulfonylamino-6-methyl-1-methylenecarboxy-2-pyridinone (164) may be prepared according to the procedures described in Examples 7 and 89 of commonly-assigned U.S. Pat. No. 5,658,930.

A solution of compound (163) (150 mg, 0.46 mmol), 3(2-trifluoromethyl)benzyl-sulfonylamino-6-methyl-1-methylenecarboxy-2-pyridinone (compound (164)) (187 mg, 0.46 mmol), EDC (115 mg, 0.6 mmol), HOBt (82 mg, 0.6 mmol), and NMM (94 uL 0.93 mmol) in THF (5 mL) was stirred at room temperature for 16 hours. After removal of solvent, the residue was partitioned in EtOAc and water. The organic layer was washed with water (2 times), $Na_2CO_3$, and water. After drying over magnesium sulfate, the solvent was removed to obtain compound (165) (205 mg, 63%). MS: m/e 711.0 $(M+H)^+$.

Example 125
Preparation of (166)

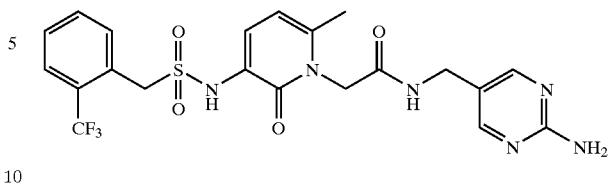

The compound (165) (200 mg, 0.28 mmol) was added to a solution of TFA and methylene chloride (1:1, 20 mL). The resulting mixture was stirred at room temperature for 40 minutes. After removal of solvent, the residue was subjected to preparative HPLC purification eluting with an acetonitrile 0.1% TFA in water system. The pure fractions were concentrated and lyophilized to provide the product compound (166) as a white solid product (38 mg, 27%). MS: m/e 511 $(M+H)^+$. $^1H$ NMR (400 MHz, $CD_3OD$): δ 2.27 (s, 3H), 4.28 (s, 2H), 4.43 (s, 2H), 4.80 (s, 2H), 6.20 (d, 1H, J=7.8 Hz), 7.38 (d, 1H), 7.45–7.70 (m, 4H), 8.40 (s, 2H).

Example A
In Vitro Enzyme Assays for Specificity Determination

The ability of compounds of the present invention to act as a selective inhibitor of thrombin activity was assessed by determining the concentration of test-compound which inhibited the activity of this enzyme by 50%, ($IC_{50}$), and comparing this value to that determined for all or some of the following related serine proteases: recombinant tissue plasminogen activator (rt-PA), plasmin, activated protein C, chymotrypsin, factor Xa and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the IC50 value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroanilin e, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nit roaniline), obtained from DiaPharma Group (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroanilin e, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzloxy-D-lysine-L-prolyl-L-arginine-p-nitroa niline dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroani lide), which was obtained from DiaPharma Group. The substrate was made up in deionized water followed by dilution in HBSA prior to the assay in which the final concentration was 100 micromolar (about 9-times Km). Purified (3×-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3×-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table I lists the determined $IC_{50}$ values for certain of the enzymes listed above for compounds of the present invention and demonstrate the high degree of specificity for the inhibition of alpha-thrombin compared to these related serine proteases.

TABLE I

| Compound (FIG. 24) | fIIa IC 50 (0 min) | Ki | fXa IC50 | Trypsin IC50 |
|---|---|---|---|---|
| A | C | B | D | D |
| B | C | B | I | I |
| C | C | B | I | I |
| D | C | A | I | I |
| E | C | A | I | I |
| F | A | A | I | I |
| G | A | A | I | I |
| H | A | A | I | I |
| I | A | A | I | I |

A = ≦100 nM
B = >100, ≦399 nM
C = >300, <2500 nM
D = ≧2500 nM
I = Inactive

We claim:

1. A compound of the formula:

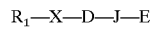

wherein
(a) X is selected from the group consisting of —S(O)$_2$—NH—, —N(R')—S(O)$_2$—NH—, —C(=O)—NH—, —OC(=O)—NH—, and —N(R')C(=O)—NH—, wherein R' is selected from hydrogen, alkyl of 1 to about 4 carbon atoms, aryl of about 6 to about 14 carbon atoms and aralkyl of about 6 to about 16 carbon atoms;

(b) R$_1$ is selected from the group consisting of:
(1) alkyl of 1 to about 12 carbon atoms which is optionally substituted with Y$_1$ and/or Y$_2$,
(2) alkyl of 1 to about 3 carbon atoms substituted with cycloalkyl of about 3 to about 8 carbon atoms which is optionally mono-, di-, or tri-substituted on the ring with Y$_1$, Y$_2$ and/or Y$_3$,
(3) cycloalkyl of 3 to about 15 carbon atoms, which is optionally mono-, di-, or tri-substituted on the ring with Y$_1$, Y$_2$ and/or Y$_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$ and/or Y$_3$, (5) heterocyclo of 4 to about 10 ring atoms with the ring atoms selected from carbon and heteroatoms, wherein the heteroatoms are selected from the group consisting of oxygen, nitrogen, and S(O)$_i$, including

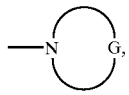

wherein

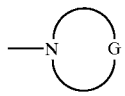

is a 5 to 7 member heterocycle of 3 to 6 ring carbon atoms, where G is —CH$_2$—, —O—, —S(=O)—, —S(O)$_2$— or —S—, which is optionally mono-, di-, or tri-substituted on the ring carbons with Y$_1$, Y$_2$ and/or Y$_3$, (6) alkenyl of about 2 to about 6 carbon atoms which is optionally substituted with cycloalkyl of about 5 to about 8 carbon atoms, which is optionally mono-, di-, or tri-substituted on the ring carbons with Y$_1$, Y2 and/or Y$_3$, (7) aryl of about 6 to about 14 carbon atoms which is optionally mono-, di- or tri-substituted with Y$_1$, Y$_2$, and/or Y$_3$, (8) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with Y$_1$, Y$_2$, and/or Y$_3$, (9) aralkyl of about 7 to about 15 carbon atoms which is optionally substituted on the alkyl chain with hydroxy or halogen and mono-, di-, or tri-substituted in the aryl ring with Y$_1$, Y$_2$, and/or Y$_3$,

(10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy on halogen and optionally mono-, di-, or tri-substituted on the ring with Y$_1$, Y$_2$, and/or Y$_3$,

(11) aralkenyl of about 8 to about 16 carbon atoms which is optionally mono-, di-, on tri-substituted on the aryl ring with Y$_1$, Y$_2$, and/or Y$_3$,

(12) heteroaralkenyl of 5 to 14 ring atoms with the ring atoms selected from carbon and heteroatoms, wherein the heteroatoms are selected from oxygen, nitrogen, and sulfur, and which is optionally mono-, di-, or tri-substituted on the ring with Y$_1$, Y$_2$, and/or Y$_3$, (13)

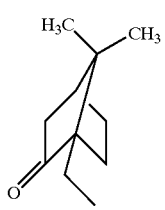

(14)

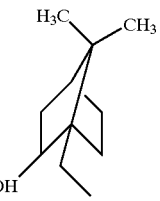

(15)

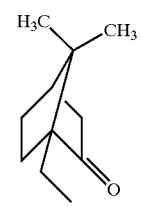

(16)

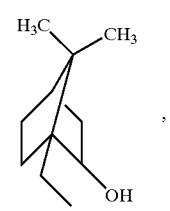

(17) fused carbocyclic alkyl of about 5 to about 15 carbon atoms,

(18) difluoromethyl or perfluoroalkyl of 1 to about 12 carbon atoms,

(19) perfluoroaryl of about 6 to about 14 carbon atoms, and

(20) perfluoraralkyl of about 7 to about 15 carbon atoms;

wherein (a) each Y$_1$, Y$_2$, and Y$_3$ is independently selected from the group consisting of halogen, cyano, nitro, tetrazolyl optionally substituted with alkyl of 1 to about 6 carbon atoms, guanidino, amidino, methylamino, methylguanidino, —CF$_3$, —CF$_2$CF$_3$, —CH(CF$_3$)$_2$, —C(OH)(CF$_3$)$_2$, —OCF$_3$, —OCF$_2$CF$_3$, —OCF$_2$H, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NZ$_1$Z$_2$, C(O)OH, —C(O)OZ$_1$, —C(O)NH$_2$, —C(O)NZ$_1$Z$_2$, —P(O)$_3$H$_2$, —P(O)$_3$(Z$_1$)$_2$, —S(O)$_3$H, —S(O)$_p$Z$_1$, —Z$_1$, —OZ$_1$, —OH, —NH$_2$, —NHZ$_1$, —NZ$_1$Z$_2$, N-morpholino, and —S(O)$_p$(CF$_2$)$_q$CF$_3$, wherein p is 0, 1 on 2, q is an integer from 0 to 5, and Z$_1$ and Z$_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms having about 3 to about 9 carbon atoms, or (b) Y$_1$ and Y$_2$ are selected together to be —O[C(Z$_3$)(Z$_4$)]$_r$O— or —O[C(Z$_3$)(Z$_4$)$_{r+i}$—, wherein r is an integer from 1 to 4 and Z$_3$ and Z$_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms having about 3 to about 9 carbon atoms;

(c) D is

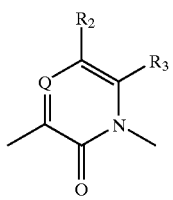

wherein (1) $R_2$ is selected from hydrogen, halogen and alkyl of 1 to about 6 carbon atoms;

(2) $R_3$ is selected from hydrogen, alkyl of 1 to about 6 carbon atoms, cycloalkyl of 3 to about 7 carbon atoms, alkoxy of 1 to about 5 carbon atoms and trifluoromethyl;

(3) Q is —C($R_4$)—;

(4) $R_4$ is hydrogen, alkyl of 1 to about 8 carbon atoms, hydroxy, alkoxy of 1 to about 8 carbon atoms, aralkyl of about 7 to about 15 carbon atoms, alkyl of 1 to about 5 carbon atoms substituted with cycloalkyl of 3 to about 8 carbon atoms, —NH$R_5$, —S(O)$_t R_5$, and C(O)O$R_5$;

(5) t is 0, 1 or 2; and (6) $R_5$ is hydrogen; alkyl of 1 to about 4 carbon atoms, aryl of about 6 to about 14 carbon atoms which is optionally mono-, di- on tri-substituted with $Y_1$, $Y_2$, and/or $Y_3$; heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or $Y_3$; aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$; heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- on tri-substituted on the ring with $Y_1$, $Y_2$, and/on $Y_3$;

(d) J is selected from

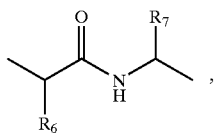

(1)

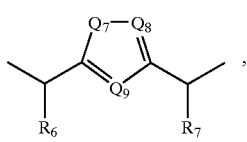

(2)

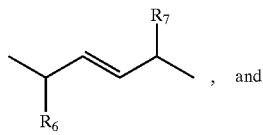

(3)

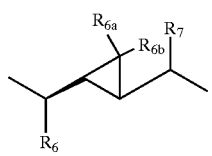

(4)

wherein $R_6$ is hydrogen on alkyl of 1 to about 3 carbon atoms; $R_{6a}$ and $R_{6d}$ are independently selected from hydrogen, fluoro, chloro and alkyl of 1 to about 3 carbon atoms; $R_7$ is hydrogen, alkyl of 1 to about 3 carbon atoms, —C(=O)$R_{7a}$, or —CH$_2$O$R_{7b}$; $R_{7a}$ is alkyl of 1 to about 6 carbon atoms, alkoxy of 1 to about 6 carbon atoms, amino, alkylamino of 1 to about 6 carbon atoms on dialkylamino of 2 to about 12 carbon atoms; $R_{7b}$ is hydrogen, acyl, on alkyl of 1 to about 6 carbon atoms; and $Q_7$, $Q_8$ and $Q_9$ are independently selected from C($R_{6a}$), N, S and O, provided that (i) $Q_7$, $Q_8$ and $Q_9$ are not all C($R_{6a}$) and (ii) only one of $Q_7$, $Q_8$ and $Q_9$ can be O or S;

(e) E is a six membered heterocyclic ring having two ring nitrogen atoms and the remainder of the ring atoms carbon atoms which is substituted with

on a ring carbon and is substituted with $R_{10}$ and $R_{11}$ on different ring carbons wherein (1) $R_8$ is selected from hydrogen, alkyl of about 1 to about 4 carbon atoms, cycloalkyl of 3 to about 7 carbon atoms, —(CF$_2$)$_k$CF$_3$, —O$R_{12}$ and —C(=O)$R_{12}$ wherein $R_{12}$ is alkyl of 1 to about 4 carbon atoms and k is 0, 1, 2 or 3;

(2) $R_9$ is selected from hydrogen and alkyl of 1 to about 4 carbon atoms;

(3) alternatively $R_8$ and $R_9$ are taken together to give a divalent radical of the formula —(CH$_2$)$_w$— wherein w is 3, 4 on 5; and (4) $R_{10}$ and $R_{11}$ are independently selected from hydrogen, alkyl of 1 to about 4 carbon atoms, alkyl of 1 to about 4 carbon atoms substituted with alkoxy of 1 to about 3 carbon atoms, alkoxy of 1 to about 8 carbon atoms, halogen, trifluoromethyl, —OC($R_{13}$)($R_{14}$)—C(=O)—$R_{15}$ wherein $R_{13}$ and $R_{14}$ are independently selected from hydrogen or alkyl of 1 to about 4 carbon atoms, $R_{15}$ is hydroxy, alkoxy of 1 to about 4 carbon atoms or —N($R_{16}$)($R_{17}$) wherein $R_{16}$ and $R_{17}$ are independently hydrogen or alkyl of 1 to about 4 carbon atoms; or pharmaceutically acceptable salts thereof.

2. A compound according to claim 1 wherein E is

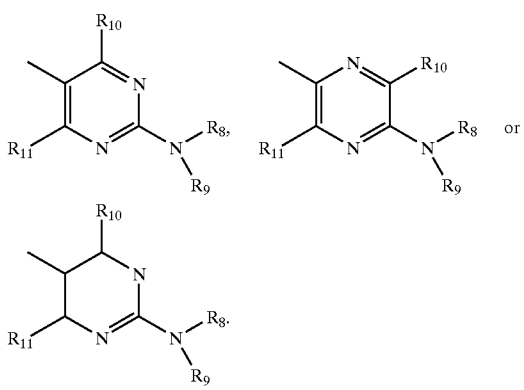

3. A compound according to claim 1 wherein Q is —C($R_4$)—, $R_2$ and $R_4$ are hydrogen and $R_3$ is methyl.

4. A compound according to claim 1 wherein $R_1$ is benzyl, substituted benzyl, phenyl or substituted phenyl.

5. A compound according to claim 4 wherein X is —S($O_2$)—NH—.

6. A compound according to claim 5 wherein $R_4$ is hydrogen.

7. A compound according to claim 3 wherein X is —S($O_2$)—NH—.

8. A compound according to claim 6 wherein $R_2$ is hydrogen and $R_3$ is methyl.

9. A compound according to claim 8 wherein J is selected from

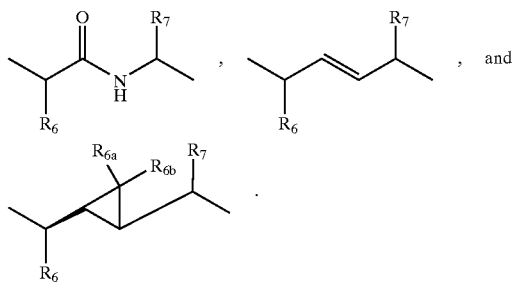

10. A compound according to claim 9 wherein $R_6$ and $R_7$ are hydrogen.

11. A compound according to claim 10 wherein E is selected from

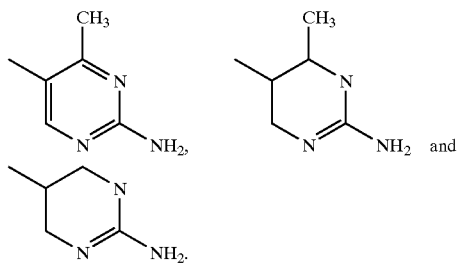

12. A compound according to claim 2 wherein J is selected from

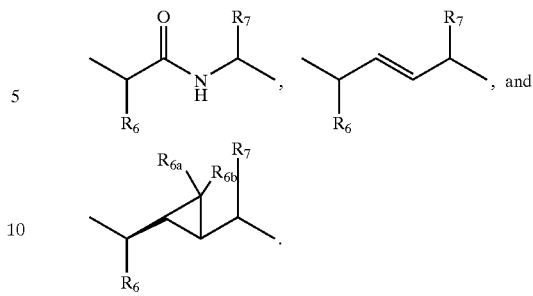

13. A compound according to claim 12 wherein $R_6$ and $R_7$ are hydrogen.

14. A compound according to claim 13 wherein E is selected from

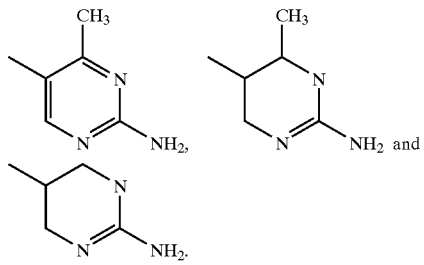

15. A compound according to claim 2 wherein $R_4$ is hydrogen.

16. A compound according to claim 15 wherein $R_1$ is benzyl, substituted benzyl, phenyl or substituted phenyl.

17. A compound according to claim 16 wherein X is —S(O)$_2$—NH—.

18. A compound according to claim 17 wherein E is selected from the group consisting of

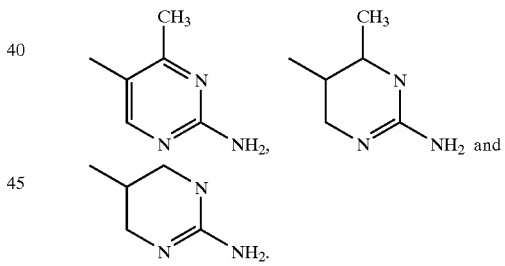

19. A compound according to claim 18 wherein J is

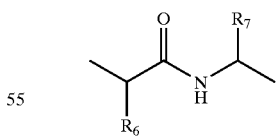

wherein $R_6$ and $R_7$ are hydrogen.

20. A compound according to claim 1 wherein X is —S(O)$_2$—NH—.

21. A compound according to claim 20 wherein $R_1$ is alkyl substituted with $Y_1$ and/or $Y_2$ wherein $Y_1$ and $Y_2$ are independently phenyl or substituted phenyl or alkyl substituted with cycloalkyl which is optionally substituted on the ring with $Y_1$ wherein $Y_1$ is phenyl or substituted phenyl.

22. A compound according to claim 21 wherein $R_8$ and $R_9$ are hydrogen.

23. A compound according to claim 22 wherein J is selected from

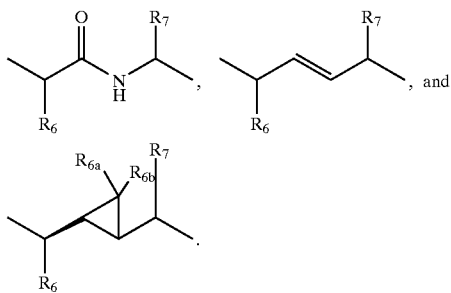

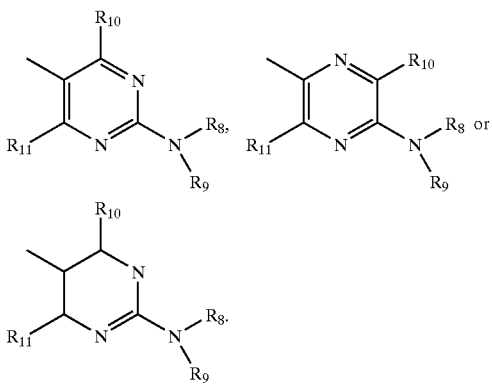

wherein $R_6$ and $R_7$, are hydrogen.

24. A compound according to claim 23 wherein E is

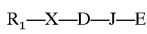

25. A compound of the formula:

$R_1$—X—D—J—E wherein
(a) X is selected from the group consisting of —S(O)$_2$—NH—, —N(R')—S(O)$_2$—NH—, —C(=O)—NH—, —OC(=O)—NH—, and —N(R')C(=O)—NH—, wherein R' is selected from hydrogen, alkyl of 1 to about 4 carbon atoms, aryl of about 6 to about 14 carbon atoms and aralkyl of about 6 to about 16 carbon atoms;
(b) $R_1$ is selected from the group consisting of:
(1) alkyl of 1 to about 12 carbon atoms which is optionally substituted with $Y_1$ and/or $Y_2$,
(2) alkyl of 1 to about 3 carbon atoms substituted with cycloalkyl of about 3 to about 8 carbon atoms which is optionally mono-, di-, or tri-substituted on the ring with $Y_1$, $Y_2$ and/or $Y_3$,
(3) cycloalkyl of 3 to about 15 carbon atoms, which is optionally mono-, di-, or tri-substituted on the ring with $Y_1$, $Y_2$ and/or $Y_3$,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with $Y_1$, $Y_2$ and/or $Y_3$,
(5) heterocyclo of 4 to about 10 ring atoms with the ring atoms selected from carbon and heteroatoms, wherein the heteroatoms are selected from the group consisting of oxygen, nitrogen, and S(O)$_i$, including

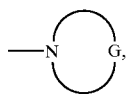

wherein

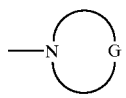

is a 5 to 7 member heterocycle of 3 to 6 ring carbon atoms, where G is —CH$_2$—, —O—, —S(=O)—, —S(O)$_2$— or —S—, which is optionally mono-, di-, or tri-substituted on the ring carbons with $Y_1$, $Y_2$ and/or $Y_3$,
(6) alkenyl of about 2 to about 6 carbon atoms which is optionally substituted with cycloalkyl of about 5 to about 8 carbon atoms, which is optionally mono-, di-, or tri-substituted on the ring carbons with $Y_1$, $Y_2$ and/or $Y_3$,
(7) aryl of about 6 to about 14 carbon atoms which is optionally mono-, di- or tri-substituted with $Y_1$, $Y_2$, and/or $Y_3$,
(8) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or $Y_3$,
(9) aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$,
(10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy on halogen and optionally mono-, di-, or tri-substituted on the ring with $Y_1$, $Y_2$, and/or $Y_3$,
(11) aralkenyl of about 8 to about 16 carbon atoms which is optionally mono-, di-, on tri-substituted on the aryl ring with $Y_1$, $Y_2$, and/or $Y_3$,
(12) heteroaralkenyl of 5 to 14 ring atoms with the ring atoms selected from carbon and heteroatoms, wherein the heteroatoms are selected from oxygen, nitrogen, and sulfur, and which is optionally mono-, di-, or tri-substituted on the ring with $Y_1$, $Y_2$, and/or $Y_3$, (13)

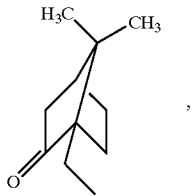

-continued

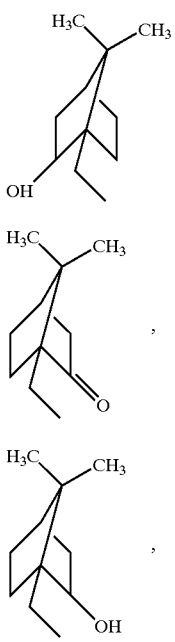

(17) fused carbocyclic alkyl of about 5 to about 15 carbon atoms,
(18) difluoromethyl or perfluoroalkyl of 1 to about 12 carbon atoms,
(19) perfluoroaryl of about 6 to about 14 carbon atoms, and
(20) perfluoraralkyl of about 7 to about 15 carbon atoms;

wherein
(a) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, —$CF_3$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NZ_1Z_2$, $C(O)OH$, —$C(O)OZ_1$, —$C(O)NH_2$, —$C(O)NZ_1Z_2$, —$P(O)_3H_2$, —$P(O)_3(Z_1)_2$, —$S(O)_3H$, —$S(O)_pZ_1$, —$Z_1$, —$OZ_1$, —$OH$, —$NH_2$, —$NHZ_1$, —$NZ_1Z_2$, N-morpholino, and —$S(O)_p(CF_2)_qCF_3$, wherein p is 0, 1 on 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms having about 3 to about 9 carbon atoms, or
(b) $Y_1$ and $Y_2$ are selected together to be —O[C($Z_3$)($Z_4$)]$_r$O— or —O[C($Z_3$)($Z_4$)$_{r+i}$—, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms having about 3 to about 9 carbon atoms;

(c) D is

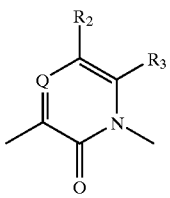

wherein
(1) $R_2$ is selected from hydrogen, halogen and alkyl of 1 to about 6 carbon atoms;
(2) $R_3$ is selected from hydrogen, alkyl of 1 to about 6 carbon atoms, cycloalkyl of 3 to about 7 carbon atoms, alkoxy of 1 to about 5 carbon atoms and trifluoromethyl;
(3) Q is —C($R_4$)—;
(4) $R_4$ is hydrogen, alkyl of 1 to about 8 carbon atoms, hydroxy, alkoxy of 1 to about 8 carbon atoms, aralkyl of about 7 to about 15 carbon atoms, alkyl of 1 to about 5 carbon atoms substituted with cycloalkyl of 3 to about 8 carbon atoms, —$NHR_5$, —S (O)$_tR_5$, and $C(O)OR_5$;
(5) t is 0, 1 or 2; and
(6) $R_5$ is hydrogen; alkyl of 1 to about 4 carbon atoms, aryl of about 6 to about 14 carbon atoms which is optionally mono-, di- on tri-substituted with $Y_1$, $Y_2$, and/or $Y_3$; heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or $Y_3$; aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$; heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- on tri-substituted on the ring with $Y_1$, $Y_2$, and/on $Y_3$;

(d) J is selected from

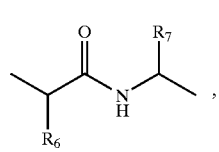

(1)

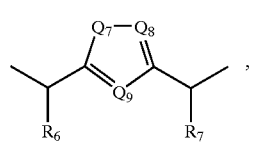

(2)

-continued

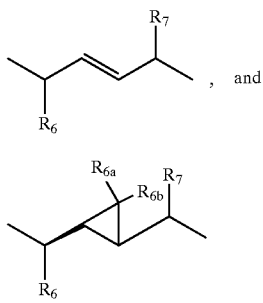

wherein $R_6$ is hydrogen on alkyl of 1 to about 3 carbon atoms; $R_{6a}$ and $R_{6b}$ are independently selected from hydrogen, fluoro, chloro and alkyl of 1 to about 3 carbon atoms; $R_7$ is hydrogen, alkyl of 1 to about 3 carbon atoms, —C(=O)$R_{7a}$, or —CH$_2$O$R_{7b}$; $R_{7a}$ is alkyl of 1 to about 6 carbon atoms, alkoxy of 1 to about 6 carbon atoms, amino, alkylamino of 1 to about 6 carbon atoms on dialkylamino of 2 to about 12 carbon atoms; $R_{7b}$ is hydrogen, acyl, on alkyl of 1 to about 6 carbon atoms; and $Q_7$, $Q_8$ and $Q_9$ are independently selected from $C(R_{6a})$, N, S and O, provided that (i) $Q_7$, $Q_8$ and $Q_9$ are not all $C(R_{6a})$ and (ii) only one of $Q_7$, $Q_8$ and $Q_9$ can be O or S;

(e) is selected from the group consisting of:

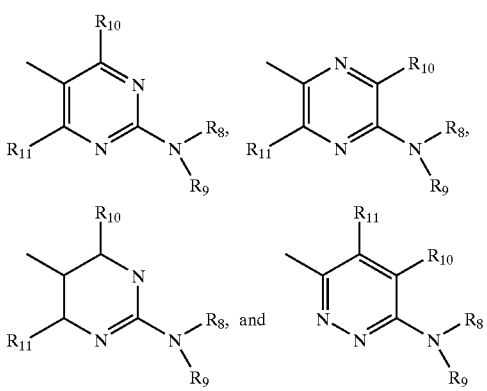

wherein
(1) $R_8$ is selected from hydrogen, alkyl of about 1 to about 4 carbon atoms, cycloalkyl of 3 to about 7 carbon atoms, —(CF$_2$)$_k$CF$_3$, —O$R_{12}$ and —C(=O) $R_{12}$ wherein $R_{12}$ is alkyl of 1 to about 4 carbon atoms and k is 0, 1, 2 or 3;
(2) $R_9$ is selected from hydrogen and alkyl of 1 to about 4 carbon atoms;
(3) alternatively $R_8$ and $R_9$ are taken together to give a divalent radical of the formula —(CH$_2$)$_w$— wherein w is 3, 4 on 5; and
(4) $R_{10}$ and $R_{11}$ are independently selected from hydrogen, alkyl of 1 to about 4 carbon atoms, alkyl of 1 to about 4 carbon atoms substituted with alkoxy of 1 to about 3 carbon atoms, alkoxy of 1 to about 8 carbon atoms, halogen, trifluoromethyl, —OC($R_{13}$)($R_{14}$)—C(=O)—$R_{15}$ wherein $R_{13}$ and $R_{14}$ are independently selected from hydrogen or alkyl of 1 to about 4 carbon atoms, $R_{15}$ is hydroxy, alkoxy of 1 to about 4 carbon atoms or —N($R_{16}$)($R_{17}$) wherein $R_{16}$ and $R_{17}$ are independently hydrogen or alkyl of 1 to about 4 carbon atoms; or pharmaceutically acceptable salts thereof.

26. A compound according to claim 25 which is selected from the group consisting of:

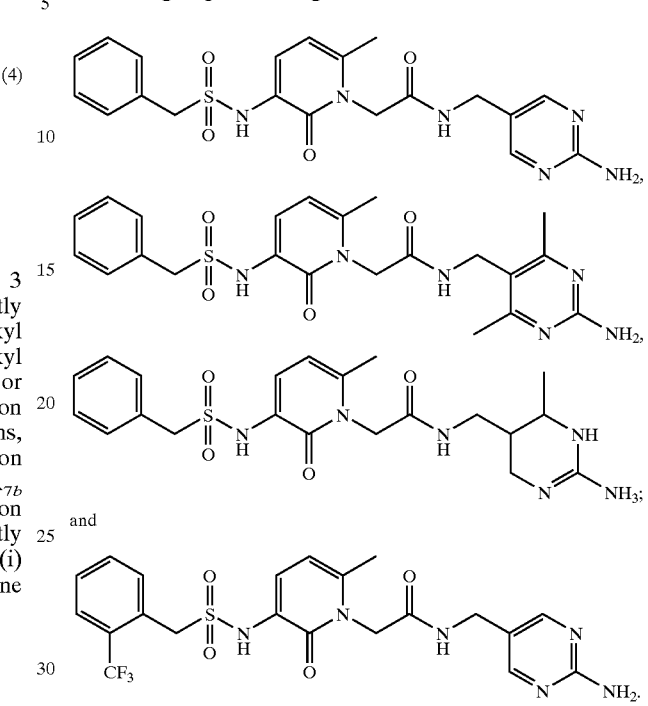

27. A compound according to claim 25 which is selected from the group consisting of:

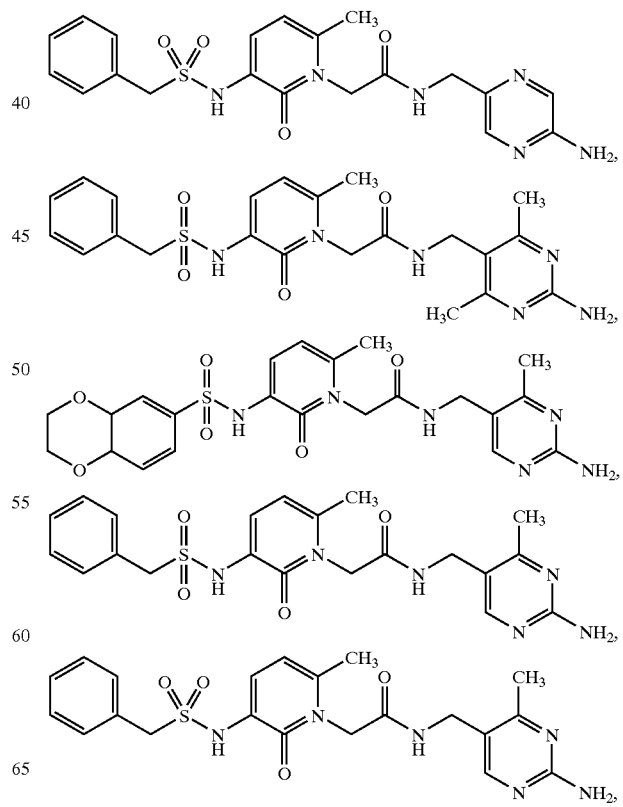

and

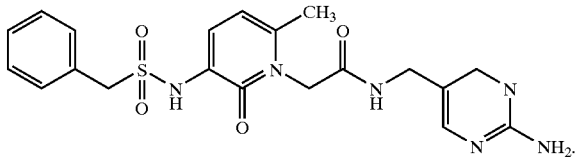

28. A pharmaceutical composition for treating or decreasing the incidence of a condition in a mammal characterized by abnormal thrombosis, comprising a therapeutically acceptable carrier, and a therapeutically effective amount of compound of claim 1.

29. A pharmaceutical composition for treating or decreasing the incidence of a condition in a mammal characterized by abnormal thrombosis, comprising a therapeutically acceptable carrier, and a therapeutically effective amount of compound of claim 2.

30. A pharmaceutical composition for treating or decreasing the incidence of a condition in a mammal characterized by abnormal thrombosis, comprising a therapeutically acceptable carrier, and a therapeutically effective amount of compound of claim 10.

31. A pharmaceutical composition for treating or decreasing the incidence of a condition in a mammal characterized by abnormal thrombosis, comprising a therapeutically acceptable carrier, and a therapeutically effective amount of compound of claim 12.

32. A pharmaceutical composition for treating or decreasing the incidence of a condition in a mammal characterized by abnormal thrombosis, comprising a therapeutically acceptable carrier, and a therapeutically effective amount of compound of claim 22.

33. A pharmaceutical composition for treating or decreasing the incidence of a condition in a mammal characterized by abnormal thrombosis, comprising a therapeutically acceptable carrier, and a therapeutically effective amount of compound of claim 26.

34. A pharmaceutical composition for treating or decreasing the incidence of a condition in a mammal characterized by abnormal thrombosis, comprising a therapeutically acceptable carrier, and a therapeutically effective amount of compound of claim 27.

35. A pharmaceutical composition for treating or decreasing the incidence of a condition in a mammal characterized by abnormal thrombosis, comprising a therapeutically acceptable carrier, and a therapeutically effective amount of compound of claim 25.

36. A method for treating or decreasing the incidence of a condition in a mammal characterized by abnormal thrombosis, comprising administering to said mammal a therapeutically effective amount of the compound of claim 1.

37. A method for treating or decreasing the incidence of a condition in a mammal characterized by abnormal thrombosis, comprising administering to said mammal a therapeutically effective amount of the compound of claim 2.

38. A method for treating or decreasing the incidence of a condition in a mammal characterized by abnormal thrombosis, comprising administering to said mammal a therapeutically effective amount of the compound of claim 10.

39. A method for treating or decreasing the incidence of a condition in a mammal characterized by abnormal thrombosis, comprising administering to said mammal a therapeutically effective amount of the compound of claim 12.

40. A method for treating or decreasing the incidence of a condition in a mammal characterized by abnormal thrombosis, comprising administering to said mammal a therapeutically effective amount of the compound of claim 22.

41. A method for treating or decreasing the incidence of a condition in a mammal characterized by abnormal thrombosis, comprising administering to said mammal a therapeutically effective amount of the compound of claim 26.

42. A method for treating or decreasing the incidence of a condition in a mammal characterized by abnormal thrombosis, comprising administering to said mammal a therapeutically effective amount of the compound of claim 27.

43. A method for treating on decreasing the incidence of a condition in a mammal characterized by abnormal thrombosis, comprising administering to said mammal a therapeutically effective amount of the compound of claim 25.

* * * * *